US012778399B2

(12) United States Patent
Dekel et al.

(10) Patent No.: US 12,778,399 B2
(45) Date of Patent: Nov. 3, 2026

(54) SYSTEMS, DEVICES, APPS, AND METHODS FOR CAPSULE ENDOSCOPY PROCEDURES

(71) Applicant: Given Imaging LTD., Yoqneam (IL)

(72) Inventors: Eyal Dekel, Haifa (IL); Roni Keynan, Hadera (IL)

(73) Assignee: Given Imaging LTD., Yokneam (IL)

( * ) Notice: Subject to any disclaimer, the term of this patent is extended or adjusted under 35 U.S.C. 154(b) by 108 days.

(21) Appl. No.: 18/882,079

(22) Filed: Sep. 11, 2024

(65) Prior Publication Data

US 2025/0000349 A1 Jan. 2, 2025

Related U.S. Application Data

(63) Continuation-in-part of application No. 17/611,363, filed as application No. PCT/US2020/033341 on May 17, 2020, now Pat. No. 12,185,906.
(Continued)

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00009* (2013.01); *A61B 1/00016* (2013.01);
(Continued)

(58) Field of Classification Search
CPC .......... A61B 1/000096; A61B 1/00016; A61B 1/0002; A61B 1/041; A61B 5/0022;
(Continued)

(56) References Cited

U.S. PATENT DOCUMENTS 8,423,123 B2 4/2013 Horn
8,900,124 B2 12/2014 Hirakawa
(Continued)

FOREIGN PATENT DOCUMENTS

CN 109272483 A 1/2019
EP 2165639 A1 3/2010
(Continued)

OTHER PUBLICATIONS

Chinese Office Action for Application No. 202080036543.2 dated Aug. 28, 2025, 18 pages with English translation.
(Continued)

*Primary Examiner* — Fayyaz Alam
(74) *Attorney, Agent, or Firm* — Carter, DeLuca & Farrell, LLP

(57) ABSTRACT

Systems, devices, methods for capsule endoscopy procedures are disclosed. A swallowable capsule apparatus includes one or more processors and one or more memory storing instructions. The instructions, when executed by the one or more processors, cause the swallowable capsule apparatus at least to perform: capturing in-vivo images over time of at least a portion of a gastrointestinal tract (GIT) of a person; pruning, over time, at least a portion of the in-vivo images; and communicating images of the in-vivo images, which were not pruned, to a receiver device external to the person.

17 Claims, 29 Drawing Sheets

Related U.S. Application Data

(60) Provisional application No. 62/867,050, filed on Jun. 26, 2019, provisional application No. 62/849,508, filed on May 17, 2019.

(51) Int. Cl.
*G06T 7/00* (2017.01)
*G06T 7/70* (2017.01)

(52) U.S. Cl.
CPC .............. *G06T 7/0016* (2013.01); *G06T 7/70* (2017.01); *G06T 2207/10068* (2013.01); *G06T 2207/30028* (2013.01); *G06T 2207/30244* (2013.01)

(58) Field of Classification Search
CPC .............. A61B 5/4255; A61B 1/00055; A61B 1/00009; G16H 20/10; G16H 20/60; G16H 40/63; G16H 40/67; G16H 50/20; G16H 80/00
See application file for complete search history.

(56) References Cited

U.S. PATENT DOCUMENTS

| | | | | |
|---|---|---|---|---|
| 9,060,673 | B2 | 6/2015 | Krupnik et al. | |
| 2002/0128873 | A1* | 9/2002 | Shimizu | G16H 30/20 705/3 |
| 2005/0075537 | A1 | 4/2005 | Chen et al. | |
| 2005/0196023 | A1 | 9/2005 | Chen et al. | |
| 2007/0066875 | A1 | 3/2007 | Horn et al. | |
| 2007/0078335 | A1* | 4/2007 | Horn | A61B 1/04 600/425 |
| 2007/0167715 | A1* | 7/2007 | Shigemori | A61B 1/00016 600/407 |
| 2009/0023993 | A1 | 1/2009 | Davidson et al. | |
| 2009/0077128 | A1 | 3/2009 | Kimoto | |
| 2009/0203964 | A1* | 8/2009 | Shimizu | G16H 40/63 600/109 |
| 2010/0094104 | A1* | 4/2010 | Nagase | G16H 30/20 600/109 |
| 2016/0048637 | A1* | 2/2016 | Nishiyama | A61B 1/041 382/305 |
| 2016/0342767 | A1 | 11/2016 | Narasimhan et al. | |
| 2017/0119236 | A1 | 5/2017 | Hyde et al. | |
| 2017/0272699 | A1 | 9/2017 | Stopek | |
| 2018/0168438 | A1* | 6/2018 | Gazdzinski | A61B 1/0005 |
| 2019/0313942 | A1* | 10/2019 | Lu | A61B 5/14539 |
| 2020/0043613 | A1 | 2/2020 | Zhang et al. | |

FOREIGN PATENT DOCUMENTS

| | | | |
|---|---|---|---|
| JP | 2007125373 | A | 5/2007 |
| JP | 2007151809 | A | 6/2007 |
| JP | 2013075244 | A | 4/2013 |
| JP | 6425868 | B1 | 11/2018 |
| WO | 2009008125 | A1 | 1/2009 |
| WO | 2010082993 | A2 | 7/2010 |
| WO | 2012137705 | A1 | 10/2012 |
| WO | 2018002935 | A1 | 1/2018 |
| WO | 2018105221 | A1 | 6/2018 |
| WO | 2018112255 | A1 | 6/2018 |
| WO | 2019087971 | A1 | 5/2019 |

OTHER PUBLICATIONS

Karargyris, A. et al. "Wireless Capsule Endoscopy and Endoscopic Imaging: A Survey on Various Methodologies Presented", IEEE Engineering In Medicine And Biology Magazine, vol. 28, No. 1, pp. 72-83 (2010).
International Search Report and Written Opinion of the International Searching Authority issued in corresponding application PCT/US2020/033341 mailed Oct. 27, 2020 (11 pages).
Extended European Search Report issued in corresponding application EP 19873352.9 dated Mar. 22, 2022 (14 pages).
Office Action issued in corresponding Japanese Application No. 2021-521094 mailed Jul. 14, 2023, together with English Language translation (12 pages).
Japanese Office Action for application No. 2021-521094 dated Jan. 5, 2024 with English Translation, 6 pages.
Chinese Office Action for application No. 201980075047.5 dated Mar. 19, 2024 with English translation, 14 pages.
Japanese Office Action for application No. 2021-568563 dated May 29, 2024 with English Translation, 9 pages.
Pogorelov, Konstantin, et al. "A holistic multimedia system for gastrointestinal tract disease detection." Proceedings of the 8th ACM on Multimedia Systems Conference. 2017, 12 pages.
Chinese Office Action for application No. 202080036543.2 dated Nov. 20, 2025 with English translation, 22 pages.
European Examination Report for Application No. 20 731 290.1 dated Jan. 27, 2025, 6 pages.
European Examination Report for Application No. 19 873 352.9 dated Jan. 31, 2025, 6 pages.
Chinese Office Action for application No. 202080036543.2 dated Feb. 25, 2025 with English translation, 27 pages total.
Japanese Notice of Allowance dated Jun. 2, 2025 for application No. 2021-568563 with English translation, 4 pages.
European Examination Report for Application No. 19 873 352.9 dated Mar. 16, 2026, 9 pages.
European Examination Report for application No. 20 731 290.1 dated Mar. 16, 2026, 9 pages.
Office Action from U.S. Appl. No. 18/798,928 dated Jun. 3, 2026, 17 pages.

* cited by examiner

SYSTEMS, DEVICES, APPS, AND METHODS FOR CAPSULE ENDOSCOPY PROCEDURES

CROSS-REFERENCE TO RELATED APPLICATIONS

The present application is a continuation in part of U.S. patent application Ser. No. 17/611,363, filed Nov. 15, 2021, which is a U.S. National Stage Application filed under 35 U.S.C. § 371(a) of International Patent Application No. PCT/US2020/033341, filed May 17, 2020, which claims the benefit of and priority to U.S. Provisional Application No. 62/849,508, filed May 17, 2019, and to U.S. Provisional Application No. 62/867,050, filed Jun. 26, 2019. The entire contents of each of the foregoing applications are hereby incorporated by reference herein.

FIELD

The present disclosure relates generally to capsule endoscopy procedures, and more specifically, to flexible systems, devices, apps, and methods for conducting capsule endoscopy procedures in a variety of manners and configurations.

BACKGROUND

Capsule endoscopy (CE) allows examining the entire GIT endoscopically. There are capsule endoscopy systems and methods that are aimed at examining specific portions of the GIT, such as the small bowel or the colon. CE is a non-invasive procedure which does not require the patient to be admitted to a hospital, and the patient can continue most daily activities while the capsule is in the body. The patient may also continue taking regular medications.

On a typical CE procedure, the patient is referred to a procedure by a physician. The patient then arrives at a medical facility (e.g., a clinic or a hospital), to perform the procedure. The patient is admitted by a HealthCare Provider (HCP) such as a nurse and/or a physician, who sets up the specific procedure, manages, and supervises it. In some cases, the HCP may be the referring physician. The capsule, which is about the size of a multi-vitamin, is swallowed by the patient under the supervision of the HCP at the medical facility and the patient is provided with a wearable device, e.g., a sensor belt and a recorder placed in a pouch and strap to be placed around the patient's shoulder. The wearable device typically includes a storage device. The patient may be given guidance and/or instructions and then released to his daily activities. The capsule captures images as it travels naturally through the GIT. Images and additional data (e.g., metadata) are then transmitted to the recorder that is worn by the patient. The capsule is disposable and passes naturally with a bowel movement. The procedure data (e.g., the captured images or a portion of them and additional metadata) is stored on the storage device of the wearable device.

The wearable device is typically returned by the patient to the medical facility with the procedure data stored thereon. The procedure data is then downloaded to a computing device typically located at the medical facility, which has an engine software stored thereon. The received procedure data is then processed by the engine to a compiled study. Typically, the number of images to be processed is of the order of tens of thousands and about 90,000 to 100,000 on average. Typically, a compiled study includes thousands of images (around 6,000 to 9,000). Since the patient is required to return the wearable device to the HCP or medical facility and only then the procedure data would be processed, a compiled study and a report usually would not be generated at the same day of the procedure or shortly afterward.

A reader (which may be the procedure supervising physician, a dedicated physician or the referring physician) may access the compiled study via a reader application. The reader then reviews the compiled study, evaluates the procedure and provides his input via the reader application. Since the reader needs to review thousands of images, the reading time of a compiled study may usually take between half an hour to an hour on average and the reading task may be tiresome. A report is then generated by the reader application based on the compiled study and the reader's input. On average, it would take an hour to generate a report. The report may include, for example, images of interest, e.g., images which are identified as including pathologies, evaluation or diagnosis of the patient's medical condition based on the procedure's data and/or recommendations for follow-up and/or treatment. The report may then be forwarded to the referring physician. The referring physician may decide on a required follow-up or treatment based on the report.

Some capsule procedures, specifically those aimed at the colon, may require patient preparation. For example, the colon and/or small bowel may be required to be emptied. To clean the bowel, a physician may determine a regimen, e.g., prescribe a diet and/or medication, such as prep solution and/or laxatives, for the patient to ingest before the procedure. It is important that the patient follow all of the instructions and ingest all preparation medication to ensure the patient's GIT can be seen properly. In addition, the patient may be also required to follow a diet and/or take medication (e.g., laxatives) after the capsule is swallowed and during the procedure (herein referred as "boosts"). The recorder may alert the patient if this step needs to be repeated to ensure a complete procedure. Typically, a physician (e.g., the referring physician or the physician supervising the procedure) decides on a preparation that suits the patient and the desired type of capsule procedure.

SUMMARY

The present disclosure relates to systems, devices, apps, and methods for capsule endoscopy procedures. More particularly, the present disclosure relates to systems, devices, apps, and methods for coordinating, conducting, evaluating, and monitoring numerous capsule endoscopy procedures simultaneously. Networked and systems and devices provide the capability for patients to conduct capsule endoscopy procedures partially or entirely outside a medical facility, if they wish, and for healthcare professionals to remotely access and evaluate data from the capsule endoscopy procedure during and/or after the procedure. The disclosed systems, devices, apps, and methods are flexible and permit capsule endoscopy procedures to be conducted in a variety of manners and configurations.

In accordance with aspects of the present disclosure, a swallowable capsule apparatus includes one or more processors and one or more memory storing instructions. The instructions, when executed by the one or more processors, cause the swallowable capsule apparatus at least to perform: capturing in-vivo images over time of at least a portion of a gastrointestinal tract (GIT) of a person; pruning, over time, at least a portion of the in-vivo images; and communicating images of the in-vivo images, which were not pruned, to a receiver device external to the person.

In various embodiments of the swallowable capsule apparatus, in the pruning, the instructions, when executed by the one or more processors, cause the swallowable capsule apparatus at least to perform: pruning at least a first portion of the in-vivo images at a first degree based on a first location indication specifying a first location in the GIT where the swallowable capsule apparatus captured the first portion of the in-vivo images; and pruning at least a second portion of the in-vivo images at a second degree based on a second location indication specifying a second location in the GIT where the swallowable capsule apparatus captured the second portion of the in-vivo images.

In various embodiments of the swallowable capsule apparatus, the instructions, when executed by the one or more processors, further cause the swallowable capsule apparatus at least to perform: generating the first location indication based on at least the first portion of the in-vivo images; and generating the second location indication based on at least the second portion of the in-vivo images.

In various embodiments of the swallowable capsule apparatus, the first location indication and the second location indication are generated by at least one of: a wearable device configured to be secured to the person, a mobile device carried by the person, or a remote computing system remote from the swallowable capsule apparatus.

In various embodiments of the swallowable capsule apparatus, the first location is a small bowel of the person and the second location is a colon of the person, and the first degree is greater than the second degree such that in-vivo images of the small bowel are pruned to a greater degree than in-vivo images of the colon.

In various embodiments of the swallowable capsule apparatus, the first location is a location of the GIT having no suspected pathology and the second location is a location of the GIT having a suspected pathology, and the first degree is greater than the second degree such that in-vivo images of the location of the GIT having no suspected pathology are pruned to a greater degree than in-vivo images of the location of the GIT having a suspected pathology.

In various embodiments of the swallowable capsule apparatus, the pruning the at least the first portion of the in-vivo images at the first degree is different from the pruning the at least the second portion of the in-vivo images at the second degree by at least one of: a rate of pruning images, where the first degree of pruning has a higher rate of pruning images than the second degree of pruning, a similarity threshold for pruning the in-vivo images, where the first degree of pruning has a lower similarity threshold for pruning the in-vivo images than the second degree of pruning, or a difference threshold for pruning the in-vivo images, where the first degree of pruning has a higher difference threshold for pruning the in-vivo images than the second degree of pruning.

In accordance with aspects of the present disclosure, a processor-implemented method in a swallowable capsule apparatus includes: capturing, by the swallowable capsule apparatus, in-vivo images over time of at least a portion of a gastrointestinal tract (GIT) of a person; pruning, by the swallowable capsule apparatus over time, at least a portion of the in-vivo images; and communicating, by the swallowable capsule apparatus, images of the in-vivo images, which were not pruned, to a receiver device external to the person.

In various embodiments of the processor-implemented method, the pruning includes: pruning, by the swallowable capsule apparatus, at least a first portion of the in-vivo images at a first degree based on a first location indication specifying a first location in the GIT where the swallowable capsule apparatus captured the first portion of the in-vivo images; and pruning, by the swallowable capsule apparatus, at least a second portion of the in-vivo images at a second degree based on a second location indication specifying a second location in the GIT where the swallowable capsule apparatus captured the second portion of the in-vivo images.

In various embodiments of the processor-implemented method, the method further includes: generating, by the swallowable capsule apparatus, the first location indication based on at least a first portion of the in-vivo images; and generating, by the swallowable capsule apparatus, the second location indication based on at least a second portion of the in-vivo images.

In various embodiments of the processor-implemented method, the first location indication and the second location indication are generated by at least one of: a wearable device configured to be secured to the person, a mobile device carried by the person, or a remote computing system remote from the swallowable capsule apparatus.

In various embodiments of the processor-implemented method, the first location is a small bowel of the person and the second location is a colon of the person, and the first degree is greater than the second degree such that in-vivo images of the small bowel are pruned, by the swallowable capsule apparatus, to a greater degree than in-vivo images of the colon.

In various embodiments of the processor-implemented method, the first location is a location of the GIT having no suspected pathology and the second location is a location of the GIT having a suspected pathology, and the first degree is greater than the second degree such that in-vivo images of the location of the GIT having no suspected pathology are pruned, by the swallowable capsule apparatus, to a greater degree than in-vivo images of the location of the GIT having a suspected pathology.

In various embodiments of the processor-implemented method, the pruning the at least the first portion of the in-vivo images at the first degree is different from the pruning the at least the second portion of the in-vivo images at the second degree by at least one of: a rate of pruning images, wherein the first degree of pruning has a higher rate of pruning images than the second degree of pruning, a similarity threshold for pruning the in-vivo images, wherein the first degree of pruning has a lower similarity threshold for pruning the in-vivo images than the second degree of pruning, or a difference threshold for pruning the in-vivo images, wherein the first degree of pruning has a higher difference threshold for pruning the in-vivo images than the second degree of pruning.

In accordance with aspects of the present disclosure, a non-transitory processor-readable medium stores instructions which, when executed by one or more processors in a swallowable capsule apparatus, cause the swallowable capsule apparatus at least to perform: capturing in-vivo images over time of at least a portion of a gastrointestinal tract (GIT) of a person; pruning, over time, at least a portion of the in-vivo images; and communicating images of the in-vivo images, which were not pruned, to a receiver device external to the person.

In various embodiments of the non-transitory processor-readable medium, in the pruning, the instructions, when executed by the one or more processors, cause the swallowable capsule apparatus at least to perform: pruning, by the swallowable capsule apparatus, at least a first portion of the in-vivo images at a first degree based on a first location indication specifying a first location in the GIT where the swallowable capsule apparatus captured the first portion of the in-vivo images; and pruning, by the swallowable capsule apparatus, at least a second portion of the in-vivo images at a second degree based on a second location indication specifying a second location in the GIT where the swallowable capsule apparatus captured the second portion of the in-vivo images.

In various embodiments of the non-transitory processor-readable medium, the instructions, when executed by the one or more processors, further cause the swallowable capsule apparatus at least to perform: generating the first location indication based on at least the first portion of the in-vivo images; and generating the second location indication based on at least the second portion of the in-vivo images.

In various embodiments of the non-transitory processor-readable medium, the first location is a small bowel of the person and the second location is a colon of the person, and the first degree is greater than the second degree such that in-vivo images of the small bowel are pruned to a greater degree than in-vivo images of the colon.

In various embodiments of the non-transitory processor-readable medium, the first location is a location of the GIT having no suspected pathology and the second location is a location of the GIT having a suspected pathology, and the first degree is greater than the second degree such that in-vivo images of the location of the GIT having no suspected pathology are pruned to a greater degree than in-vivo images of the location of the GIT having a suspected pathology.

In various embodiments of the non-transitory processor-readable medium, the pruning the at least the first portion of the in-vivo images at the first degree is different from the pruning the at least the second portion of the in-vivo images at the second degree by at least one of: a rate of pruning images, wherein the first degree of pruning has a higher rate of pruning images than the second degree of pruning, a similarity threshold for pruning the in-vivo images, wherein the first degree of pruning has a lower similarity threshold for pruning the in-vivo images than the second degree of pruning, or a difference threshold for pruning the in-vivo images, wherein the first degree of pruning has a higher difference threshold for pruning the in-vivo images than the second degree of pruning.

The details of one or more embodiments of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

The above and other aspects and features of the disclosure will become more apparent in view of the following detailed description when taken in conjunction with the accompanying drawings wherein like reference numerals identify similar or identical elements.

Figure 1:
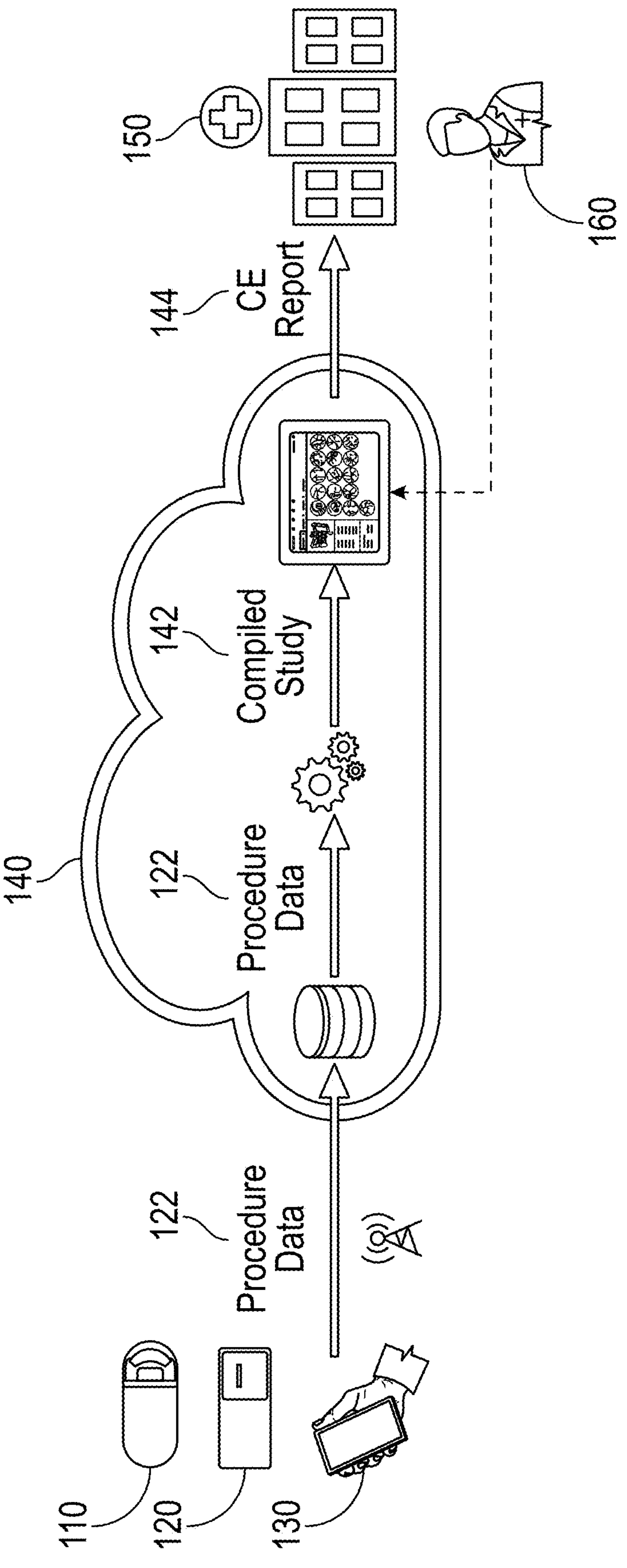
FIG. 1 is a diagram of an exemplary remote computing configuration for CE procedures, in accordance with aspects of the disclosure.

It will be appreciated that for simplicity and clarity of illustration, elements shown in the figures have not necessarily been drawn to scale. For example, the dimensions and/or aspect ratio of some of the elements can be exaggerated relative to other elements for clarity. Further, where considered appropriate, reference numerals can be repeated among the figures to indicate corresponding or analogous elements throughout the serial views.

DETAILED DESCRIPTION

The present disclosure relates to systems, devices, apps, and methods for capsule endoscopy procedures. More particularly, the present disclosure relates to systems, devices, apps, and methods for coordinating, conducting, evaluating, and monitoring numerous capsule endoscopy procedures performed simultaneously. Networked and systems and devices provide the capability for patients to conduct capsule endoscopy procedures partially or entirely outside a medical facility, if they wish, and for healthcare professionals to remotely monitor, access and evaluate data from the capsule endoscopy procedure during and/or after the procedure from a networked device. The disclosed systems and methods are flexible and permit capsule endoscopy procedures to be conducted in a variety of manners and configurations. The disclosed systems, methods, devices and apps are patient-friendly and may improve the case of use for both the patient and the Health Care Provider thereby allowing better performance and patient compliance. Furthermore, by reducing the read-time of a capsule endoscopy compiled study, the disclosed systems, methods, devices and apps allow for better diagnosis and treatment.

In the following detailed description, specific details are set forth in order to provide a thorough understanding of the disclosure. However, it will be understood by those skilled in the art that the disclosure may be practiced without these specific details. In other instances, well-known methods, procedures, and components have not been described in detail so as not to obscure the present disclosure. Some features or elements described with respect to one system may be combined with features or elements described with respect to other systems. For the sake of clarity, discussion of same or similar features or elements may not be repeated.

Although the disclosure is not limited in this regard, discussions utilizing terms such as, for example, "processing," "computing," "calculating," "determining," "establishing," "analyzing," "checking," or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes.

Although the disclosure is not limited in this regard, the terms "plurality" and "a plurality" as used herein may include, for example, "multiple" or "two or more." The terms "plurality" or "a plurality" may be used throughout the specification to describe two or more components, devices, elements, units, parameters, or the like. The term set, when used herein, may include one or more items. Unless explicitly stated, the methods described herein are not constrained to a particular order or sequence. Additionally, some of the described methods or elements thereof can occur or be performed simultaneously, at the same point in time, or concurrently.

The term "classify" may be used throughout the specification to indicate a decision that assigns one category among a set of categories to an image/frame.

The terms "image" or "frame" may be used interchangeably herein.

The term "gastrointestinal tract" ("GIT"), as used herein, may relate to and include the entire digestive system extending from the mouth to the anus, including the pharynx, esophagus, stomach and intestines, and any other portion. The terms "GIT portion" or "portion of a GIT" may refer to any portion of the GIT (anatomically distinct or not). Depending on context, the term GIT may refer to a portion of the entire digestive system but not the entire digestive system.

The term "location" and its derivatives, as referred to herein with respect to an image, may refer to the estimated location of the capsule along the GIT while capturing the image or to the estimated location of the portion of the GIT shown in the image along the GIT.

A type of CE procedure may be determined based on, inter alia, the portion of the GIT that is of interest and is to be imaged (e.g., the colon or the small bowel ("SB")), or based on the specific use (e.g., for checking the status of a GI disease, such as Crohn's disease, or for colon cancer screening).

The terms "surrounding" or "adjacent," as referred to herein with respect to images (e.g., images that surround another image(s), or that are adjacent to other image(s)), may relate to spatial and/or temporal characteristics unless specifically indicated otherwise. For example, images that surround or are adjacent to other image(s) may be images that are estimated to be located near the other image(s) along the GIT and/or images that were captured near the capture time of another image, within a certain threshold, e.g., within one or two centimeters, or within one, five, or ten seconds.

The term "Procedure Data" may refer to images and metadata stored on the wearable device and uploaded to the cloud or to a local computer for processing by an engine software.

The term "Compiled Study" or "Study" may refer to and include at least a set of images selected from the images captured by a capsule endoscopy device during a single capsule endoscopy procedure performed with respect to a specific patient and at a specific time, and can optionally include information other than the images as well.

The term "Capsule Endoscopy Report" or "Report" may refer to and include a report generated based on the compiled study for a single capsule endoscopy procedure performed with respect to a specific patient and at a specific time and based on reader input, and may include images, text summarizing the findings and/or recommendation for follow-up based on the compiled study.

The terms "app" or "application" may be used interchangeably and refer to and include software or programs having machine-executable instructions which can be executed by one or more processors to perform various operations.

The term "online processing" may refer to operations which are performed during a CE procedure or prior to the upload of all of the procedure data. In contrast, the term "offline" may refer to operations which are performed after a CE procedure has been completed or after the upload of all of the procedure data.

Referring to FIG. 1, there is shown a diagram of an exemplary remote/cloud computing configuration for CE procedures. The illustrated configuration includes a capsule device 110, a wearable device 120 (such as the illustrated patch), a mobile device (such as the illustrated mobile phone) 130, a remote computing system (such as the illustrated cloud system) 140, and a medical facility 150.

Different capsule devices 110 can be used for different types of CE procedures. For example, different capsule devices 110 may be designed for imaging the small bowel, imaging the colon, imaging the entire GIT, or imaging particular situations, such as imaging a GIT that has Crohn's disease. The terms "capsule" and "capsule device" may be used interchangeably herein. The capsules 110 may include processing capabilities that allow the capsules to prune or discard images, e.g., to prune or discard very similar images. As used herein, "pruning" an image refers to designating or otherwise treating the image as an image that will not be utilized. In various embodiments, pruning an image may include discarding the image, not storing the image, or deleting the image from memory or from a storage, among other possibilities. For example, if a capsule 110 captures images that are essentially identical, processing within the capsule 110 can detect such similarity and decide to communicate only one of the essentially identical images to the wearable device 120. Therefore, a capsule 110 may not communicate all of its images to the wearable device 120. In some embodiments such filtering of similar images may be performed alternatively or additionally in the wearable device 120 or in the mobile device 130. Further aspects of pruning and/or discarding images by the capsule 110 will be described in connection with FIGS. 31-33.

In some embodiments, a capsule may communicate images in a sparse manner, e.g., communicate only each $x^{th}$ captured image (e.g., every second captured image, every fifth or every tenth captured image). A device receiving the communicated images, may process the images to determine a measure of similarity or differentiation between the communicated images. According to some aspects, if two successively communicated images are determined to be different based on such a measure, an instruction may be communicated to the capsule 110 to communicate the images captured between the two images. The receiving device on which such processing may be performed may be, for example, the wearable device 120, the mobile device 130, or the remote computing device (e.g., a cloud system) 140. Such similar image filtering configuration may allow saving in resources and be more cost-effective since it may lead to reduction in communication and processing volumes. Saving in resources is specifically significant for devices which are typically limited in resources, such as the capsule 110 and the wearable device 120.

The wearable device 120 can be a device that is designed to communicate with the capsule device 110 and to receive images of the GIT from the capsule device 110. In aspects of the present disclosure, the wearable device 120 is referred to as a "patch" based on a form factor and light weight similar to a medical patch that can be adhered to patient's skin. The patch is smaller than, for example, a wearable device that must be secured to a patient using a belt. The patch can be a single unitary device (as opposed device with separate parts) that includes an adhesive configured to adhere to a patient's skin, such as to the abdomen. The patch/wearable device 120 can be a single-use disposable device. For example, the patch/wearable device 120 can be non-rechargeable and can have power sufficient for only a single capsule endoscopy procedure. The/wearable device 120 may be then removed and discarded, e.g., by the patient, at the end of the procedure. Although the wearable device 120 is illustrated in FIG. 1 as a patch, the wearable device 120 can be another type of wearable device, e.g., a belt including a data recorder device and plurality of antennas dispersed thereon, 120 and can have other shapes and functionality. For convenience, the wearable device 120 may be referred to herein as "patch," but it will be understood that description herein relating to a patch is applicable to other types of wearable devices as well.

With continuing reference to FIG. 1, the wearable device 120 is secured to the patient and the patient ingests the capsule 110. In the illustrated configuration, the patient carries an Internet-enabled mobile device 130, such as a mobile smartphone device. The mobile device 130 can be a device owned by the patient or can be a device provided to the patient for the CE procedure. In the illustrated embodiment, the wearable device 120 is communicatively coupled with the Internet-enabled mobile device 130. The wearable device 120 receives data from the capsule 110, including images of the patient's GIT captured by the capsule 110, and uploads procedure data 122 to a computing system 140 (e.g., cloud system) via the Internet-enabled mobile device 130 (e.g., through a cellular network). As mentioned above, the term "procedure data" may refer to images and metadata stored on the wearable device 120 which are uploaded to the remote computing system 140 or to a local computing system for processing. Wireless connectivity between the wearable device 120 and the mobile device 130 will be described in connection with FIGS. 6-11.

The remote computing system 140 can be any system that performs computing and can be configured in various ways, including, without limitation, a cloud system/platform, a shared computing system, a server farm, a proprietary system, a networked Intranet system, a centralized system, or a distributed system, among others, or a combination of such systems. For convenience, the remote computing system 140 is illustrated in FIG. 1 as a cloud system. However, all variations of a computing system 140 are contemplated to be within the scope of the present disclosure. The following description will refer to the remote computing system 140 as a cloud system, but it will be understood that description relating to the cloud system is applicable to other variations of a remote computing system.

The cloud system 140 receives and stores the procedure data 122. The cloud system 140 can process and analyze the procedure data 122 using, for example, cloud computing resources, to generate a compiled study 142. As mentioned above, the term "compiled study" may refer to and include at least a set of images selected from the images captured by a capsule endoscopy device during a single capsule endoscopy procedure performed with respect to a specific patient and at a specific time, and can optionally include information other than the images as well. The term "capsule endoscopy report" or "report" may refer to and include a report that is generated based on the compiled study for a single capsule endoscopy procedure performed with respect to a specific patient and at a specific time and based on reader input and based on reader input and may include images, image indications, text summarizing the findings and/or recommendation for follow-up based on the compiled study. In the cloud system 140, the software which processes the procedure data and generates the study may be referred to as "AI engine." The AI engine includes a bundle of algorithms and may include machine learning algorithms, such as deep learning algorithms, and also other types of algorithms. When the remote computing system 140 is not a cloud system, the remote computing system 140 can process and analyze the procedure data using centralized or distributed computing resources, which persons skilled in the art will understand.

A reader 160, typically a healthcare professional, can remotely access the compiled study 142 in the cloud system 140 using a client software application and/or using a browser. The reader 160 reviews and evaluates the compiled study 142 and may create a procedure report via a dedicated reading or viewing application while, e.g., selecting, adding or revising information. A capsule endoscopy (CE) report 144 is generated based on the compiled study 142 and the reader's input via the reading application. The CE report 144 may be then transmitted to the medical facility 150 associated with the CE procedure and may be stored in the medical facility's data systems. In some embodiments, the CE report may become available to a health care provider in the medical facility or to the procedure referring health care provider via a dedicated application. According to some aspects, the read time of a compiled study 142 may be reduced by generating compiled studies which include only a relatively small number of images (e.g., only up to a hundred images per a procedure, up to a few hundreds of images per a procedure or up to an order of a 1,000). This may be enabled, inter alia, by utilizing selection or decision-making methods which provide high sensitivity (e.g., by providing high probability of identifying the images of interest) together with high specificity (e.g., by providing high probability of identifying images which are not of interest) per a procedure. According to some aspects, the compiled study generation may be performed by employing machine learning or specifically deep-learning.

Figure 2:
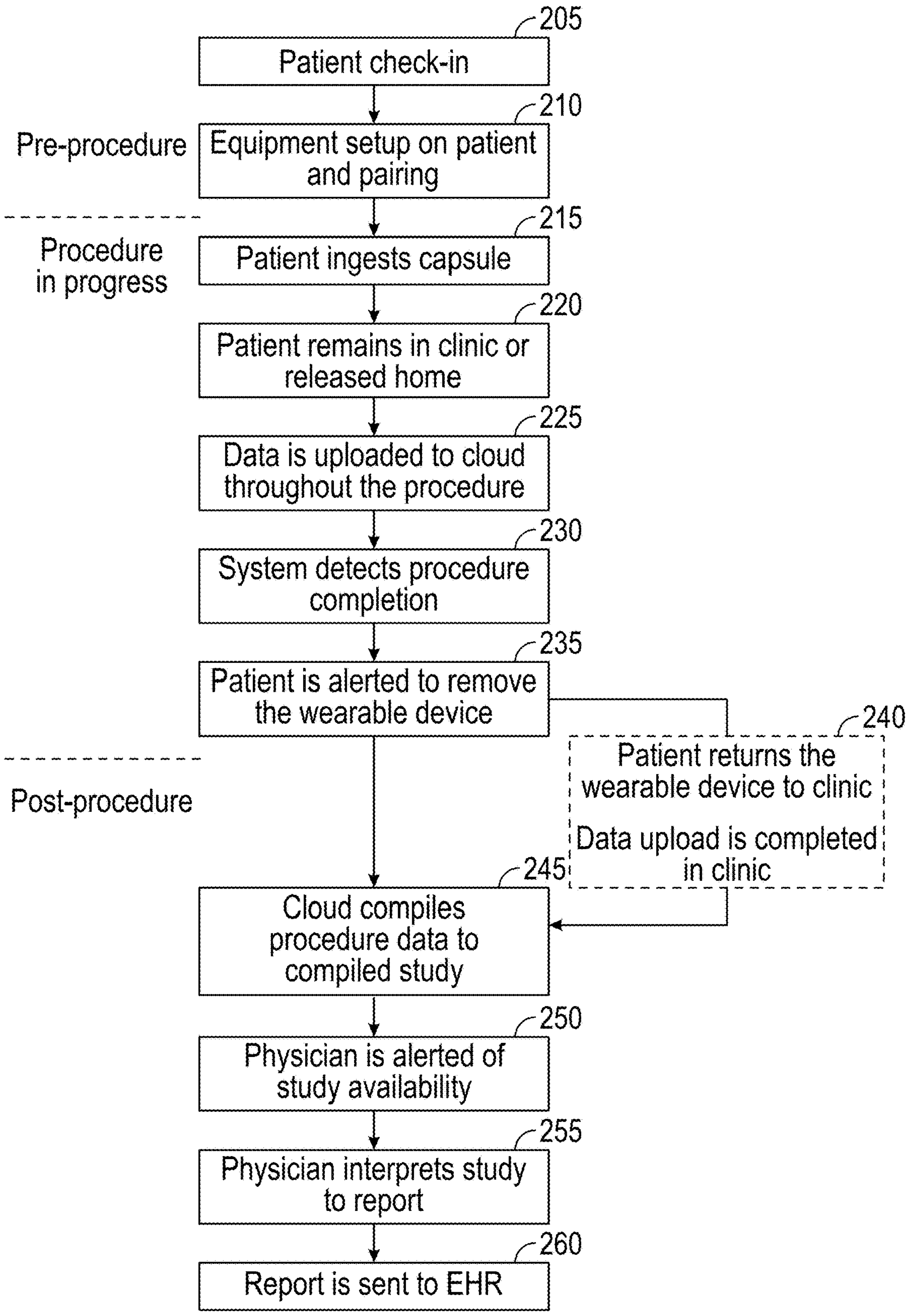
FIG. 2 is a flow diagram of an exemplary CE procedure that uses a remote computing configuration, in accordance with aspects of the disclosure.

FIG. 2 shows a flow diagram of an exemplary CE procedure that uses a remote computing configuration, such as the cloud configuration of FIG. 1. The illustrated procedure includes three phases—a pre-procedure phase, a capsule endoscopy procedure phase, and a post-procedure phase. In the pre-procedure phase, a patient checks in (205) for a capsule endoscopy procedure. In various embodiments, the patient can check in at a medical facility, and in various embodiments, the patient can check in remotely using a patient app, which will be described in more detail later herein. Equipment for the procedure, such as a capsule device and a wearable device, are communicatively paired with each other, and the wearable device is set up on the patient (210). In various embodiments, the capsule and the wearable device can be uniquely bonded with each other during assembly at a factory or warehouse. As used herein, a "unique bond "indicates that a bonded capsule device and a bonded wearable device can communicate with each other, but the bonded capsule device would not be able to communicate with another wearable device, and the bonded wearable device would not be able to communicate with another capsule device. At block 210, the wearable device is also paired with the mobile device (FIG. 1). Wireless connectivity of the devices are addressed in connection with FIGS. 6-11. For now, it is sufficient to note that the mobile device may provide a mobile hotspot which provides Internet connectivity to the wearable device, thereby allowing the wearable device to communicate with the remote computing system. In various configurations, the wearable device may include cellular connectivity, which may enable the wearable device to communicate with the remote computing system without using a mobile device.

In the capsule endoscopy procedure phase, the patient ingests the capsule (215). If the patient is in a medical facility, the patient can either remain there or can be released to go home or go elsewhere (220). During the procedure, the capsule device captures images of the patients GIT. The wearable device receives the data from the capsule device. Using the Internet connectivity provided by the mobile device or using its own cellular connectivity, the wearable device uploads procedure data to a remote computing system, when the Internet connectivity is available (225). If there is no available connection, the procedure data can be stored in an internal storage of the wearable device.

In various embodiments, the wearable device can determine that the capsule endoscopy procedure is completed (230) by, for example, receiving no further data from the capsule, processing the procedure data to detect a completion, and/or other ways. In various embodiments, the remote computing system can determine that the capsule endoscopy procedure is completed (230), which will be discussed in more detail later herein. In various embodiments, a procedure may be "completed" when the capsule has left the GIT portion of interest for the CE procedure even though the capsule is still traversing the patient's GIT. In various embodiments, the procedure may be completed when the capsule has exited the patient's body. When the completion of the CE procedure is detected, the patient is alerted to remove the wearable device (235). In various embodiments, the alert can be provided by the wearable device or by the mobile device or by both. If procedure data on the wearable device was not fully uploaded to the remote computing system because an Internet connection was not available, or for any other reason, the patient can be notified to provide the wearable device to a medical facility where the procedure data can be uploaded from the wearable device to the remote computing system (240).

In the post-procedure phase, the remote computing system processes and analyses the procedure data to generate a compiled study (245). The cloud system alerts one or more healthcare professionals that the compiled study is ready and available (250). The healthcare professional(s) may include a specialist, a referring physician, and/or other medical professionals. A reader reviews the compiled study and may select, add or revise certain information (255). When the review is completed, the computing system generates a report based on the compiled study and the healthcare professional's input. The report is then communicated to and stored in the medical facility's data systems, such as in electronic hospital records (EHR) (255).

The embodiments of FIGS. 1 and 2 are exemplary and variations are contemplated to be within the scope of the present disclosure. For example, in various configurations, the wearable device 120 may include cellular connectivity, which may enable the wearable device to 120 communicate with the remote computing system 140 without using an intermediate mobile device 130. The wearable device 120 may, for example, include, e.g., a cellular modem and a pre-paid SIM card which is recognized and accepted by a cellular network for cellular communications. As another example, the wearable device 120 may connect to a wireless router (not shown) rather than to the patient mobile device 130. In various embodiments, when the patient does not wish to connect the wearable device to an Internet connection, no procedure data is uploaded to the remote computing system during the CE procedure, and upload of the procedure data would be handled as described below in connection with FIGS. 3 and 4. Such variations are contemplated to be within the scope of the present disclosure.

Figure 3:
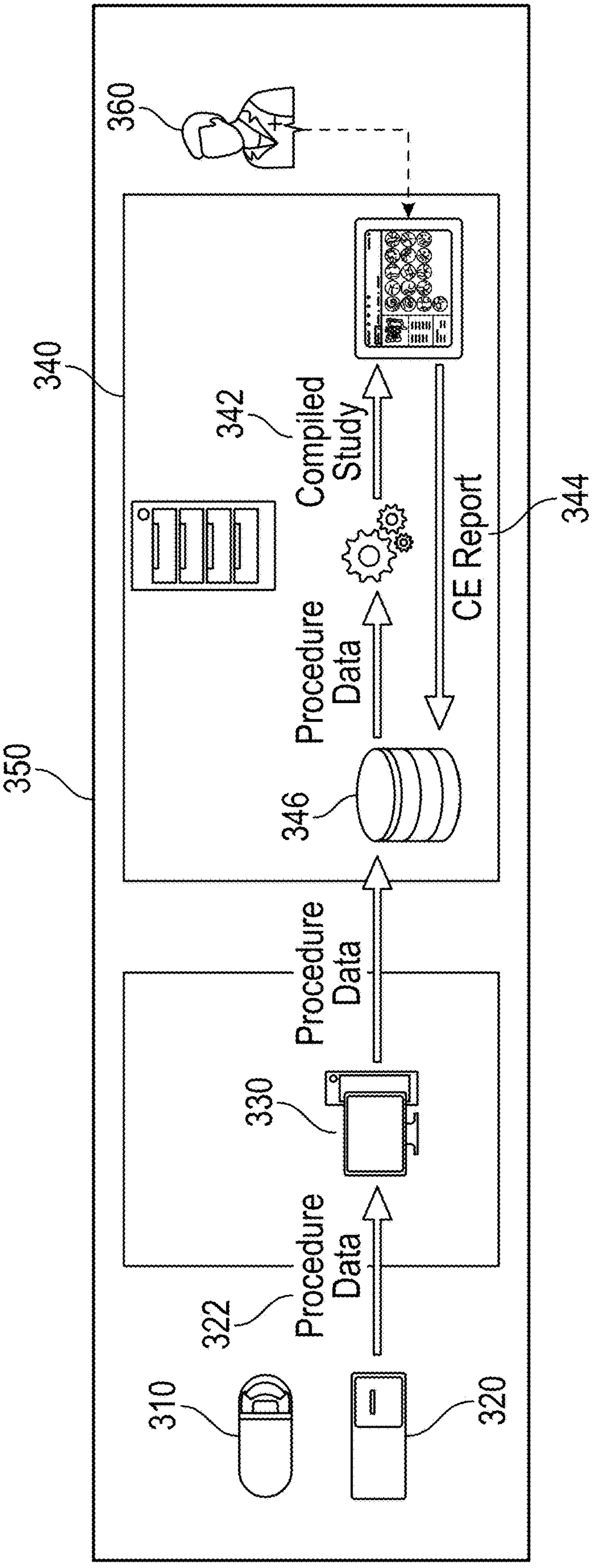
FIG. 3 is a diagram of an exemplary on-premise configuration for CE procedures, in accordance with aspects of the disclosure.

Referring to FIG. 3, there is shown a diagram of an exemplary on-premises configuration for CE procedures. The on-premise configuration can be deployed in cases where, for example, a medical facility 350 does not wish to communicate patient information off-site to a remote computing system. Accordingly, in the on-premise configuration, computing resources, inter alia, for generating a compiled study and a CE report, are located at a medical facility 350. In FIG. 3, the illustrated configuration includes a capsule device 310, a wearable device 320 (such as the illustrated patch), and a medical facility computer, terminal or work station 330, and a computing system 340. The capsule endoscopy procedure can be performed entirely at the medical facility 350 or can be performed partially at the medical facility and partially away from the medical facility. In contrast to the remote/cloud configuration of FIG. 1, the wearable device 320 of the on-premise configuration is not connected to the Internet infrastructure. Therefore, the wearable device 320 stores all procedure data 322 in an internal storage for the entire duration of the CE procedure. When the capsule endoscopy procedure is completed, the patient provides the wearable device 320, or a removable storage of the wearable device 320, to the medical facility 350 and the procedure data 322 is downloaded from the internal storage of the wearable device 320 to a medical facility computer, terminal or work station 330 (e.g., via a USB cable connection) which is connected to the local computing system (e.g., one or more servers). The procedure data is then stored in a local computing system 340 of the medical facility 350.

The computing system 340 then processes and analyzes the procedure data 322 and generates a compiled study 342. In the computing system 340, the software which processes the procedure data and generates the study may be referred to as "AI engine," as explained above. The AI engine includes a bundle of algorithms and may include machine learning algorithms, such as deep learning algorithms and additional algorithms. The AI engine can be installed in the computing system 340 in various ways. In various embodiments, the AI engine can reside in a standalone computer or computing box and can be executed by computing resources of the standalone computer. A reader 360, such as a healthcare professional, can access the compiled study 342 in the computing system 350 using a client software application and/or using a browser. The reader 360 reviews and evaluates the compiled study 342 and may, e.g., select, add or revise certain information. The computing system 340 generates a capsule endoscopy (CE) report 344 based on the compiled study 342 and the reader's input. The CE report 344 is then stored in the medical facility's data systems 346. Accordingly, the procedure data 322 is stored in and is processed by the medical facility's systems after the CE procedure is completed, and the compiled study 342 and CE report 344 are also stored in and processed by the medical facility's systems, without such information being transferred to a remote computing system.

Figure 4:
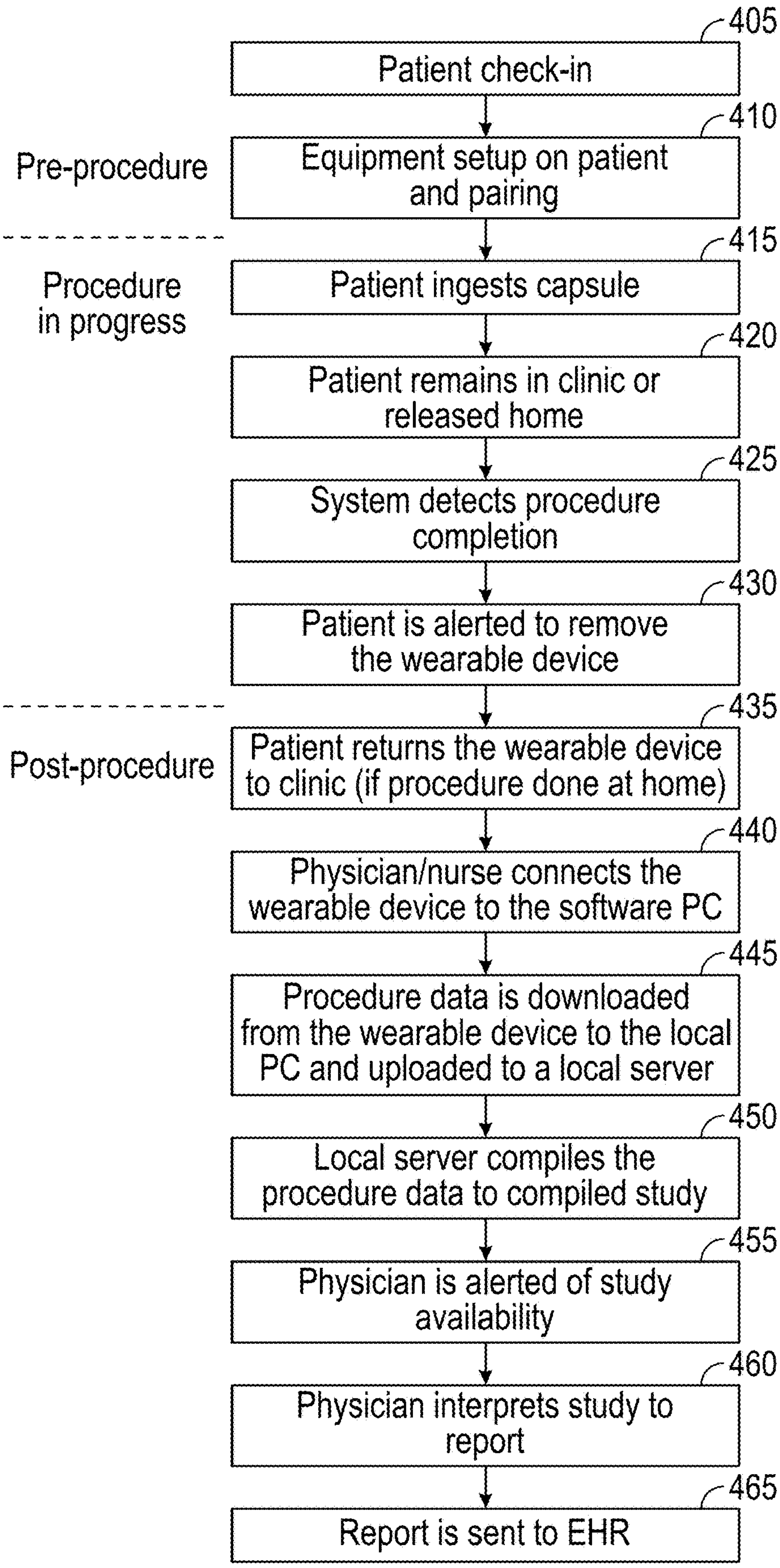
FIG. 4 is a flow diagram of an exemplary CE procedure that uses an on-premise system configuration, in accordance with aspects of the disclosure.

FIG. 4 shows a flow diagram of an exemplary CE procedure that uses an on-premise configuration, such as the on-premise configuration of FIG. 3. The illustrated procedure includes three phases—a pre-procedure phase, a capsule endoscopy procedure phase, and a post-procedure phase. In the pre-procedure phase, a patient checks in (405) for a capsule endoscopy procedure at a medical facility. Equipment for the procedure, such as a capsule device and a wearable device, are communicatively paired with each other, and the wearable device is set up on the patient (410). In various embodiments, the capsule and the wearable device can be uniquely bonded with each other during assembly at a factory or warehouse. In the capsule endoscopy procedure phase, the patient ingests the capsule (415). The patient can either remain at the medical facility or can be released to go home or go elsewhere (420). During the procedure, the wearable device receives data from the capsule device and stores procedure data in an internal storage of the wearable device. The wearable device can determine that the capsule endoscopy procedure is completed (425) by, for example, receiving no further data from the capsule, processing the procedure data to detect a completion, and/or other ways. As mentioned above, a procedure may be "completed" when the capsule has left the GIT portion of interest for the CE procedure even though the capsule is still traversing the patient's GIT. And in various embodiments, the procedure may be completed when the capsule has exited the patient's body. When the procedure completion is detected, the wearable device alerts the patient to remove the wearable device (430). In the post-procedure phase, the patient provides the wearable device, or a removable storage of the wearable device, to the medical facility (435), where the wearable device is connected to a workstation/computer of the medical facility (440). The workstation/computer downloads the procedure data from the wearable device and uploads the procedure data to the local computing system/server of the medical facility (445). The computing system of the medical facility processes and analyses the procedure data to generate a compiled study. (450). The computing system alerts one or more healthcare professionals that the compiled study is available (455). The healthcare professional(s) may include a specialist, a referring physician, and/or other medical professionals. A reader reviews the compiled study and may add or revise certain information. (460). When the review is completed, the computing system of the medical facility generates a procedure report based on the compiled study and the healthcare professional's input. The report is then stored in the medical facility's data systems (465), such as electronic hospital records (EHR). The embodiments of FIGS. 3 and 4 are exemplary and do not limit the scope of the present disclosure. Variations are contemplated to be within the scope of the present disclosure.

Figure 5:
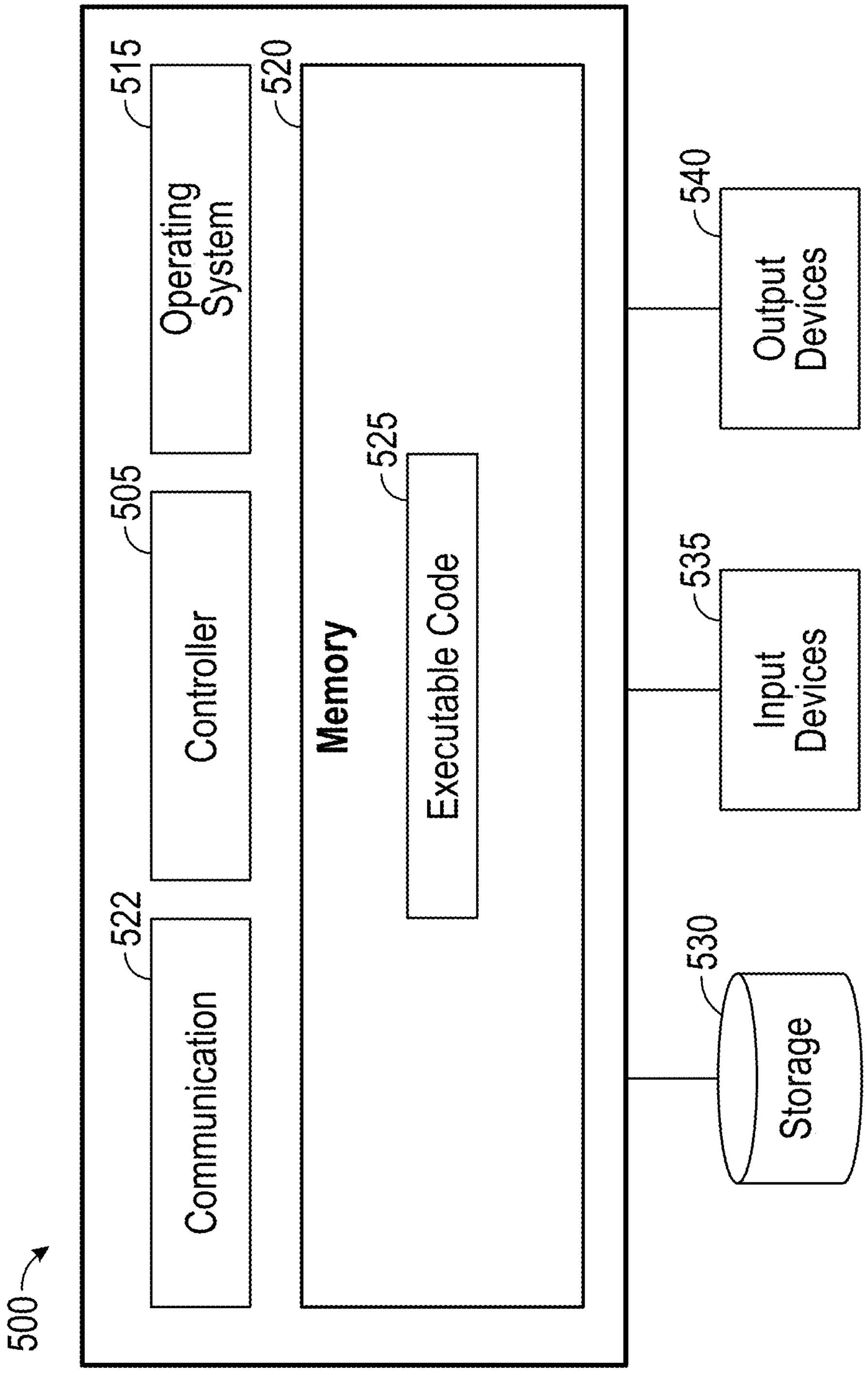
FIG. 5 is a block diagram of an exemplary components of a device or system, in accordance with aspects of the present disclosure.

FIG. 5 shows a block diagram of exemplary components of a system or device 500. The block diagram is provided to illustrate possible implementations of various parts of the disclosed systems and devices. For example, the components of FIG. 5 may implement a patient mobile device (130, FIG. 1), or may implement a portion of a remote computing system (140, FIG. 1), or may implement a healthcare provider device (FIG. 1). The components may also implement a medical facility computer (330, FIG. 3), or may implement a portion of an on-premise computing system (340, FIG. 3). The components may also implement a standalone computer or computing box that contains an AI engine, which is described above. In various embodiments, some components of FIG. 5 may implement a portion of a capsule device (110, FIG. 1).

The computing system 500 includes a processor or controller 505 that may be or include, for example, one or more central processing unit processor(s) (CPU), one or more Graphics Processing Unit(s) (GPU or GPGPU), and/or other types of processor, such as a microprocessor, digital signal processor, microcontroller, programmable logic device (PLD), field programmable gate array (FPGA), or any suitable computing or computational device. The computing system 500 also includes an operating system 515, a memory 520, a storage 530, input devices 535, output devices 540, and a communication device 522. The communication device 522 may include one or more transceivers which allow communications with remote or external devices and may implement communications standards and protocols, such as cellular communications (e.g. 3G, 4G, 5G, CDMA, GSM), Ethernet, Wi-Fi, Bluetooth, low energy Bluetooth, Zigbee, Internet-of-Things protocols (such as mosquitto MQTT), and/or USB, among others.

The operating system 515 may be or may include any code designed and/or configured to perform tasks involving coordination, scheduling, arbitration, supervising, controlling or otherwise managing operation of computing system 500, such as scheduling execution of programs. The memory 520 may be or may include, for example, one or more Random Access Memory (RAM), read-only memory (ROM), flash memory, volatile memory, non-volatile memory, cache memory, and/or other memory devices. The memory 520 may store, for example, executable instructions that carry out an operation (e.g., executable code 525) and/or data. Executable code 525 may be any executable code, e.g., an app/application, a program, a process, task or script. Executable code 525 may be executed by controller 505.

The storage 530 may be or may include, for example, one or more of a hard disk drive, a solid state drive, an optical disc drive (such as DVD or Blu-Ray), a USB drive or other removable storage device, and/or other types of storage devices. Data such as instructions, code, procedure data, and medical images, among other things, may be stored in storage 530 and may be loaded from storage 530 into memory 520 where it may be processed by controller 505. The input devices 535 may include, for example, a mouse, a keyboard, a touch screen or pad, or another type of input device. The output devices 540 may include one or more monitors, screens, displays, speakers and/or other types of output devices.

The illustrated components of FIG. 5 are exemplary and variations are contemplated to be within the scope of the present disclosure. For example, the numbers of components may be greater or fewer than as described and the types of components may be different than as described. When the system 500 implements a machine learning system, for example, a large number of graphics processing units may be utilized. When the computing system 500 implements a data storage system, a large number of storages may be utilized. As another example, when the computing system 500 implements a server system, a large number of central processing units or cores may be utilized. Some components of FIG. 5 (e.g., communication 522, controller 505, memory 520, executable code/instructions 525) may implement a portion of a capsule device (110, FIG. 1). Other variations and applications are contemplated to be within the scope of the present disclosure.

The description above described various systems and methods for capsule endoscopy procedures. Communication capabilities between various components of the described systems are described below in connection with FIGS. 6-11. Software apps which utilize and/or rely on such communication capabilities will be described in connection with FIGS. 12-25.

Figure 6:
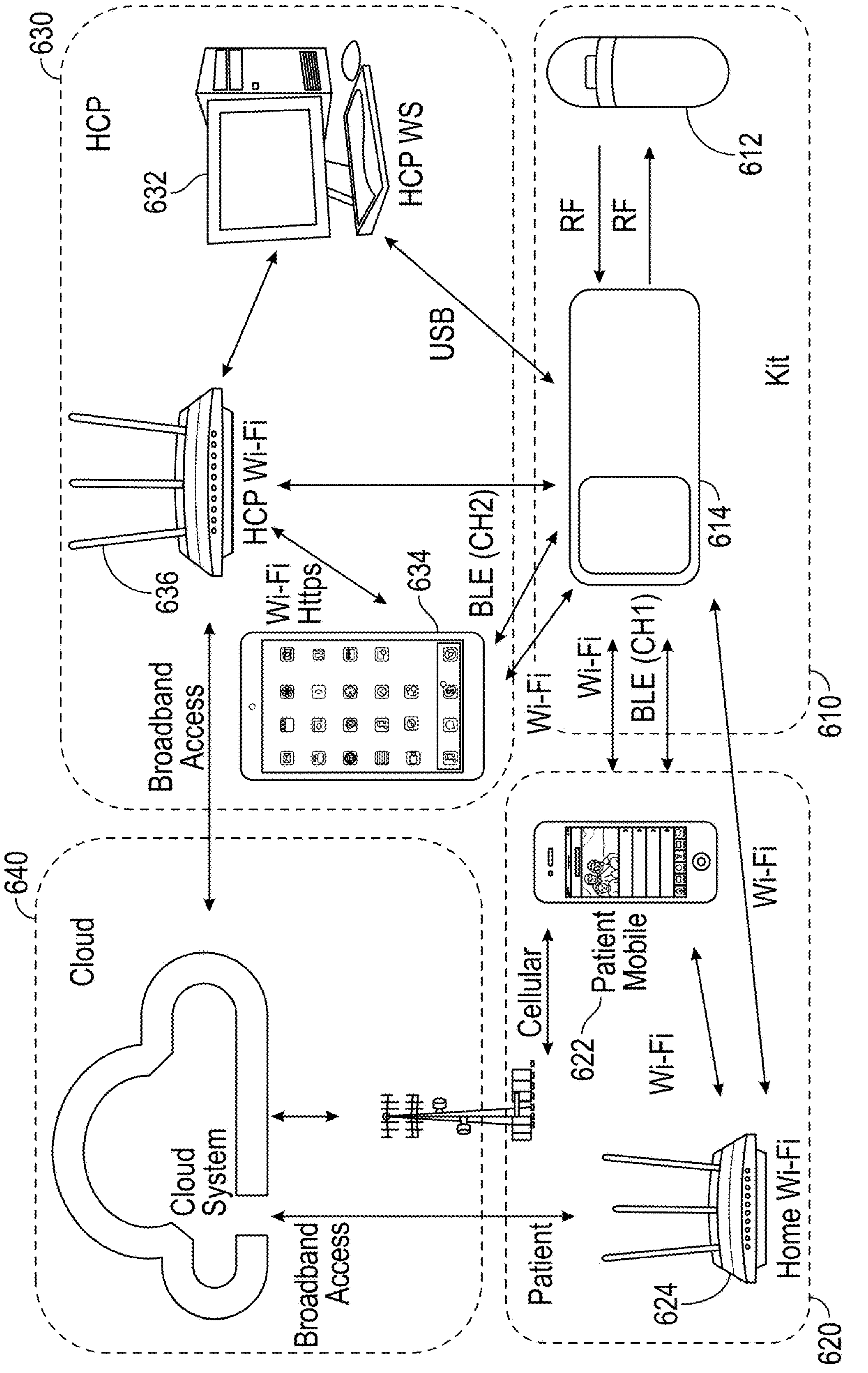
FIG. 6 is a diagram of exemplary devices and systems and communications between the devices and systems, in accordance with aspects of the present disclosure.

Referring to FIG. 6, there is a diagram of various devices and systems of a remote computing configuration and communications between the devices and systems. The systems include a capsule endoscopy kit 610 that includes a capsule device 612 and a wearable device 614, a patient system 620 that includes an Internet-enabled mobile device 622 and/or a wireless router 624, a healthcare provider system 630 that includes a computer/workstation 632, a tablet device 634, and/or a wireless router 636, and a remote computing system 640. For convenience, the remote computing system 640 is illustrated as a cloud system and may be referred to as a cloud system. However, it will be understood that the description below relating to the cloud system shall apply to other variations of a remote computing system.

In the capsule endoscopy kit 610, the capsule device 612 and the wearable device 614 can communicate with each other using radio frequency (RF) transceivers. Persons skilled in the art will understand how to implement RF transceivers and associated electronics for interfacing with RF transceivers. In various embodiments, the RF transceivers can be designed to use frequencies that experience less interference or no interference from common communications devices, such as cordless phones, for example. The wearable device 614 can include various communication capabilities, including Wi-Fi, low energy Bluetooth (BLE), and/or a USB connection. The term Wi-Fi includes Wireless LAN (WLAN), which is specified by IEEE 802.11 family of standards. The Wi-Fi connection allows the wearable device 614 to upload procedure data to the cloud system 640. The wearable device 614 can connect to a Wi-Fi network in either a patient's network system 620 or a healthcare provider's network system 630, and the procedure data is then transferred to the cloud system 640 through the Internet infrastructure. The wearable device 614 is also equipped with a wired USB channel for transferring procedure data when a Wi-Fi connection is not available or when procedure data could not all be communicated using Wi-Fi. The Bluetooth® low energy (BLE) connection is used for control and messaging. Because the BLE connection uses relatively low power, BLE can be continuously-on during the entire procedure and is suited for control messaging. Depending on the device and its BLE implementation, the BLE connection may support communications rates of about 250 Kbps-270 Kbps through about 1 Mbps. While some BLE implementations may support somewhat higher communication rates, a Wi-Fi connection is generally capable of providing much higher communication rates. Therefore, a Wi-Fi connection will generally be used for transferring procedure data to the cloud system 640, which may be transferred at transfer rates of 10 Mbps or higher, depending on the connection quality and amount of procedure data. In various embodiments, when the amount of procedure data to be transferred is suitable for the BLE connection transfer rate, the procedure data can be transferred using the BLE connection.

As shown in FIG. 6, there are many possible communication paths between a wearable device 614 and the cloud system 640 or various devices. FIGS. 7-11 address connectivity between particular portions of FIG. 6, and they are described below. The illustrated and described embodiments are merely exemplary and other types of connections not shown or described can be used, such as Zigbee or Internet-of-Things protocols, among others.

Figure 7:
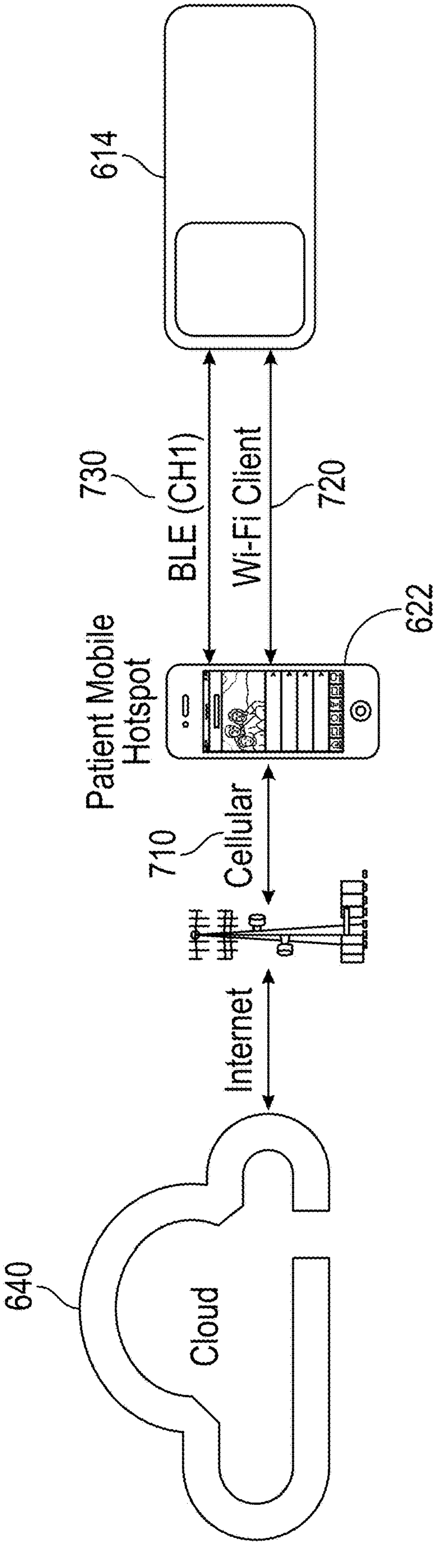
FIG. 7 is a diagram of an exemplary communication path between a wearable device and a cloud system via a mobile hotspot, in accordance with aspects of the disclosure.

With reference to FIG. 7, there is shown a diagram of an exemplary communication path between a wearable device 614 and a cloud system 640 via tethering or mobile hotspot provided by a patient Internet-connected mobile device 622. The patient Internet-connected mobile device 622 may be referred to herein as a mobile device 622 and can include, without limitation, a smartphone, a laptop, or a tablet, among others. The mobile device 622 can be any mobile device used by a patient, including a mobile device owned by the patient or a mobile device loaned to the patient for the CE procedure. For convenience, a smartphone is illustrated in FIG. 7, but it is intended for the disclosure to apply to other types of Internet-connected mobile devices as well. By providing tethering or a mobile hotspot, the mobile device 622 can share its cellular Internet-connection 710 with the wearable device 614 through a Wi-Fi connection 720. When providing a mobile hotspot, the mobile device 622 behaves as a router and provides a gateway to the cloud system 620. Because a mobile hotspot Wi-Fi connection 720 can become disconnected due to inactivity (e.g., ninety seconds of no activity), the wearable device 614 can be configured to ping the mobile device 622 regularly to keep the mobile hotspot Wi-Fi connection 720 active. Otherwise, if the mobile hotspot Wi-Fi connection 720 is allowed to become inactive, the patient would need to go through a re-confirmation process to reestablish the hotspot connection due to security reasons, which may be a nuisance to the patient and make the upload unreliable. Also, as mentioned above, the mobile device 622 and the wearable device 614 are capable of a Bluetooth® low energy (BLE) connection 730 for communicating control messages. In various embodiments, the BLE connection 730 may be used to communicate procedure data when suitable.

A patient software app can be used to set up the Wi-Fi connection 720 between the wearable device 614 and the mobile hotspot of the patient mobile device 622. The patient app will be described later herein. Using a mobile hotspot, the wearable device 614 can communicate directly to a given Internet address or, alternatively, can connect to a subnet client (e.g., default gateway address). An advantage of direct connection is that the mobile device 622 transfers the procedure data transparently to the cloud system 640 and there is no need for internal buffers, but a potential disadvantage is that data transfer speed between the wearable device 614 and the mobile device 622 may vary depending on the upstream Internet connection quality, such as cellular signal strength 710. When the wearable device 614 connects to a mobile local subnet (default gateway), the wearable device 614 transfers the procedure data to a local buffer of the mobile device 622, and upload of the procedure data from this buffer to the cloud system 640 is handled by another thread in parallel. In this case, data transfer speed between the wearable device 614 and the mobile device 622 can advantageously utilize the full bandwidth of the Wi-Fi connection 720 regardless of the Internet connection quality 710, but a potential disadvantage is that the internal buffer of the mobile device 622 can exposed the procedure data to security threats. FIG. 7 is exemplary and variations are contemplated to be within the scope of the present disclosure. For example, rather than using a cellular Internet connection 710, a mobile device 622 can share broadband Internet connectivity with the wearable device instead (not shown). Such and other variations are contemplated to be within the scope of the present disclosure.

Figure 8:
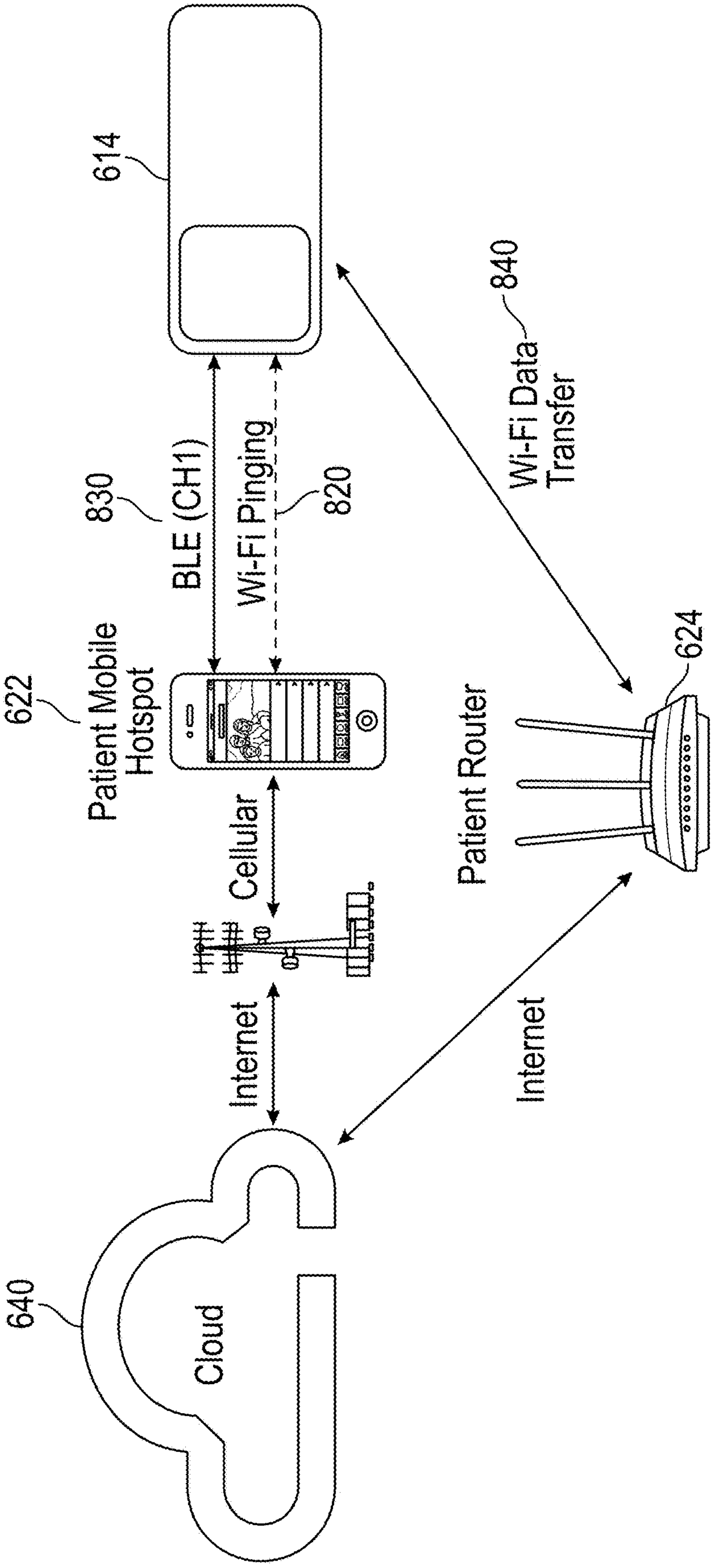
FIG. 8 is a diagram of an exemplary communication paths between a wearable device and a cloud system, in accordance with aspects of the disclosure.

FIG. 8 shows a diagram of an exemplary communication path between a wearable device 614 and a cloud system 640 via a communication device such as a router 624. When it is suitable for the wearable device 614 to directly use a Wi-Fi network 840 (e.g., a home network), the patient can manually specify the Wi-Fi access credentials to the wearable device 614 using a patient software app in the patient mobile device 622. The Wi-Fi access credentials can be communicated by the mobile device 622 to the wearable device 614 using the BLE connection 830. Whenever the Wi-Fi network 840 is in range of the wearable device 614, the wearable device 614 can connect to the Wi-Fi network 840 and upload the procedure data via the communication device/router 624. In various embodiments, the wearable device 614 can choose to simultaneously maintain a mobile hotspot Wi-Fi connection 820 and a router Wi-Fi connection 840 by pinging the mobile device regularly through the mobile hotspot Wi-Fi connection 820, such as once every sixty seconds. If the wearable device 614 does not regularly ping the mobile device 622, the mobile hotspot Wi-Fi connection 820 may become inactive to preserve power.

Figure 9:
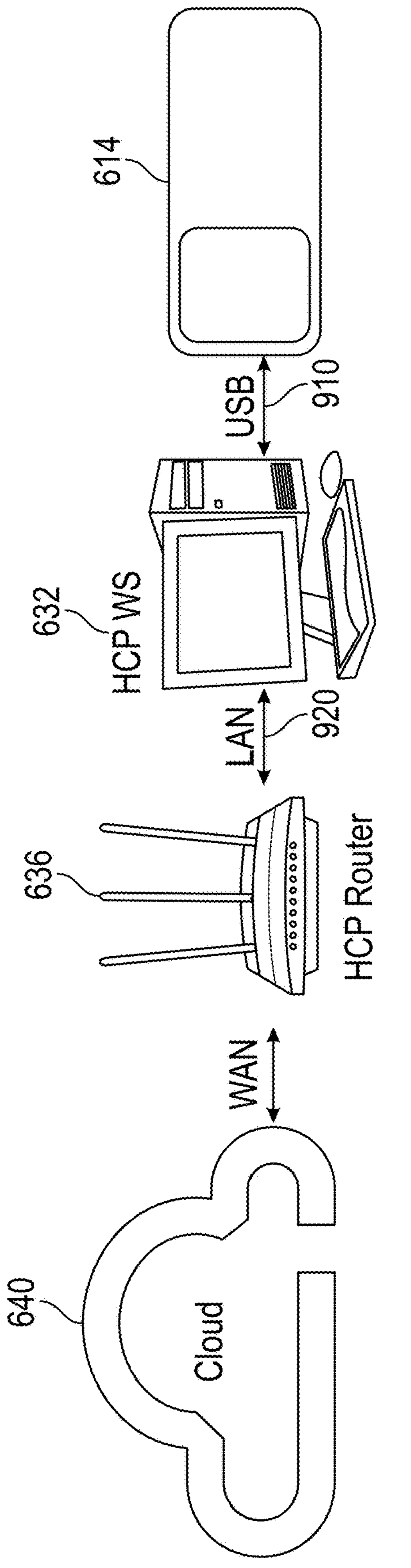
FIG. 9 is a diagram of an exemplary communication path between a wearable device and a cloud system via a healthcare provider workstation and router, in accordance with aspects of the disclosure.

FIG. 9 shows a diagram of an exemplary communication path between a wearable device 614 and a cloud system 640 via a healthcare provider workstation 632. The illustrated communication path can be used whenever procedure data in the internal storage of the wearable device 614 was not uploaded or not fully uploaded to the cloud system 640. The patient can provide the wearable device 614, or a removable storage of the wearable device 614, to the medical facility, and personnel at the facility can connect the wearable device 614 or the removable storage to a workstation 632 via a USB connection 910. The procedure data is transferred from the wearable device 614 to the workstation 632, and then the workstation 632 transfers the procedure data to the cloud system 640 using the facility's network infrastructure, such as a router 636 and local area network 920. A software application on the workstation 632 can coordinate the upload of procedure data to the cloud system 640. Such a software application can use secured authentication and AES data encryption for data transfer by the USB connection 910. Additionally, the procedure data can be transferred from the wearable device 614 to the workstation 632 using data integrity control, such as TCP/IP protocol over USB, for example. FIG. 9 is exemplary and does not limit the scope of the present disclosure. For example, in various embodiments, the healthcare provider workstation 632 can be a laptop computer or another device. Such variations are contemplated to be within the scope of the present disclosure.

Figure 10:
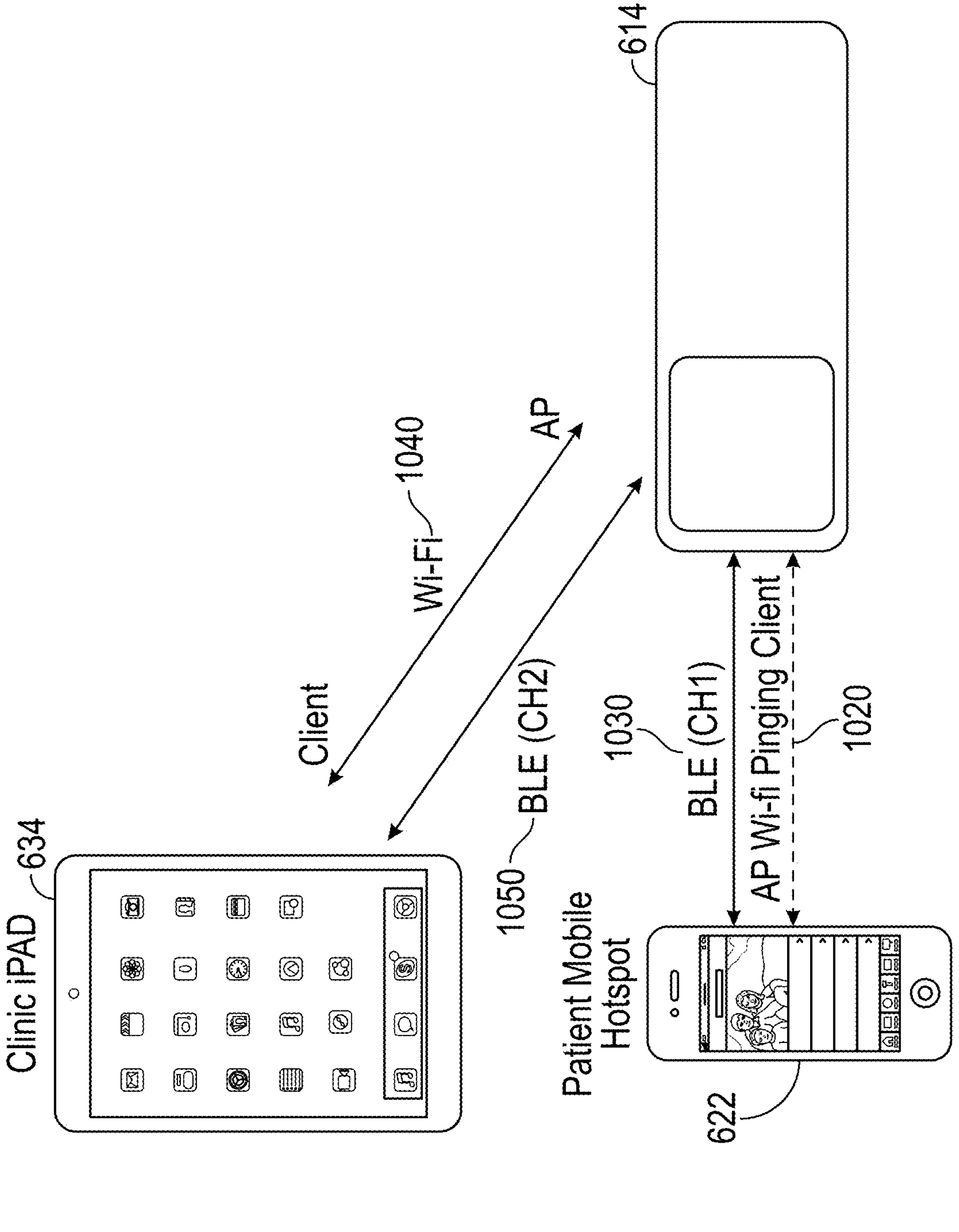
FIG. 10 is a diagram of exemplary connections between a wearable device and various devices, in accordance with aspects of the disclosure.

FIG. 10 shows a diagram of an exemplary direct connection between a wearable device 614 and a healthcare provider device 634. In accordance with aspects of the present disclosure, the wearable device 614 can function as an access point (AP) that can connect with a tablet or smartphone via Wi-Fi. By default, the wearable device 614 is set as a station (client) and periodically connects to a mobile hotspot 1020 or other Wi-Fi connection for data uploading. Whenever the wearable device 614 receives a predetermined request, such as a "real-time view" request described later herein, the wearable device 614 changes its Wi-Fi setup from station to AP and permits a healthcare provider device 634 to establish a Wi-Fi connection 1040 to the wearable device 614, which functions as an access point. In this manner, the wearable device 614 advertises as client and scanning as master to establish Wi-Fi connections. In summary, "real-time view" enables a healthcare provider device 634 to receive an immediate snapshot of recent procedure data by locally/directly connecting to the wearable device 614. This functionality may be available during a capsule endoscopy procedure when the patient is in a medical facility.

In the illustrated configuration, the connections between the wearable device 614 and the patient mobile device 622 include a BLE connection (CH1) 1030 for control and massaging and a Wi-Fi connection 1020 for data upload (Client/hotspot). The connections between the wearable device 614 and the healthcare provider device 634 include a BLE connection (CH2) 1050 for the healthcare provider device 634 to control the "real-time view" functionality and a Wi-Fi connection 1040 for "real-time view" data transfer from AP to client. The wearable device 614 can ping the mobile device BLE connection (CH1) 1030 every sixty seconds (or another time interval) to verify that the mobile device 622 is active and in range. If the mobile device 622 is detected as located too far away based on the ping of the BLE connection 1030, the wearable device 614 can provide an alert to the patient before the connection 1030 is lost (e.g., beep alerts).

Generally, the wearable device 614 operates as a Wi-Fi client to upload procedure data to the cloud system 640. The wearable device 614 can expose the BLE channel (CH2) 1050 constantly or regularly to check for a "real-time view" request. In case such a request is received, the wearable device 614 can establish a TLS1.2 (or higher) secured TCP/IP connection before data transmission. In various embodiments, the wearable device 614 may keep the Wi-Fi connection 1040 active for a period of time, such as sixty seconds, and then terminate the Wi-Fi connection 1040. The "real-time view" request may be re-established. However, the wearable device 614 also operates to ping the mobile hotspot Wi-Fi connection 1020 of the mobile device every sixty seconds (or another time interval) to keep the mobile hotspot Wi-Fi connective 1020 active, so that the mobile hotspot connection 1020 is not shut down due to inactivity. The wearable device 614 may not upload procedure data to the cloud system 640 while the "real time view" request is ongoing, such that upload of procedure data by the wearable device 614 to the cloud system 640 is delayed until the "real time view" request ends.

FIG. 10 and the described embodiments are exemplary and variations are contemplated to be within the scope of the present disclosure. In various embodiment, requests other than "real-time view" may cause the wearable device 614 to switch from station/client mode to AP mode. In various embodiments, the healthcare provider device 634 may not be a tablet and can be another type of device, such as a smartphone, laptop, or desktop computer, for example. Such variations are contemplated to be within the scope of the present disclosure.

Figure 11:
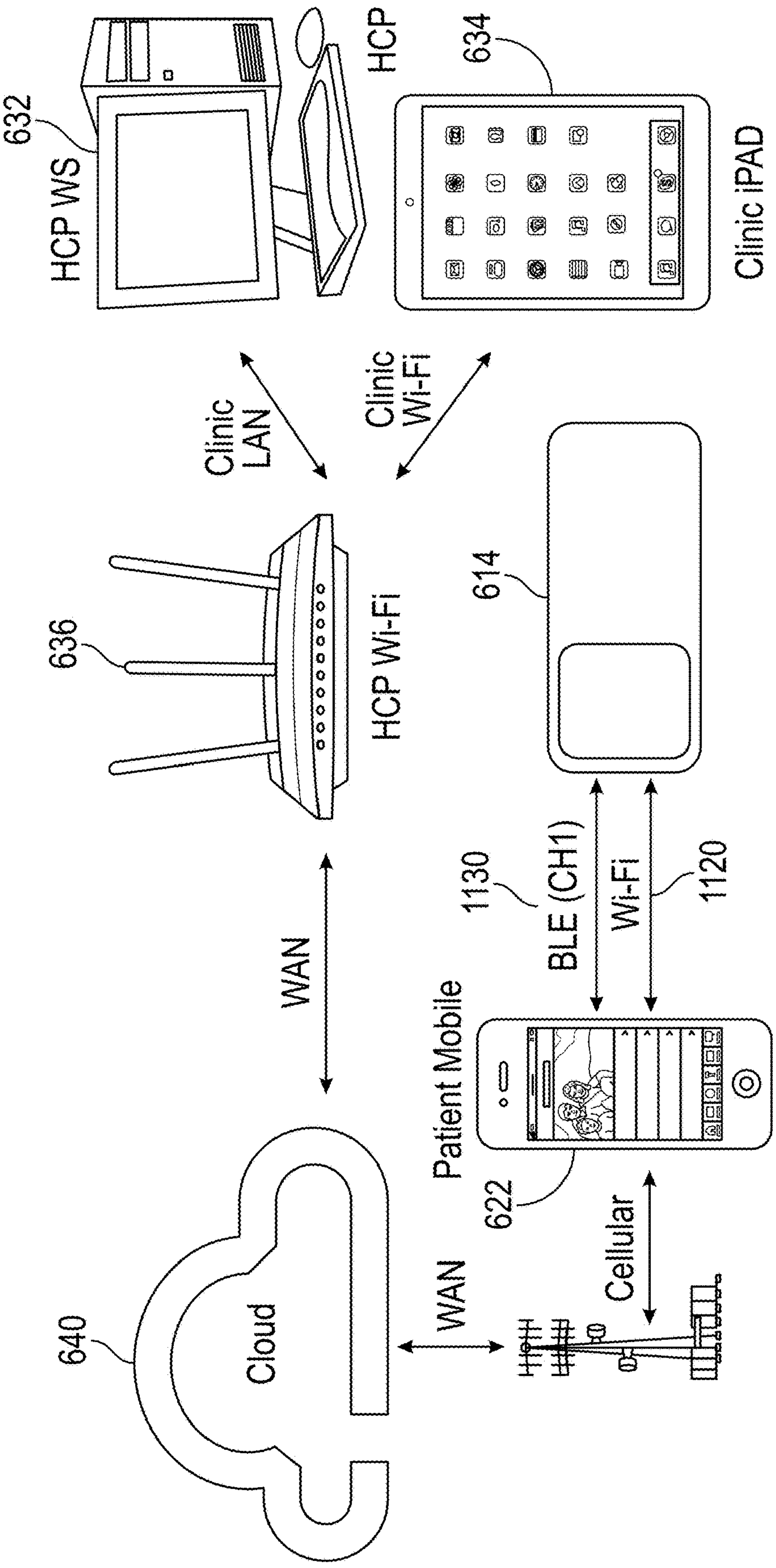
FIG. 11 is a diagram of exemplary communication paths between a wearable device and healthcare provider devices, in accordance with aspects of the disclosure.

FIG. 11 shows a diagram of exemplary communication paths between a wearable device 614 and healthcare provider devices 632, 634. The communication path between the wearable device 614 and the cloud system 640 is the same as that described above in connection with FIG. 7 or can be the same as that illustrated in FIG. 8. The communication path between the healthcare provider devices 632, 634 and the cloud system 640 is a usual connection through a network infrastructure, such as a router 636. In accordance with aspects of the present disclosure, the healthcare provider (HCP) devices 632, 634 can include a software app referred to herein as an HCP app, which can initiate a command for the wearable device 614, which will be referred to as a "near real-time view" command. The HCP app will be described in more detail later herein, including a "remote view" feature that is separate from the "near real-time view" feature. For now, it is sufficient to note that the near real-time view command can be conveyed through the healthcare provider network infrastructure to the cloud system 640, which may send a corresponding command to the wearable device 614 through the Wi-Fi connection 1120 or the BLE connection 1130 of the patient mobile device 622. In various embodiments, the command from the cloud system 640 can be an instruction for the wearable device 614 to immediately upload the most recent procedure data which has not yet been uploaded to the cloud system 640. In various embodiments, in response to the command from the healthcare provider device 632, 634, the cloud system 640 can check the timestamp of the most-recent procedure data upload. If the duration since the last upload exceeds a predetermined threshold, the cloud system 640 can communicate an upload command to the patient mobile device 622 to trigger a procedure data upload. The patient mobile device 622 can then signal the wearable device 614 via the Wi-Fi connection 1120 or via the BLE connection (CH1) 1130 to provide a procedure data upload. In response, the wearable device 614 initiates a transfer of procedure data using the Wi-Fi connection 1120. The cloud system 640 receives the procedure data upload and communicates the procedure data to the healthcare provider device 632, 634 so that a healthcare professional can review the latest procedure data in near real-time. Accordingly, this functionality, and its corresponding command, are referred to herein as "near real-time view" and will be described in more detail later herein.

Accordingly, the description above described, with reference to FIGS. 6-11, various devices and connections and communications between the devices. Persons skilled in the art will understand how to implement the various communication connections, including the Wi-Fi, Bluetooth, and USB connections, among others.

Figure 12:
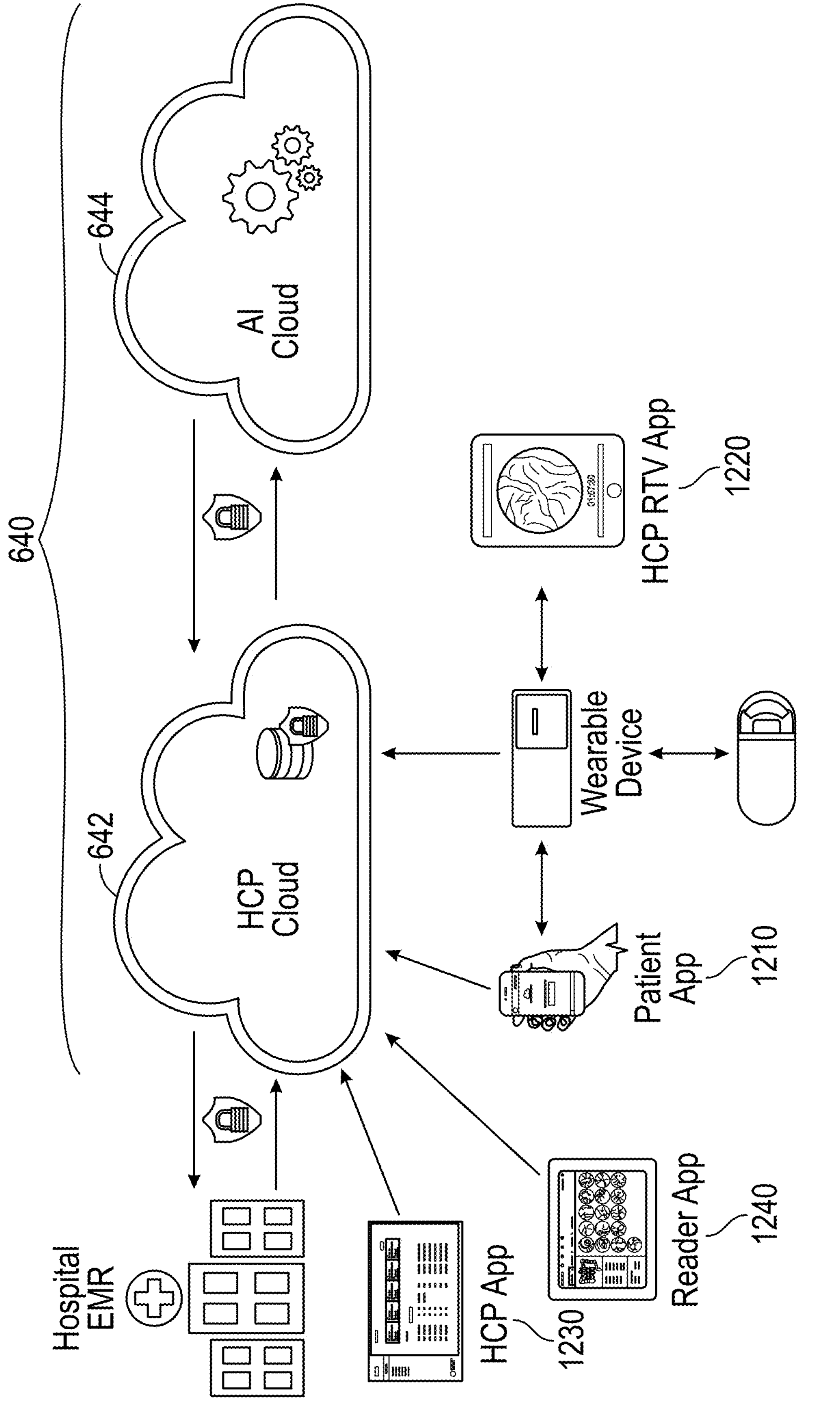
FIG. 12 is a diagram of exemplary software apps, in accordance with aspects of the present disclosure.

As mentioned above, various software apps/applications can run on the devices. FIG. 12 shows a diagram of the exemplary software apps, including a patient app 1210 on a patient mobile device, a healthcare provider "real-time view" app 1220, a healthcare provider app 1230 that includes "near real-time" functionality and "remote view" functionality, and a reader app 1240 that allows a reader to view a compiled study, provide input and generate a report. In various embodiments, the apps 1210-1240 can be downloaded from an app store or can be downloaded from another source, such as from a website of the capsule endoscopy kit provider. The apps 1210-1240 can be configured to be operable in different operating systems, such as iOS, Android, Chrome OS, and/or Windows, among others. Although various apps arc illustrated as separate apps in FIG. 12, various apps can be combined into a single app having various features or can be combined to a different number of apps. Such variations are contemplated to be within the scope of the present disclosure.

The patient app 1210, the reader app 1240, and the healthcare provider app 1230 can communicate with the cloud system 640. In the illustrated configuration, such apps, 1210, 1230 and 1240, communicate with a portion of the cloud system 640 configured to receive and present data, which is designated as the HCP cloud 642. Another portion of the cloud system 640, designated as the AI cloud 644, is a data processing and machine learning sub-system that performs processing of procedure data and generates data to be presented by the HCP cloud 642. Thus, the AI cloud can perform machine learning but can also perform non-AI processing and tasks. The AI cloud 644 can perform operations that generate a compiled study. In the AI cloud 644, the software which processes the procedure data and generates the study may be referred to as "AI engine." The AI engine includes a bundle of algorithms and may include machine learning algorithms, such as deep learning algorithms and algorithms of other types. The AI cloud 644 can apply various algorithms and automated decision systems, including deep learning or other machine learning operations and techniques. The separation of the cloud system 640 into two sub-systems provides isolation of the AI cloud 644, such that the AI cloud 644 may only be accessed by the HCP cloud 642 and there is no direct connection between any of the applications used by end-users and the AI cloud 644. Such configuration may better protect the AI cloud from malicious actions or unauthorized access. However, use of two sub-systems is illustrative and is not intended to limit the scope of the present disclosure. Other types and/or numbers of sub-systems in a cloud system 640 are within the scope of the present disclosure. Persons skilled in the art will recognize how to implement the cloud system 640, including by way of cloud services platforms.

As mentioned above, the term "online processing" may refer to processing performed on a remote computing system (e.g., AI cloud 644) during the procedure or prior to the upload of all of the procedure data (i.e., complete upload of procedure data) and with respect to only a portion of the procedure data. Based on such online processing, online detection of, e.g., pathologies of interest or anatomical structures, may be provided. According to some aspects, the online detection may be performed with respect to batches of images uploaded to the cloud system 640. For example, fresh bleeding, strictures, capsule retention or passage to another anatomical portion of the GIT, may be online detected. A referring physician or a healthcare provider supervising the procedure may be notified in real-time of suspected findings such as fresh bleeding or stricture, which may require immediate treatment. Identification of anatomical structures, portions or landmarks (e.g., cecum or the pyloric valve) may be used, for example, for localization of the capsule. According to some aspects, the uploaded images may be processed online to determine a prediction, e.g. with respect to the capsule transfer time, velocity or motility. Such prediction, for example, may be used to change the capsule capture frame rate.

Each app/application will now be described below.

The patient app is configured to provide display screens to guide a patient through preparing for a capsule endoscopy procedure and though undergoing the procedure. In addition, the patient app provides patient information to the cloud system and also allows the patient to set up uploading of procedure data from the wearable device to the cloud system. The patient app may be installed on a mobile device carried by a patient before the CE procedure commences. In various embodiments, the mobile device may be a dedicated device provided to the patient by a medical facility for the CE procedure or may be a mobile device owned by the patient, such as the personal mobile phone of the patient.

Figure 13:
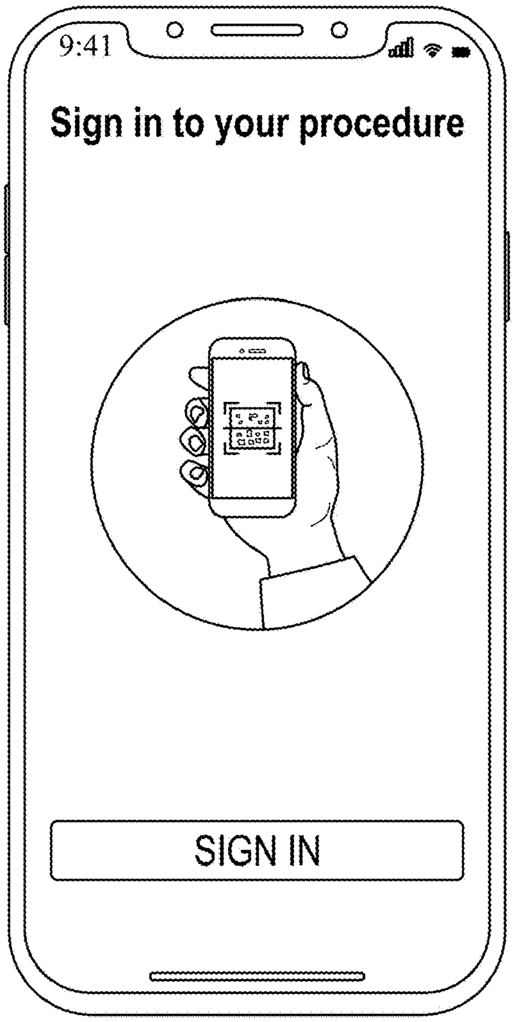
FIG. 13 is an exemplary instruction screen of a patient app for signing into a capsule endoscopy procedure, in accordance with aspects of the present disclosure.
Figure 14:
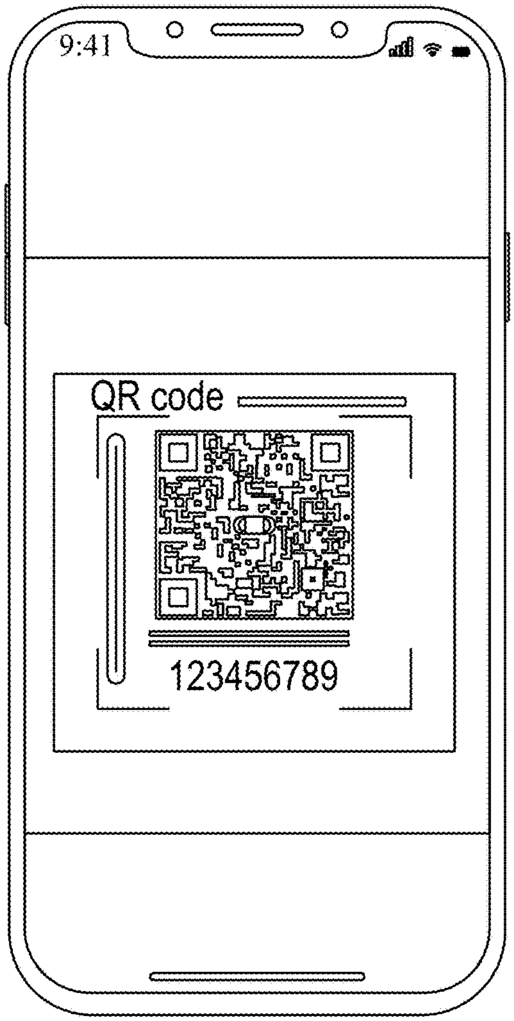
FIG. 14 is an exemplary screen of a patient app for scanning a QR code, in accordance with aspects of the present disclosure.

Referring to FIG. 13, there is shown an exemplary sign-in screen of the patient app. Before a patient signs in for a capsule endoscopy procedure using the patient app, the patient generally has consulted a healthcare provider and medical facility and has been provided with patient instructions, such as a paper of patient instructions. The patient instructions may contain instructions for how to download a patient app and sign in to the capsule endoscopy procedure using the patient app. As used herein, signing into a procedure does not mean starting a procedure. Rather, the term "sign in" refers to logging into an account. In various embodiments, a patient can sign in to an upcoming procedure to obtain more detailed information about preparing for the upcoming procedure. In various embodiments, a patient can sign in for the procedure at a medical facility or at another location, such as at home. The illustrated sign-in screen of a patient app operates to scan a QR code that is provide in a healthcare provider's patient instructions (e.g., printed on paper of patient instructions), but other ways of signing in for a procedure are contemplated to be within the scope of the present disclosure. For example, in various embodiments, a patient can sign-in for a procedure by manually entering an alphanumeric code, or by selecting a link in an e-mail or text message. Other ways of signing in are within the scope of the present disclosure. FIG. 14 shows an example of a QR code being scanned by a patient mobile device to sign in to a capsule endoscopy procedure. As mentioned above, the QR code can be provided by a healthcare provider in the patient instructions, such as a QR code printed on a paper of patient instructions.

In accordance with aspects of the present disclosure, a regimen may be identified in a QR code. A healthcare professional can select a regimen for a CE procedure for a patient, and the regimen can be identified in the QR code that is provided/printed in the patient instructions provided to the patient, as mentioned above. The QR code can be generated based on the regimen selected by a physician and based on other information, and the QR code can be printed in the patient instructions. An example of a regimen is shown in the patient app screen of FIG. 15, which is a screen that is displayed after a patient has signed in. The scanned QR code causes the patient app to retrieve the regimen selected by the healthcare professional, which includes acquiring medications by a particular date 1510, starting a clear liquid diet by another date 1520, and starting the procedure by a scheduled date 1530. The patient app displays the regimen and dates on the display screen.

Figure 15:
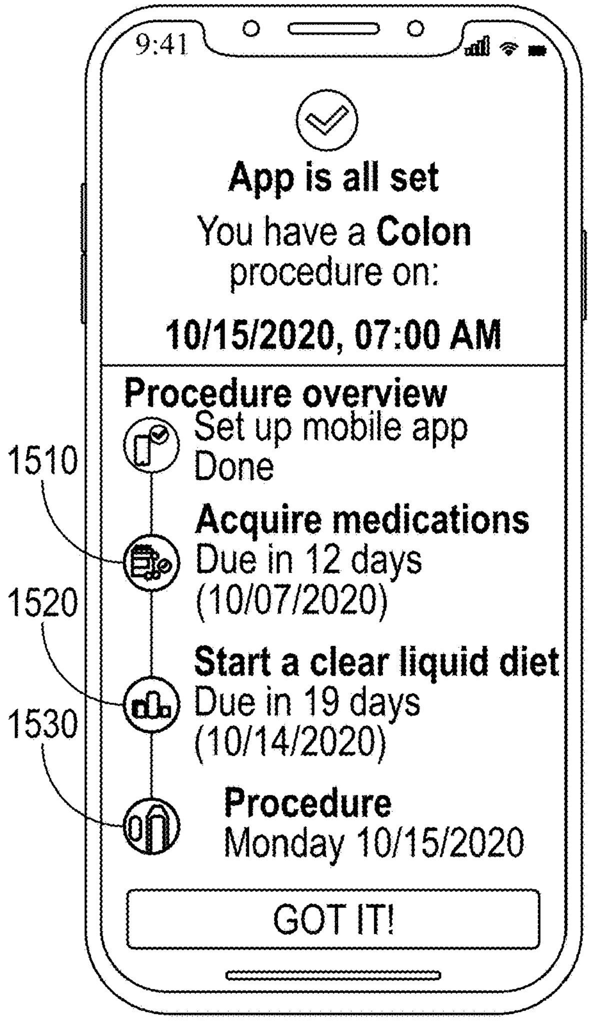
FIG. 15 is an exemplary screen of a patient app showing tasks for a capsule endoscopy procedure, in accordance with aspects of the present disclosure.

The aspects and embodiments described in connection with FIGS. 13-15 are exemplary and variations are contemplated to be within the scope of the present disclosure. For example, the patient app can access and display other regimen not shown or described herein. Additionally, other display screens may be displayed before, between, and/or after the display screens of FIGS. 13-15. For example, a display screen can request a patient confirmation that a regimen has been completed (not shown). The patient confirmation can be communicated to the cloud system, and then conveyed to a healthcare provider to keep the healthcare provider apprised regarding the patient's progress and compliance. As another example, various screens and operations of the patient app may be presented and performed offline without Internet connection and/or without connection to the cloud system, so that the patient will be able to follow the instructions in offline mode. Such variations are contemplated to be within the scope of the present disclosure.

Figure 16:
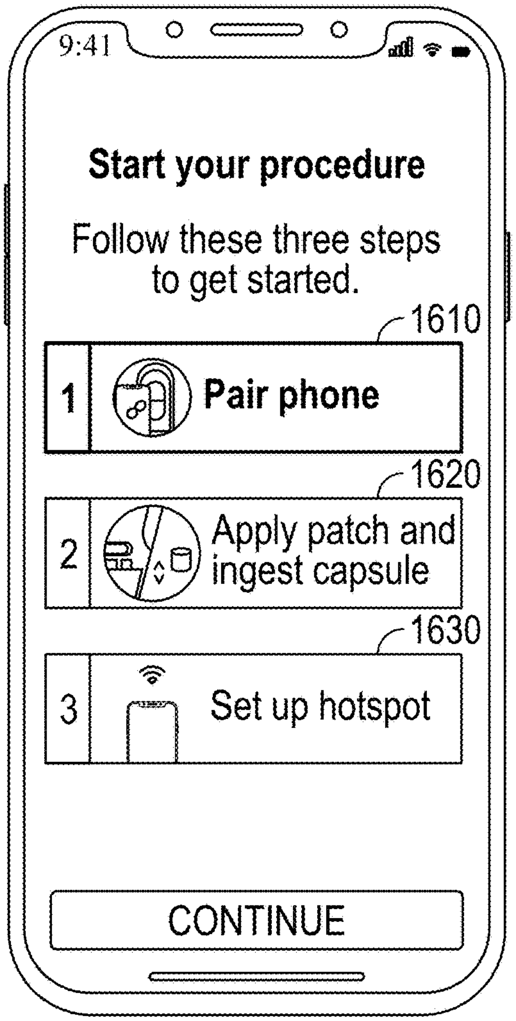
FIG. 16 is an exemplary screen of a patient app for starting a capsule endoscopy procedure, in accordance with aspects of the present disclosure.

FIG. 16 shows an exemplary display screen for starting a CE procedure. The display screen includes three initial tasks, including pairing the patient mobile device with the wearable device 1610, applying the patch/wearable device and ingesting the capsule 1620, and setting up a hotspot for the capsule 1630. For the first task 1610, the patient mobile device can be paired with the patch/wearable device using Bluetooth® low energy, as mentioned above in connection with FIG. 7. Persons skilled in the art will understand how to implement Bluetooth® discovery, pairing, and communications. For the second task 1620, a healthcare professional can secure the patch/wearable device to the patient if the patient is at a medical facility. Otherwise, the patient can secure the patch/wearable device to his/her body. For the second task 1620, the wearable device does not need to be a patch and can be another type of wearable device. For the third task 1630, the patient app can set up connection of the wearable device to a mobile hotspot provided by the patient mobile device, as described above in connection with FIG. 7. The illustrated start-up tasks 1610-1630 are exemplary, and the start-up procedure may include other tasks not described herein.

Figure 17:
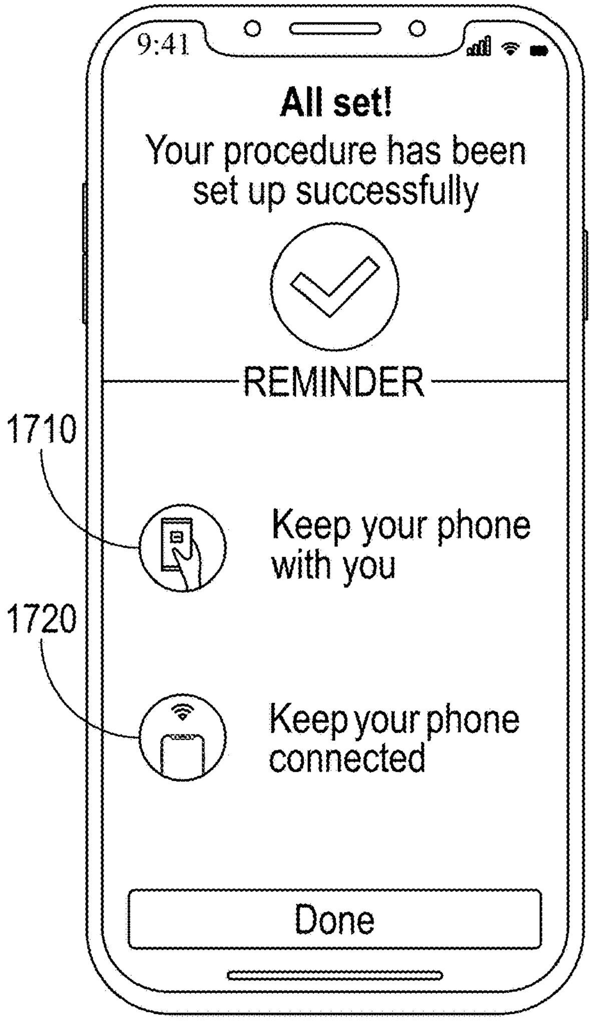
FIG. 17 is an exemplary screen of a patient app confirming successful setup of a capsule endoscopy procedure, in accordance with aspects of the present disclosure.

FIG. 17 shows an example of a display screen when the tasks are completed and the CE procedure has been property set up. As shown in FIG. 17, the display screen reminds the patient to maintain the mobile device's Internet connectivity and to keep the mobile device with the patient 1710. The display screen provides an option to connect the wearable device to a Wi-Fi network provided by a communication device (e.g., router) 1720, which is the configuration illustrated in FIG. 8 and described above. In particular, the patient can enter Wi-Fi access credentials into the patient app, which can communicate the credentials to the wearable device using the BLE connection, as described above. Once the wearable device is connected directly to a communication device such as a router, the wearable device can communicate procedure data using that Wi-Fi connection but can ping the patient mobile device regularly to keep the mobile hotspot connection active.

Figure 18:
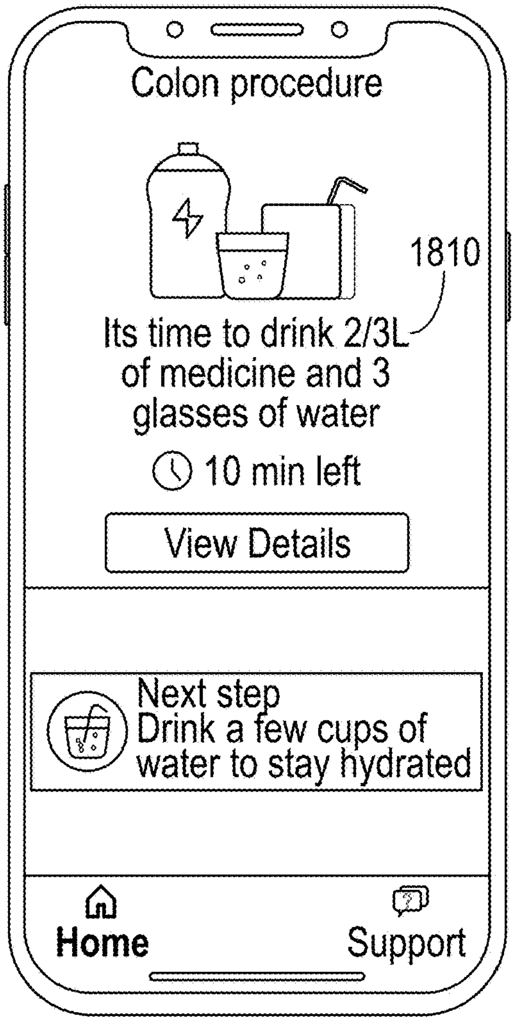
FIG. 18 is an exemplary screen of a patient app showing an instruction during a capsule endoscopy procedure, in accordance with aspects of the present disclosure.

FIG. 18 provides an example of a display screen during the CE procedure, in which a regimen may be conveyed to the patient. In various embodiments, the regimen may be predetermined and, in various embodiments, the regimen may be prescribed during the CE procedure by a healthcare professional monitoring the procedure. The regimen may be communicated to the patient mobile device and displayed to the patient. In the illustrated embodiment, the regiment 1810 is an instruction to the patient to take a boost (i.e. medication), which may help or facilitate the capsule device advance in the gastrointestinal tract. Other types of boosts or medication administration during a CE procedure are contemplated to be within the scope of the present disclosure. Additionally, various regimen and boosts may be presented offline without Internet connection and/or without connection to the cloud system, so the patient can follow the instructions in offline mode. Information may be collected to determine the level of the patient's compliance throughout the procedure. Such information may be provided to the healthcare provider supervising the procedure, the reader, and/or the referring physician.

Figure 19:
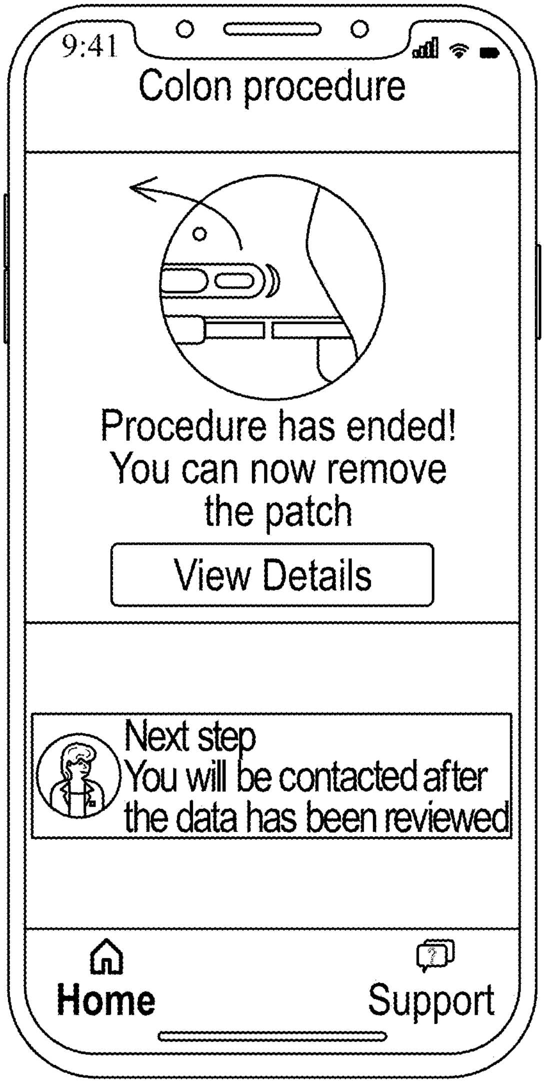
FIG. 19 is an exemplary screen of a patient app showing an end of a capsule endoscopy procedure, in accordance with aspects of the present disclosure.

FIG. 19 shows a display screen notifying the patient that the procedure has ended and the wearable device can be removed. In various embodiments, a wearable device can detect that the procedure has ended when it no longer receives any communications from the capsule, for example. No longer receiving any communication can indicate that the capsule device has exited the body. In various embodiments, a computing system, such as the remote computing system of FIG. 1 or AI cloud of FIG. 12, can process images received from the wearable device during the CE procedure to determine whether the CE procedure has ended. In various embodiments, the wearable device can process images in the procedure data to determine whether a CE procedure has ended. For example, if the CE procedure is intended to capture images of a small bowel and the capsule has passed into the colon, the remote computing system can process the images received from the wearable device to determine that the images are colon images and the CE procedure has ended. In various embodiments, a remote computing system can apply machine learning in an online manner to classify the images during the course of the CE procedure. Persons skilled in the art will understand how to train a machine learning system to classify tissue images and determine, for example, whether the images are colon images or images of another anatomy. By processing the images in an online manner, a remote processing system may determine that the CE procedure has ended much earlier than when the capsule stops transmitting to the wearable device. Accordingly, a patient may be able to fully resume activities earlier. In various embodiments, the capsule, the wearable device, and/or the patient mobile device may have processing capabilities and may be able to individually or collaboratively process images to determine whether the CE procedure has ended. Such embodiments are contemplated to be within the scope of the present disclosure.

If procedure data in the wearable device is not fully uploaded to the cloud system, the patient may be instructed to provide the wearable device to a medical facility for manual transfer of the procedure data from the wearable device. According to some aspects, a healthcare provider may be notified when a procedure is completed, e.g., via the healthcare provider application, which is described below in connection with FIGS. 20-22.

Figure 20:
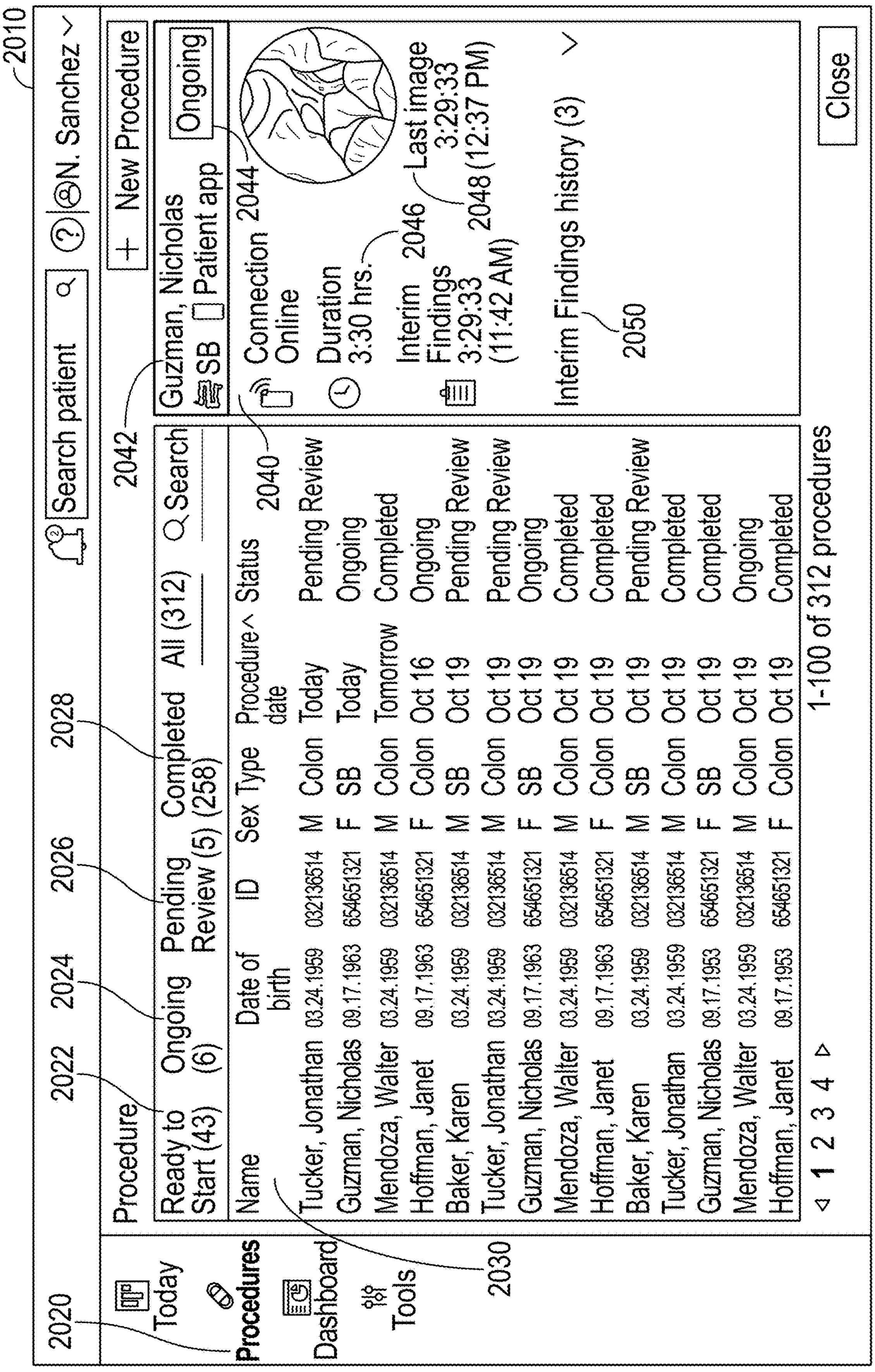
FIG. 20 is an exemplary screen of a healthcare provider app for displaying a listing of capsule endoscopy procedures, in accordance with aspects of the present disclosure.

FIG. 20 shows a display screen of a healthcare provider (HCP) app located on an HCP device, such as a HCP device shown in FIG. 10 or FIG. 11. In various embodiments, the HCP device can be a tablet, a laptop, a netbook, a workstation, or a desktop computer, among other things. A healthcare professional handling and/or supervising the CE procedure, such as a nurse or a physician, may be provided with dedicated HCP software or application. The HCP application may be installed on a mobile device to be used by the healthcare professional (e.g., a tablet computer, an iPad or another handheld device) and/or on a stationary device in the medical facility in which the healthcare professional receives the patients and/or performs the procedure (e.g., a clinic or a hospital in which the patient is checked in by the HCP and swallows the capsule). The HCP device may be a dedicated device.

The HCP application may facilitate the handling and/or managing of the CE procedures, including check-in processes and pairing processes between different devices or components of the disclosed systems. The HCP application may conveniently allow the HCP to review online the progress and status of the CE procedures (e.g., by displaying a dashboard of procedures in progress), to access procedure data, and to connect with data systems of the medical facility. In the illustrated embodiment, the HCP app 2010 allows a medical facility and healthcare providers to obtain information relating to CE procedures 2020 which are ready to start 2022, CE procedures which are ongoing 2024, CE procedures which have a compiled study ready for review 2026, and CE studies which have a completed report 2028. A healthcare professional can interact with the HCP app 2010 to obtain a listing of such procedures 2030 and to select a particular procedure 2040 to access. When a healthcare provider selects a particular procedure 2040, information relating to the procedure can be shown on the display screen, such as type of CE procedure 2042, status of the procedure 2044, duration of the procedure 2046, and latest image received from a wearable device or from the cloud system 2048. The displayed information also includes interim findings history 2050, which will be described in connection with FIG. 21. As described in connection with FIG. 12, the information shown in the HCP app can be provided to the HCP app by an HCP cloud sub-system of a cloud system. However, the information generated from image and procedure data analysis would be generated in the cloud system by the AI cloud sub-system (FIG. 12).

The display screen of FIG. 20 is exemplary and does not limit the scope of the present disclosure. Variations are contemplated to be within the scope of the present disclosure. According to some aspects, the HCP app may provide notifications of malfunctions or problems in equipment or in ongoing CE procedures, including hardware problems, connection problems or interferences among active CE procedures (e.g., procedures performed on patients located in a medical facility). For example, in various embodiments, the HCP app may provide online information indicating the stage of the procedure. In various embodiments, the HCP app may provide an alert when starting a check-in or setup phase of a procedure, where no reader (e.g., a GI physician) is assigned to the procedure in the system. In various embodiments, the HCP app may provide a way to verify that the patient completed a pre-procedure preparation properly and has acknowledged it.

Figure 21:
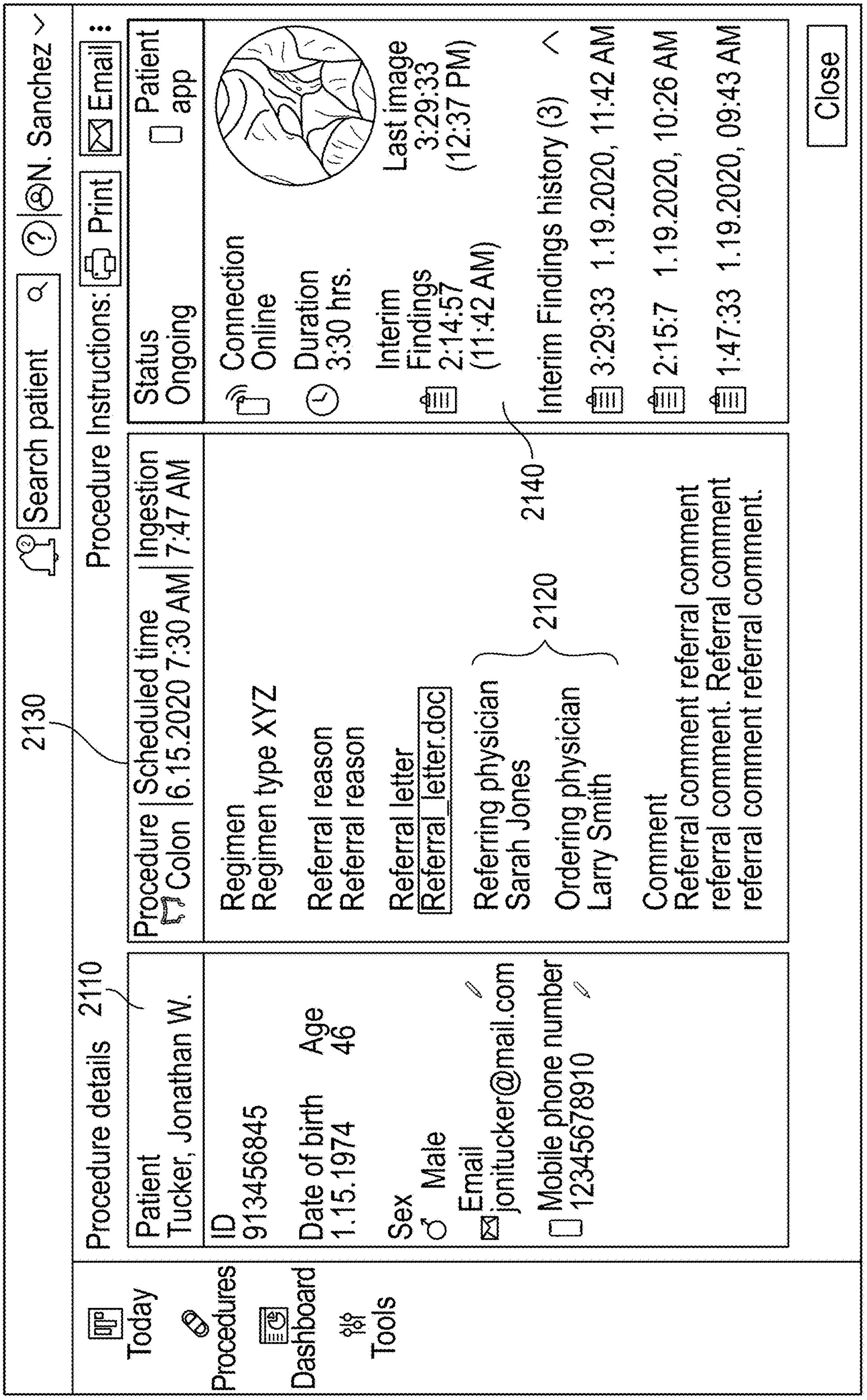
FIG. 21 is an exemplary screen of a healthcare professional app for monitoring a procedure in-progress, in accordance with aspects of the present disclosure.

FIG. 21 shows a display screen of an HCP app that includes detailed information regarding a CE procedure, including information relating to the patient 2110, information relating to relevant physicians 2120, and information relating to the procedure 2130. The illustrated display screen shows that a particular procedure has been ongoing for 3 hours and 30 minutes, and three interim findings 2140 are available. One interim finding was provided about 1 hour and 47 minutes into the procedure, a second interim finding was provided about 2 hours and fifteen minutes into the procedure, and a third interim finding was provided about 3 hours and 29 minutes into the procedure. An "interim finding" may include, for example, identified images of interest and optionally an indication of identified event indicators (e.g., pathologies) in the images. As used herein, the term "event indicator" refers to an indicator that an event has occurred. An event may be presence of a pathology, such as growth of a polyp or GIT bleeding, or may be a transition event, such as transition from one GIT portion to another GIT portion, or may be appearance of an anatomical landmark, such as a duodenal bulb at a transition from the small bowel to the colon, or may be other events not specifically mentioned herein. As such, an "interim finding" may include one or more images and according to some aspects, may be a report that is provided during a CE procedure based on procedure data obtained thus far in the procedure. Whereas a full compiled study or CE report is generated after the procedure is completed and is based on the full procedure data for the CE procedure, an interim finding is compiled during the CE procedure to provide a healthcare professional with a preview of partial findings as the procedure progresses. In various embodiments, an interim finding can be initiated at predetermined times during a CE procedure. In various embodiments, an interim finding can be generated whenever a particular amount of procedure data has been received. An interim finding may also be generated on-demand at the request of a healthcare professional. The interim findings 1240 may allow a healthcare professional to identify need for an immediate or urgent treatment.

According to some aspects, the online processing of images by the cloud system (e.g., AI cloud sub-system) may provide online identification of polyps (e.g., via the interim finding) and may allow for a same day colonoscopy. In case an identified polyp needs to be removed, a physician provided with the interim findings may suggest the patient to have a colonoscopy at the same day to remove the polyp. Same day colonoscopy may be more convenient and less difficult for the patient because the patient is already completed with pre-procedure preparation.

Figure 22:
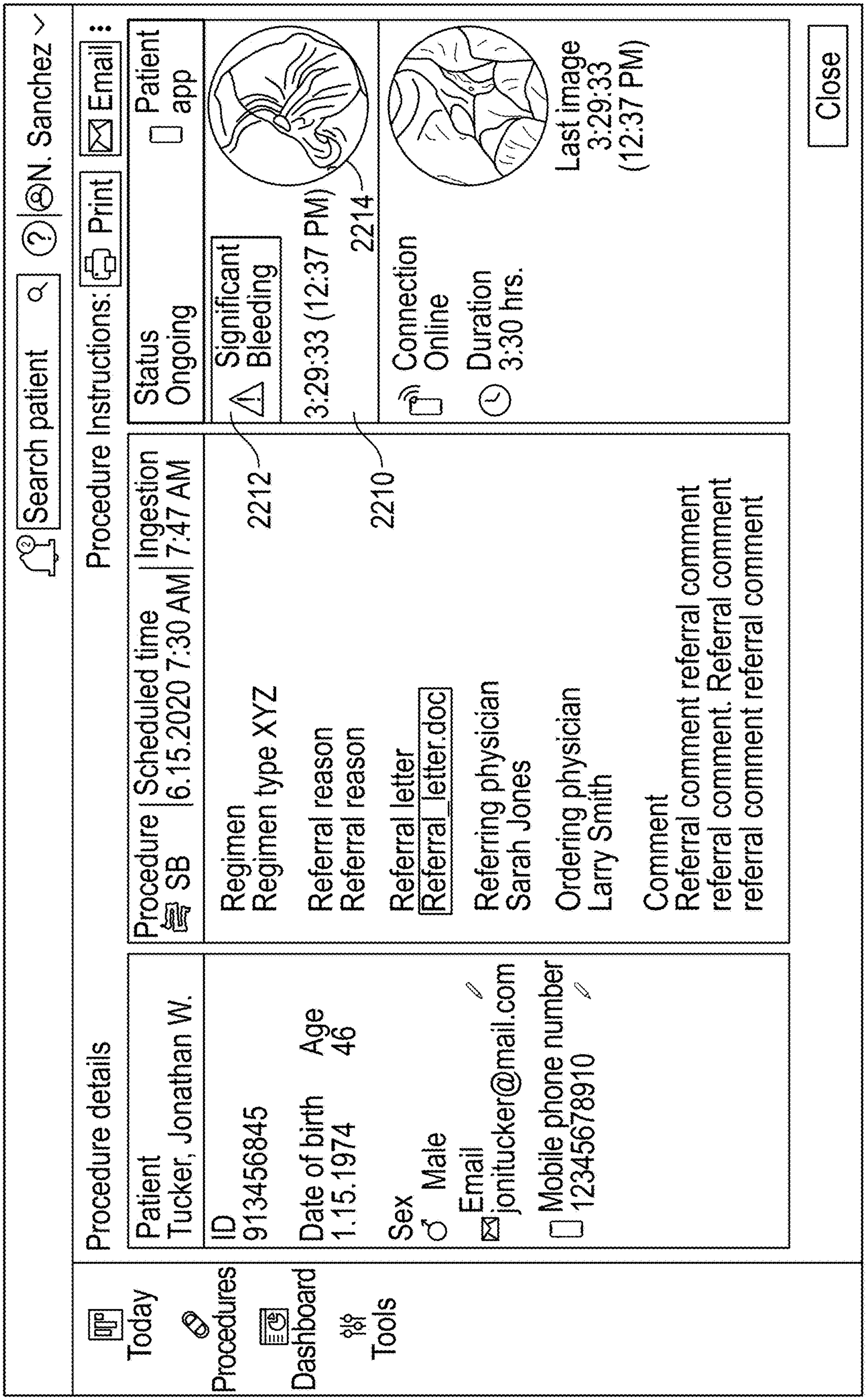
FIG. 22 is an exemplary screen of a healthcare professional app indicating an alert for a procedure in-progress, in accordance with aspects of the present disclosure.

FIG. 22 shows an example of a display screen of an HCP app that provides an online alert 2210 regarding a detected high/urgent medical risk. As mentioned above, online processing by the cloud system (e.g., FIG. 12, AI cloud) can be applied to process images received from the wearable device during the CE procedure. The AI cloud can operate to identify potential event indicators, such as cancer events, significant bleeding, or various pathologies, among other things. Persons skilled in the art will understand how to train a machine learning system to identify various event indicators in images, including aspects of training machine learning systems using training data. When online processing by the cloud system detects an event indicator that is categorized as a high medical risk, such as significant bleeding, the cloud system can provide an online alert 2210 to the HCP app to indicate the detection 2212 and include one or more images showing the detected pathology or event 2214. In the example of FIG. 22, the cloud system has detected significant bleeding 2212 in the small bowel, and the HCP app provides an online alert 2210 showing the finding 2212 and an image 2214 of the detected bleeding. In various embodiments, the HCP app can be preconfigured to detect particular event indicators or pathologies and can be preconfigured to identify certain events or pathologies as high/urgent medical risk. In various embodiments, a healthcare provider may select events or pathologies to categorize as high/urgent medical risk and that trigger an online alert.

The description above described aspects of a patient app and an HCP app. The following will describe the options for remote view, real-time view, and a near real-time view. While the real-time view requires a separate app, the near-real time view and the remote view may be provided as features of the HCP application.

Figure 23:
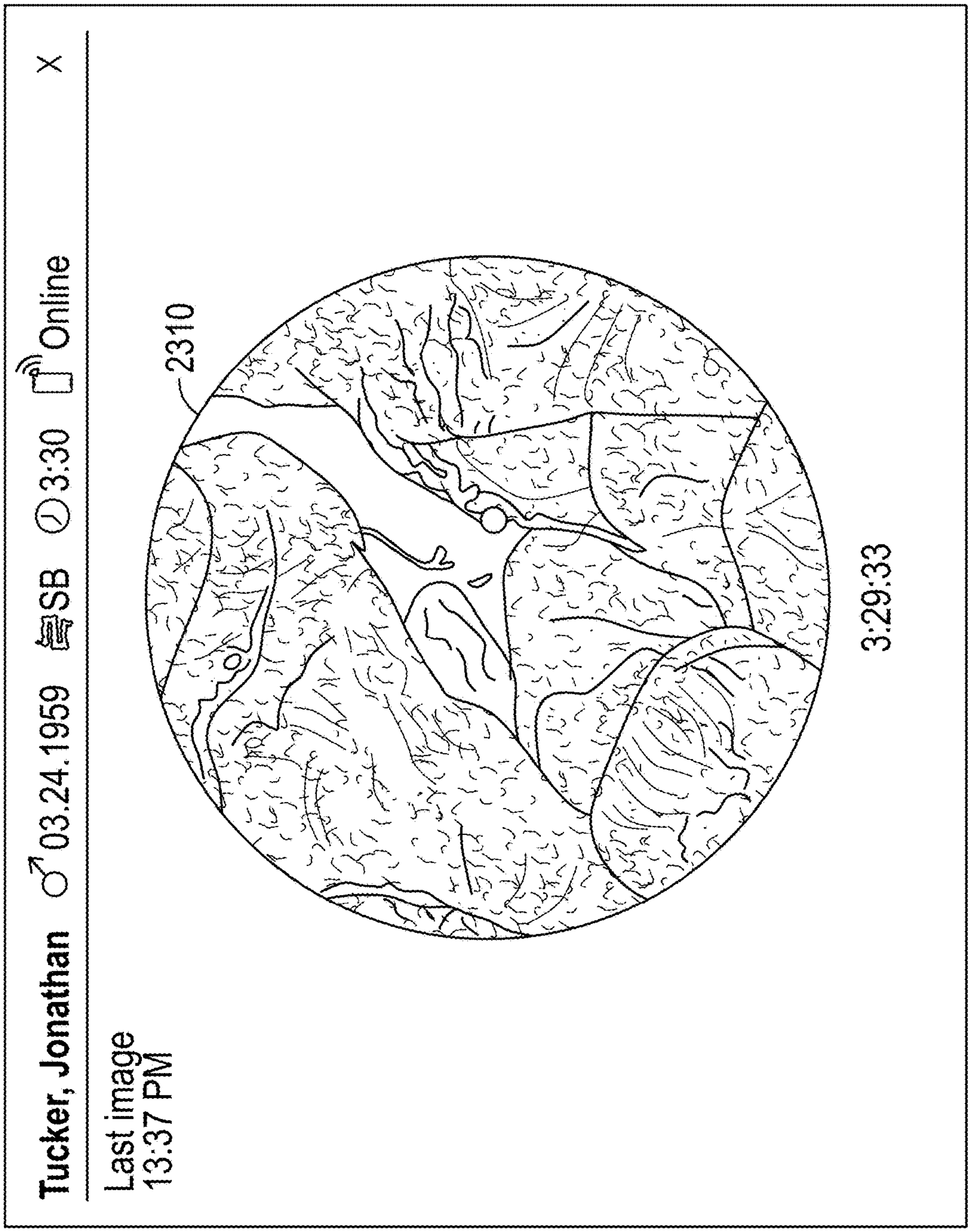
FIG. 23 is an exemplary screen of an app for viewing images of a capsule endoscopy procedure, in accordance with aspects of the present disclosure.

FIG. 23 shows a display of a remote view, which can be a part (e.g., a feature) of an HCP app (1230, FIG. 12). The remote view operates to access images of a procedure that have been uploaded to a cloud system. The illustrated image 2310 is the latest image that was uploaded to the cloud system. A healthcare professional can, for example, swipe left or right to access earlier or later images, or can navigate through images using a keyboard or mouse or other interface device. As the cloud system receives further images from the wearable device, they can become available to the remote view. In some aspects, the remote view may be available via a dedicated app. To enable the remote view, no special instructions are communicated other than an instruction to access available images for a procedure. Therefore, even if the wearable device includes images which have not been yet uploaded to the cloud system, the wearable device is left to upload such images on its own schedule and by its own processes. Because the remote view requires interaction with the cloud system only, it may be accessible through Internet connectivity.

In contrast to the remote view feature or app, the real-time view app (1220, FIG. 12) operates to obtain images from the wearable device as immediately as possible using the connectivity shown in FIG. 10. As mentioned above, in the connectivity of FIG. 10, the HCP device 634 connects directly to the wearable device 614. The wearable device 614 operates as a Wi-Fi access point, and the HCP device 634 operates as a Wi-Fi client device, and the devices also have a BLE connection 1050. Because the HCP device 634 obtains images from the wearable device 614 directly, access to such images occurs essentially in real time, and the wearable device 614 can communicate images to the HCP device 634 as soon as the wearable device receives them. In various embodiments, the display screen of FIG. 23 can be applied to the real-time view app for viewing images. Display screens for requesting real-time view from a wearable device are not shown but would be understood by persons skilled in the art of Wi-Fi and Bluetooth communications. Because real-time view relies on the connectivity shown in FIG. 10, the real-time view app is only operable for healthcare physicians who are at the same location as the wearable device and the patient. The real-time view may be used by a HCP to verify the proper operation of the procedure, e.g., by viewing images received from the wearable device thus verifying that images are captured by the capsule device and are received by the wearable device. Furthermore, the real-time view may be used, for example, to verify that the capsule has reached a specific portion of the GIT, including the GIT portion of interest or the GIT portion to be imaged. For example, an HCP may verify that the capsule has entered the SB and is not stuck, e.g., in the stomach. In case the HCP reviews the images received from the wearable device and realizes that the capsule is still in the stomach, he may administer a boost to advance the capsule.

The near real-time view provides a timing of image access that is between the timing provided by the remote view and the real-time view, and utilizes the connectivity shown in FIG. 11. In accordance with FIG. 11, the near real-time view can reside on a HCP device 632, 634 that is remote from the wearable device 614 and the patient. However, rather than waiting for the wearable device 614 to upload procedure data to the cloud system 640 on its own schedule, the near real-time view communicates a special instruction to the cloud system 640 to check on the age of the procedure data received from the wearable device 614. If the age of the procedure data is older than a threshold, the cloud system 640 sends an instruction to the wearable device 614 to immediately upload the procedure data stored thereon. In various embodiments, the age threshold can be set to minutes or seconds, thereby causing the wearable device 614 to immediately upload its images to the cloud system any time the procedure data is seconds or minutes old. In this manner, the cloud system 640 receives the procedure data from the wearable device in near real-time, and the near real-time view displays such images in near real-time. In various embodiments, the display of FIG. 23 can also be applied to the near real-time view for displaying images. Display screens for requesting near real-time view from a cloud system are not shown but would be understood by persons skilled in the art of communications.

FIG. 23 and the embodiments described above are exemplary and do not limit the scope of the present disclosure. Variations of the display of FIG. 23 can be used for the remote view, real-time view, and near real-time view apps.

The following will describe the reader app 1240 of FIG. 12, which may also be referred to as a viewer app. According to some aspects, a reading or viewer application or software may be provided that allows a reader, e.g., a GI physician, to access a compiled study of the procedure data and to provide input for generating a CE report for the procedure. In some aspects, such application may be installed and used or accessed (e.g., via web) from a stationary or mobile computing device (e.g., a handheld device such as an iPad). In some aspects, the reading app may be incorporated in the HCP app. In some aspects, the reading application may allow the reader to access the compiled study and provide input for generating of the CE procedure report remotely.

A procedure study may include images selected from the procedure data (i.e., the procedure data received by the computing system according to the disclosed systems and methods). The images of a study may be, for example, images selected to represent the procedure data or the GIT portion of interest, to include or represent one or more event indicators of interest or a combination of such and depending on the goal of the CE procedure. According to some aspects, the study may include additional data, such as estimated location of the images along the GIT, indication to an event indicator identified (at some level of certainty) in the image and a size of such event indicator. The images may be processed and analyzed by the computing system (e.g., the AI cloud of a cloud system according to the disclosed systems and methods) to select the images to be included in the study and to receive additional data. In some embodiments, the images of a study may include two levels of images selected at two stages. At a first stage, first level images may be selected as disclosed above. At a second stage, second level images may be selected to provide additional information for images of the first level. According to some aspects, first level images will be displayed to the viewer by default while second level images will be displayed only per a user's action or request. The first and second level images may be displayed as exemplified and described with respect to FIGS. 24 and 25 herein below.

According to some aspects, a subset of images of a captured stream of in-vivo images (i.e., images of a procedure data) may be automatically selected form the stream of in-vivo images according to a first selection method. For each image of at least a portion of the subset of images, one or more corresponding additional images from the stream of in vivo images may be selected according to a second selection method. For each image of the subset of images, one or more images may be selected according to a second selection method. The subset of selected images (i.e., first level images) may be displayed for a user's review. Upon receiving user input (e.g., mouse click, activating a GUI control etc.), one or more additional images (i.e., second level images) corresponding to a currently displayed image of the subset of images (i.e., a first level image), may be displayed. The second selection method may be based on a relation between images of the stream of in vivo images and the currently displayed image. Such a relation between the first and second level images may be: the images are identified to include at least a portion of the same feature or the same event or event indicator, the images are identified to include at least a portion of the same type of feature or event or event indicator, the images were captured in time proximity, the images are localized adjacently along the at least portion of the subject's GIT, and combinations thereof. The subset of images and the one or more images corresponding to the subset of images may be automatically selected by the computing device (e.g., the AI cloud). According to some aspects, the selection may involve the application of Machine Learning and specifically Deep Learning.

Figure 24:
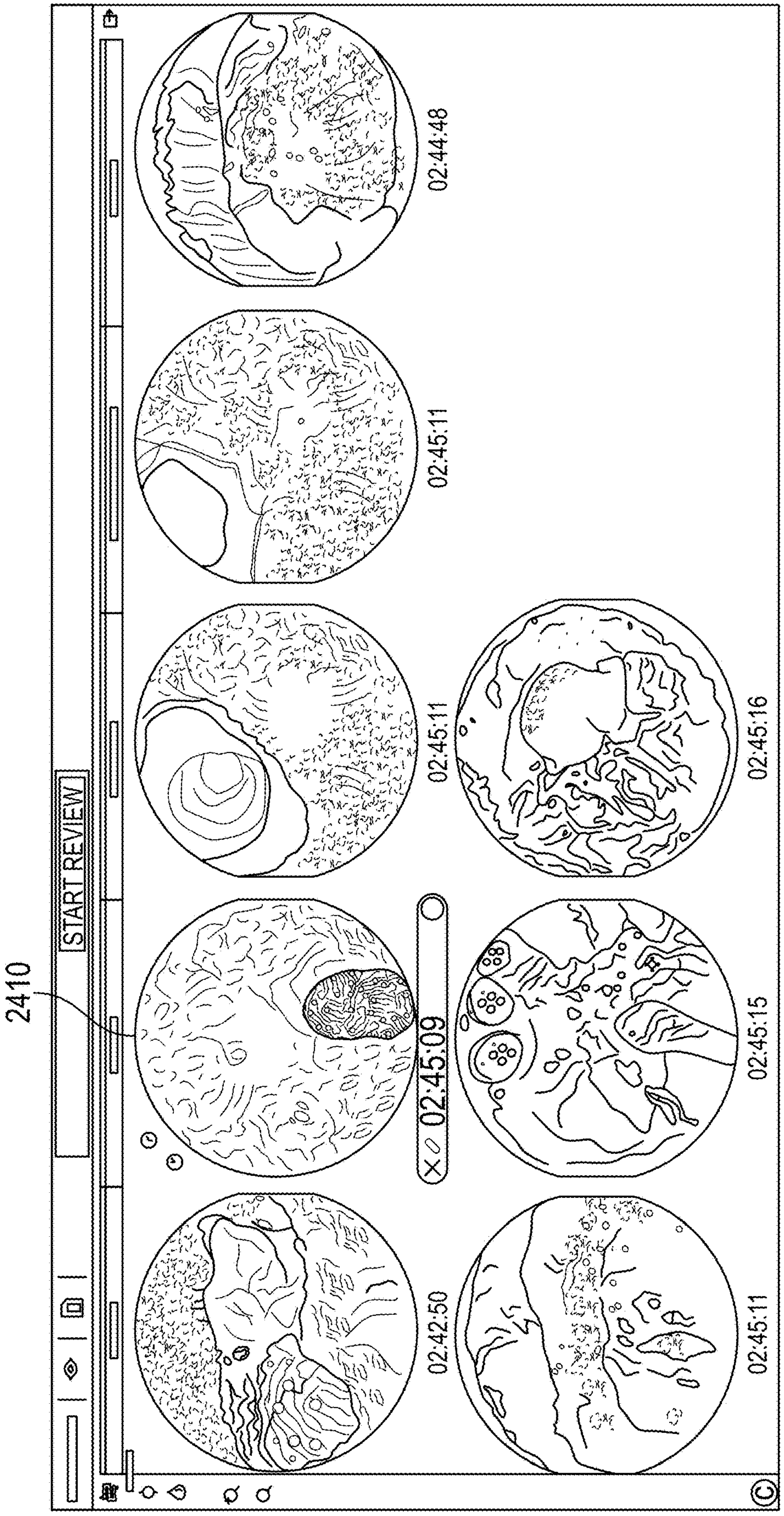
FIG. 24 is an exemplary screen of a viewer/reader app for viewing a compiled study of a capsule endoscopy procedure, in accordance with aspects of the present disclosure.
Figure 25:
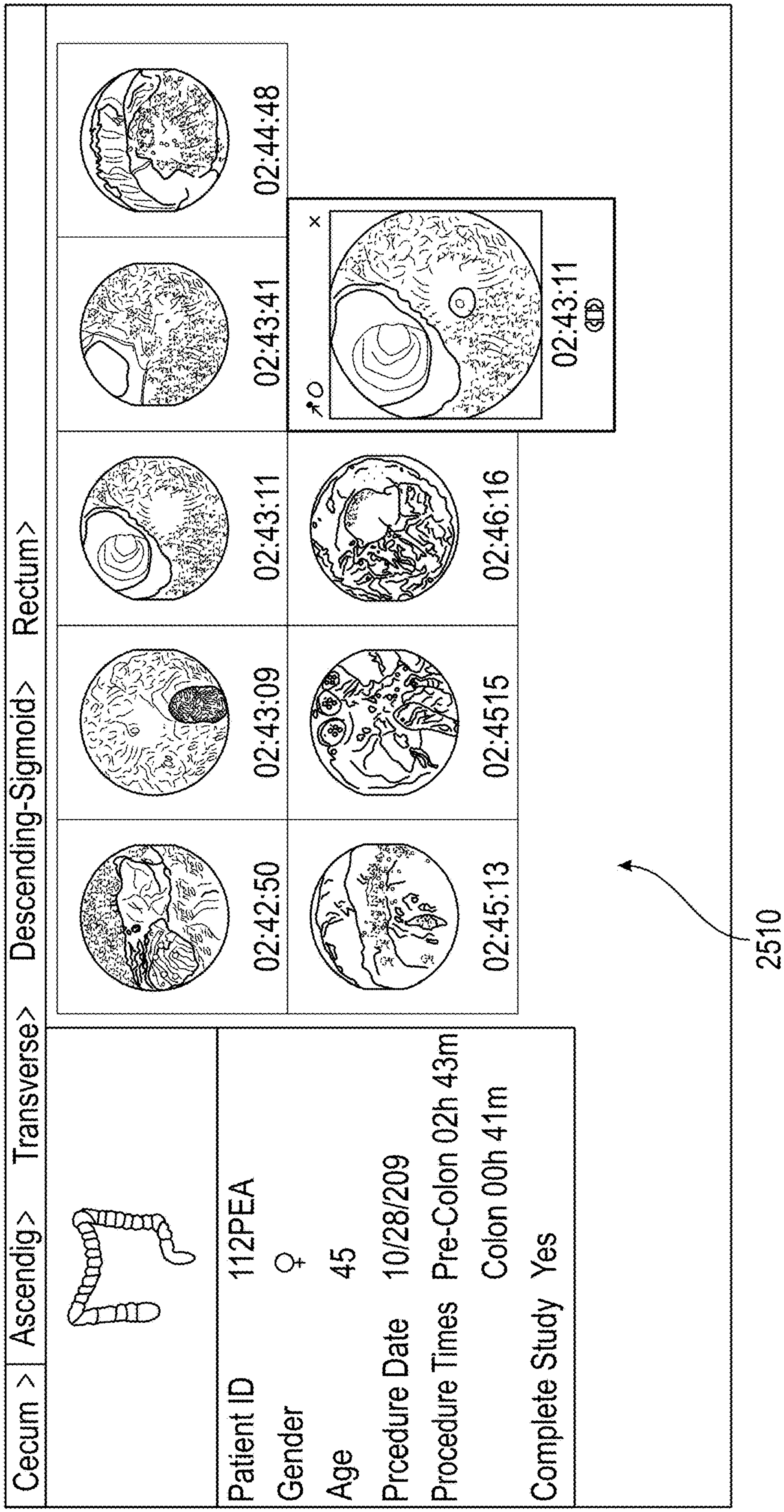
FIG. 25 is another exemplary screen of a viewer/reader app for viewing a compiled study of a capsule endoscopy procedure, in accordance with aspects of the present disclosure.

FIG. 24 shows a screen of an exemplary display of a compiled study generated based on the systems and methods of the present disclosure. A GUI (or a study viewing application) may be used for displaying a study for a user's review and for generating a study report (or a CE procedure report). The study may be generated based on or may represent one or more predefined event indicators. The screen displays a set of still images included in the study. The user may review the images of the study and select one or more images of which are of interest, e.g., displaying one or more predefined event indicators. For example, the small bowel may include a plurality of pathologies of interest, including: ulcers, polyps, strictures etc. These pathologies may be predefined as event indicators for generating a study based on the present systems and methods. As another example, in a colon procedure aimed for cancer screening, polyps may be of interest. FIG. 24 shows a display of a study of such colon procedure. The illustrated screen displays a portion of the study images. A user may review additional images by sliding between image pages or by switching tabs, for example. According to some aspects, the study images may be displayed according to their location in the colon. The location may be any one of the following five anatomical colon segments: cecum, ascending, transverse, descending-sigmoid and rectum (as shown in FIG. 25). Image in focus may be presented with additional information, such as image 2410. The illustrated display screen may be used by the user, e.g., a clinician, to select the images to be included in the procedure report. The illustrated display screen is exemplary and variations are contemplated to be within the scope of the present disclosure.

With reference also to FIG. 25, the screen shows study images according to their location in the colon segments. The user may switch between display of images located in the different segments by switching between the segments tabs. In some embodiments, the study may also include additional images, i.e., second level images, associated with the first level images, which are displayed by default 2510. In such a case, a user may request (via user input) to display the second level images associated to a displayed image, e.g., the image in-focus. By reviewing the associated images, the reader may receive further information relating to the first level image, which may assist him in determining if the first level image (or optionally any other second level image) is of interest.

Figure 26:
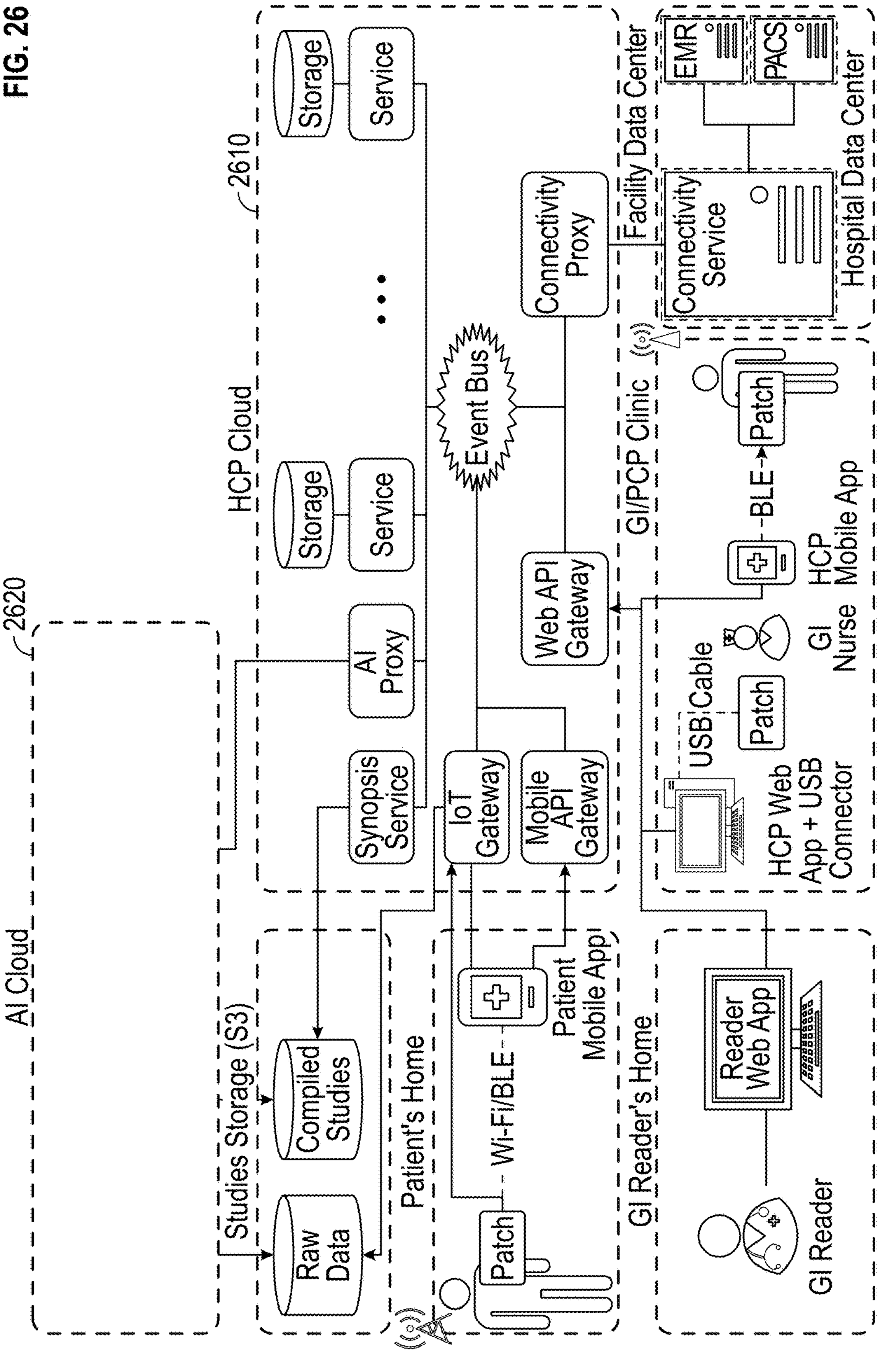
FIG. 26 is a block diagram of exemplary devices and systems and exemplary components for implementing capsule endoscopy procedures, in accordance with aspects of the present disclosure.

FIG. 26 is a block diagram of exemplary devices and systems and exemplary components for implementing capsule endoscopy procedures. Various aspects of FIG. 26 have been previously addressed above. For example, facility data center was addressed in connection with FIGS. 1 and 3, a patient's home system and a GI/PCP clinic system were addressed in connection with FIGS. 6-11, and aspects of the cloud system were addressed in connection with FIG. 12. The following provides a more detailed description of the cloud system, including the HCP cloud sub-system 2610 and the AI cloud sub-system 2620.

The illustrated cloud system is a multi-user system that is able to support a vast number of procedures performed in parallel, even when resource load may dramatically change at different times (e.g., peak hours versus 'low activity' hours or hours with no activity). With respect to the system uptime, the cloud system is dynamically scalable, which allows stable updates and changes to the cloud platform without affecting the system uptime.

The AI cloud sub-system 2620 is responsible for processing data and may perform resource-intensive computations such as machine learning and specifically deep-learning. The AI cloud can also perform non-AI processing and tasks. Some machine learning algorithms are complex and require heavy computation resources. These resources require scaling out when usage load increases, in order to support multiple accounts\users simultaneously during peak levels and to maintain an expected service level. In order to meet ever-growing needs for high performance with strong computation capabilities in scalable platforms, software infrastructure also should effectively exploit the cloud resources to provide both performance and efficiency.

As persons skilled in the art will recognize, a difference between different software architectures is the level of granularity. Generally, a more granular architecture provides more flexibility. A software system is "monolithic" if it has an architecture in which functionally distinguishable aspects (for example data input and output, data processing, error handling, and the user interface) are interwoven rather than being contained in architecturally separate components. In the illustrated cloud system, the software architecture of the cloud system breaks a big monolithic flow into small pieces of a structured pipeline that can be managed and scaled more easily by using microservices technology. Microservices, or microservice architecture, is an approach to application development in which a large application is built as a suite of modular components or services. When operations are divided into microservices, each microservice is not dependent on most of the other microservices and generally can work independently.

Such a software architecture allows scalability of the system, as services may be added or removed on-demand. Each microservice is packaged in a container, and optionally may be packages in a container-docker. A container is a standard unit of software that packages up code and all its dependencies so the application runs quickly and reliably from one computing environment to another. A docker container is a lightweight, standalone, executable package of software that includes everything needed to run an application, such as code, runtime, system tools, system libraries, and settings. The docker container is a kind of a virtual environment, and holds, for example, an operation system and all the elements needed to run the microservice (e.g., an application). The cloud system of FIG. 26 can use microservices and can use docker containers to hold all of the elements needed to run a microservice.

An orchestrator application, such as Kubernetes, can be used for containers management. The containers management application may add or remove containers. For a group of machines and containerized applications (e.g. Dockerized applications), the orchestrator can manage those applications across those machines. The use of orchestrator may better the performance of the system.

In the cloud system of FIG. 26, each machine (i.e., server) may run one or more microservices. Communication between the services can be implemented in various ways. One approach is a service bus or a message bus, which allows the services to communicate via the bus by a "send and forget" approach. Each service forwards requests to the bus and consumes requests from the bus, when available, thus allowing a response for each request. Using a service bus may also make the communications more efficient because one message may be distributed to multiple services.

A cloud system architecture as described above provides a flexible and efficient cloud platform, simplifies the upgrades in the cloud system, and allows scalability and compatibility for the specific needs of the system clients. It supports and facilitates a multiuser system which services numerous end-users simultaneously. It also allows better handling of malfunctions because the services are mostly independent. At each point of time, the healthiness level of the system, e.g., load level and exceptions in a specific microservice, may be monitored and may be handled immediately. Such an architecture for the cloud system can be sufficient to meet the requirement of the disclosed systems and methods, including heavy computational tasks involving complex algorithms, such as deep learning algorithms and the processing of large amounts of data.

The aspects described above are exemplary and variations are contemplated to be within the scope of the present disclosure. For example, the architecture described above may also be applicable to an on-premises computing system, such as the system of FIG. 3. Such variations are contemplated to be within the scope of the present disclosure.

Various operations will now be described in connection with FIGS. 27-30. The operations are examples of uses of the systems, devices, and methods of the present disclosure. In various embodiments, the operations of FIGS. 27-30 use various systems and devices, such as those shown in FIG. 6. The illustrations and embodiments described below are exemplary and do not limit the scope of the present disclosure.

Figure 27:
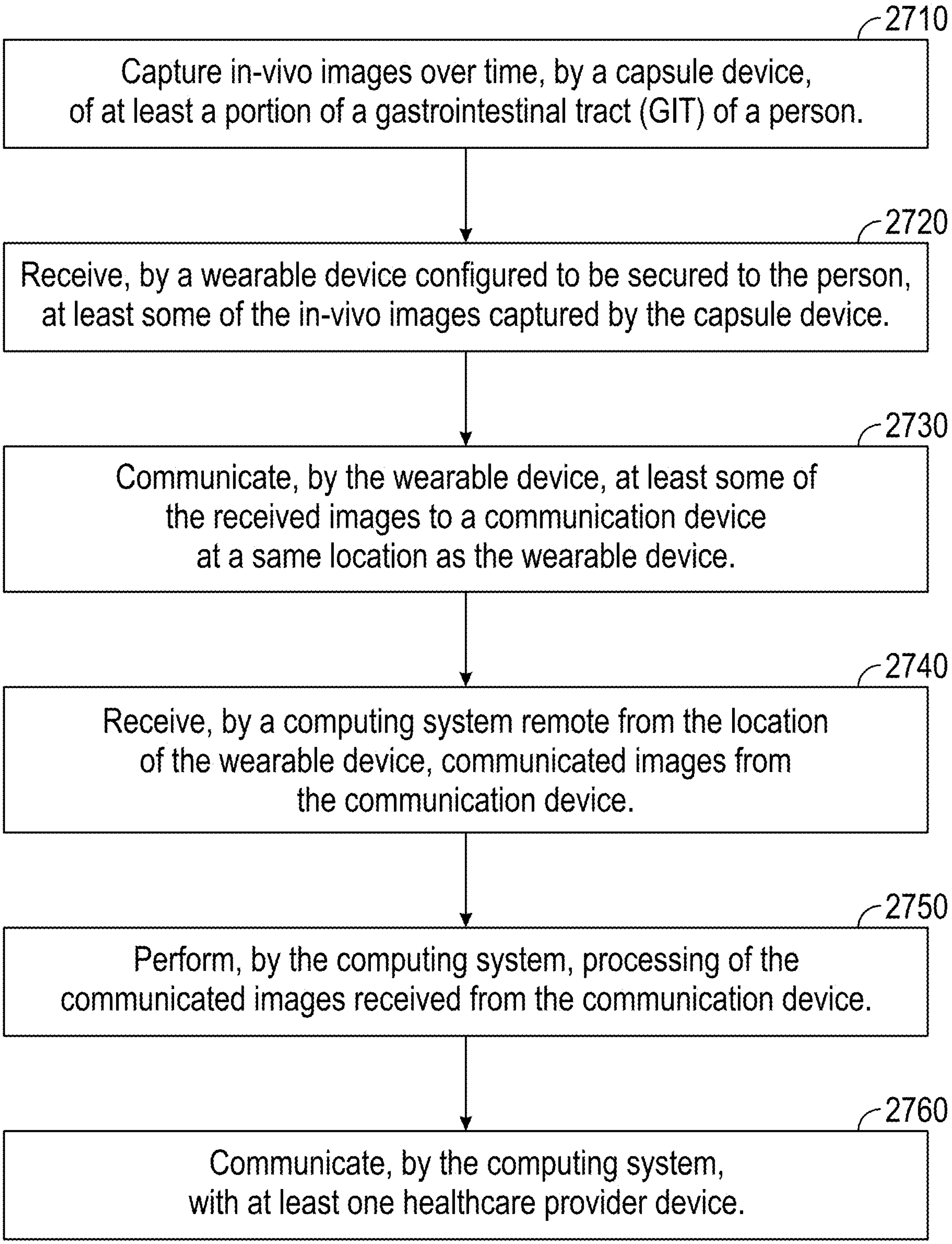
FIG. 27 is a flow diagram of an exemplary operation for processing images captured in a capsule endoscopy procedure and communicating with healthcare provider devices, in accordance with aspects of the present disclosure.

FIG. 27 shows a flow diagram of an exemplary operation for processing images captured in a capsule endoscopy procedure. At block 2710, the operation involves capturing in-vivo images over time, by a capsule device, of at least a portion of a gastrointestinal tract (GIT) of a person. At block 2720, the operation involves receiving, by a wearable device configured to be secured to the person, at least some of the in-vivo images captured by the capsule device. At block 2730, the operation involves communicating, by the wearable device, at least some of the received images to a communication device at a same location as the wearable device. The communication device and the wearable device can be located at the same location when both are, for example, at the patient's home or at a healthcare provider's facility. At block 2740, the operation involves receiving, by a computing system remote from the location of the wearable device, communicated images from the communication device. At block 2750, the operation involves performing, by the computing system, processing of the communicated images received from the communication device. At block 2760, the operation may optionally involve communicating, by the computing system, with at least one healthcare provider device. In various embodiments, the computing system may communicate with at least one healthcare provider device regarding a patient's progress and status before, during, and/or after the capsule endoscopy procedure or with respect to results of the procedure or a portion of it. The operation of FIG. 27 is exemplary and variations are contemplated to be within the scope of the present disclosure.

Figure 28:
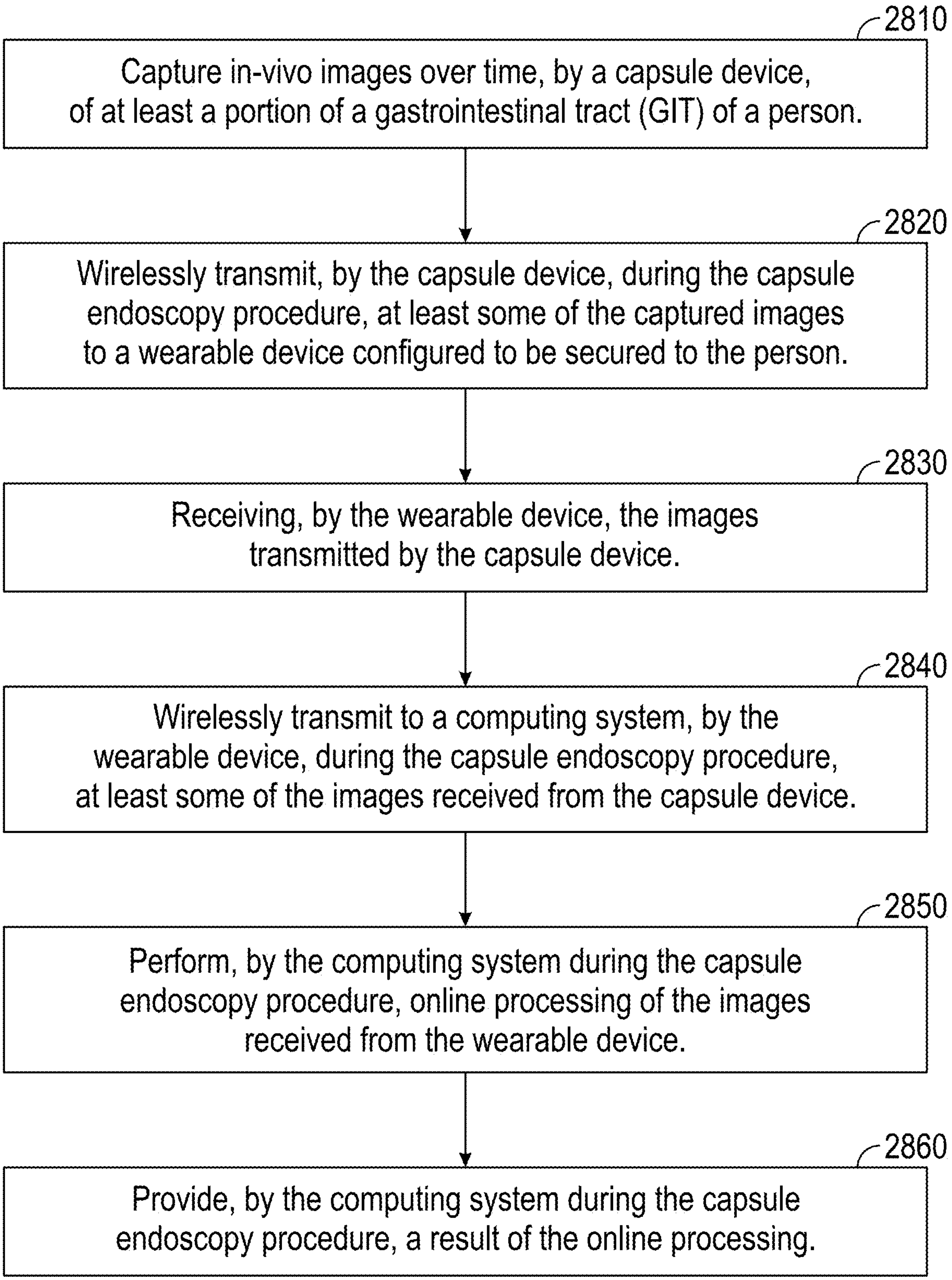
FIG. 28 is a flow diagram of an exemplary operation for online processing of images captured in a capsule endoscopy procedure, in accordance with aspects of the present disclosure.

FIG. 28 shows a flow diagram of an exemplary operation for online processing of images captured in a capsule endoscopy procedure. At block 2810, the operation involves capturing in-vivo images over time, by a capsule device, of at least a portion of a gastrointestinal tract (GIT) of a person. At block 2820, the operation involves wirelessly transmitting, by the capsule device, during the capsule endoscopy procedure, at least some of the captured images to a wearable device configured to be secured to the person. At block 2830, the operation involves receiving, by the wearable device, the images transmitted by the capsule device. At block 2840, the operation involves wirelessly transmitting to a computing system, by the wearable device during the capsule endoscopy procedure, at least some of the images received from the capsule device. At block 2850, the operation involves performing, by the computing system during the capsule endoscopy procedure, online processing of the images received from the wearable device. The online processing may include utilizing machine learning and deep learning. And at block 2860, the operation involves providing, by the computing system during the capsule endoscopy procedure, a result of the online processing. In various embodiments, the online processing provides a versatile and comprehensive array of tools that can be used during a capsule endoscopy procedure to better understand a patient's gastrointestinal health and to better treatment and care. The operation of FIG. 28 is exemplary and variations are contemplated to be within the scope of the present disclosure.

Figure 29:
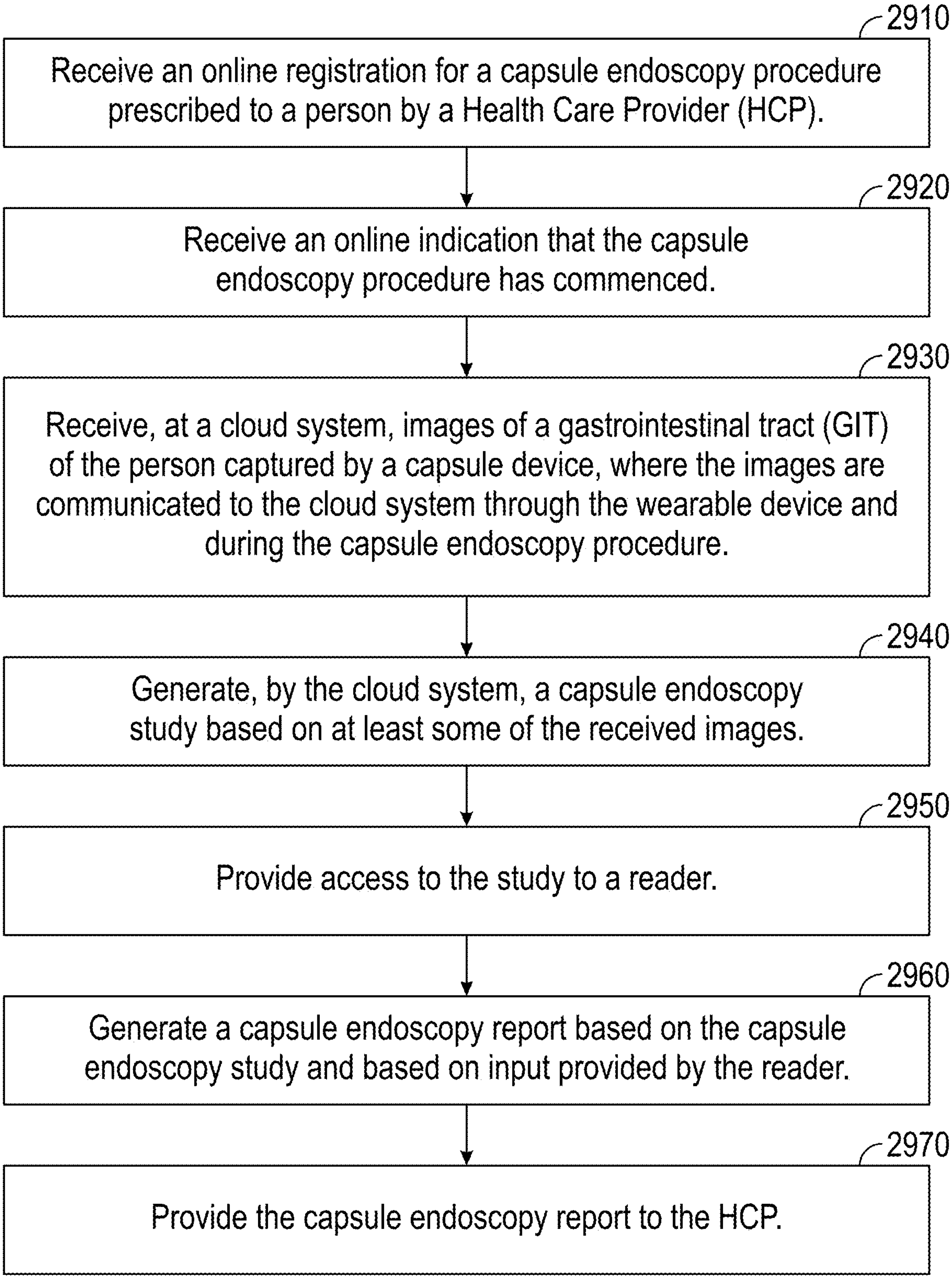
FIG. 29 is a flow diagram of an exemplary operation for a capsule endoscopy procedure using a mailed kit, in accordance with aspects of the present disclosure.

FIG. 29 shows a flow diagram of an exemplary operation for a capsule endoscopy procedure which may be performed entirely at home or at another non-medical environment. At block 2910, the operation involves receiving an online registration for a capsule endoscopy procedure prescribed to a person by a Health Care Provider (HCP). At block 2920, the operation involves receiving an online indication that the capsule endoscopy procedure has com. According to some aspects, such indication may not precede the uploading of the images or may be the mere uploading of the images. At block 2930, the operation involves receiving, at a cloud system, images of a gastrointestinal tract of the person, where the images are captured by a capsule device while traversing the gastrointestinal tract of the person, and communicated to the cloud system through a wearable device during the capsule endoscopy procedure. The images are captured by the capsule device while traversing the gastrointestinal tract of the person and are communicated to the cloud system through the wearable device during the capsule endoscopy procedure. At block 2940, the operation involves generating, by the cloud system, a capsule endoscopy study based on at least some of the received images. At block 2950, the operation involves providing access to the study to a reader. At block 2960, the operation involves generating a capsule endoscopy report based on the capsule endoscopy study and based on input provided by the reader. And at block 2970, the operation involves providing the capsule endoscopy report to the HCP. According to some aspects, the capsule device and the wearable device are disposable and uniquely bonded, and the capsule device and the wearable device were ordered online based on a prescription provided by the HCP and were mailed to a shipping address provided in the order. According to some aspects, the kit is not ordered or purchased online but by, for example, ordering or purchasing in a vendor store. According to some aspects, the kit is not mailed to a shipping address provided in the order, but, for example, purchased at a vendor store (e.g., a pharmaceuticals store).

As an example of the operation of FIG. 29, the illustrated operation may be used for widespread population screening, such as colon cancer screening. A screening medical procedure is typically extensively performed, and therefore should be user friendly to achieve high levels of compliance. Thus, according to some aspects, a kit including a disposable capsule and a disposable wearable device, such as a patch as described above, may be provided directly to the customer (i.e., the patient) with prescription. The patch can be a single unitary device (as opposed device with separate parts) that includes an adhesive configured to adhere to a patient's skin, such as to the abdomen, and may be easily removed. The capsule and disposable device may be pre-coupled or bonded in the factory, thus saving the customer the performance of such pairing procedure. The kit may also include written instructions on how to set the medical procedure (e.g., set and carry the wearable device and swallow the capsule). A patient application may provide instructions on setting up the procedure. The patient may then self-administrate the capsule swallow. During the procedure, the procedure data may be uploaded to a cloud infrastructure via the patient mobile device or directly from the wearable device to the cloud infrastructure (e.g., by incorporating cellular modem and SIM device in the wearable device). An online alert may indicate to the patient that the procedure has ended, and he may remove the wearable device and fully resume his daily activities. The alert may be generated on the cloud by using online processing to identify that the capsule device has traversed the entire GIT portion of interest. Alternatively such detection may be performed on the wearable device. The procedure data may be then processed on the cloud system, and a compiled study may be generated. A reader may have access to the compiled study via a reader application. The reader may review and evaluate the study via the reading application, and a report may be generated. A notification or a copy of the report may be forwarded to the patient (e.g., via the patient application) and/or to the referring physician. According to some aspects, an HCP application similar to the HCP application described above may be provided to the referring physician. The referring physician may use the application, e.g., to communicate with the patients and/or the readers, follow or receive status of the medical procedures and to receive or view the reports. The embodiments described above in connection with FIG. 29 are exemplary and variations are contemplated to be within the scope of the present disclosure.

Figure 30:
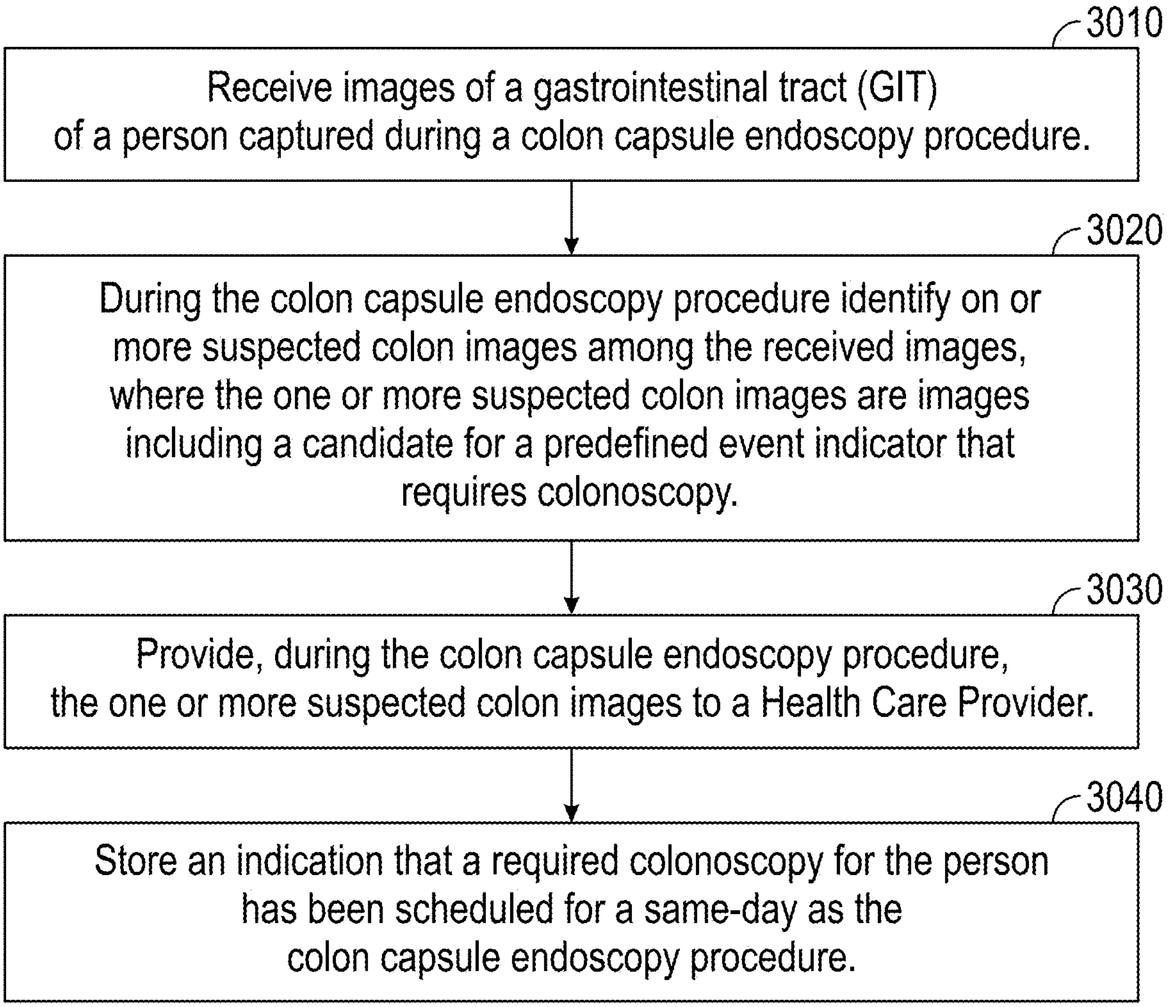
FIG. 30 is a flow diagram of an exemplary operation for scheduling a same-day colonoscopy based on findings during a colon capsule endoscopy procedure, in accordance with aspects of the present disclosure.

FIG. 30 shows a flow diagram of an exemplary operation for scheduling a same-day colonoscopy based on findings during a colon capsule endoscopy procedure. At block 3010, the operation involves receiving images of a gastrointestinal tract (GIT) of a person captured during a colon capsule endoscopy procedure. At block 3020, the operation involves, during the colon capsule endoscopy procedure and until a pre-defined procedure event, identifying one or more suspected colon images among the received images, where the one or more suspected colon images are images identified as images of the colon and as including a candidate for a predefined event indicator that requires colonoscopy, and where the pre-defined procedure event occurs while the colon capsule endoscopy device traverses the colon. Using a cloud infrastructure as a platform for online processing may allow receiving relatively fast results. Utilizing state of the art algorithmics like machine learning and deep learning may allow high performance in identifying suspected images. At block 3030, the operation involves providing, during the colon capsule endoscopy procedure, the one or more suspected colon images to a Health Care Provider. And at block 3040, an optional operation involves storing an indication that a required colonoscopy for the person has been scheduled for a same-day as the colon capsule endoscopy procedure. Because the preparation for a colon capsule endoscopy procedure can be similar or sufficient as the preparation for a colonoscopy, scheduling a colonoscopy on the same day as the colon capsule endoscopy procedure is more convenient for the patient and avoids another round of preparation for the patient. The embodiments described in connection with FIG. 30 are exemplary and variations are contemplated to be within the scope of the present disclosure.

As mentioned above in connection with FIG. 1, and in accordance with aspects of the present disclosure, a capsule device 110 may include processing capabilities that allow the capsules to prune or discard images. As mentioned above, "pruning" an image refers to designating or otherwise treating the image as an image that will not be utilized. In various embodiments, pruning an image may include discarding the image, not storing the image, or deleting the image from memory or from a storage, among other possibilities.

In accordance with aspects of the present disclosure, the operation of pruning images may involve pruning images at a particular rate, i.e., prune every $k^{th}$ image, where k>1. For example, without limitation, a pruning operation may prune every $2^{nd}$ image (k=2), or prune every $3^{rd}$ image (k=3), or prune images at another rate. A higher rate of pruning images (i.e., lower k) utilizes less resources (such as storage resources and/or communication resources) but obtains a less comprehensive capture of the GIT, while a lower rate of pruning images (i.e., higher k) utilizes more resources but obtains a more comprehensive capture of the GIT. As described in more detailed later herein, different pruning rates may be applied depending on the location or segment in the GIT where the capsule captured the images. Images which are not pruned by the capsule 110 may be communicated to a receiver device external to the person, such as communicated to a wearable device 120 worn by or adhered to the person, a mobile device 130 carried by the person, and/or another device (e.g., router or other network device), among other possibilities.

In accordance with aspects of the present disclosure, the operation of pruning images may involve pruning images based on a similarity threshold. In various embodiments, the capsule 110 may include processing capabilities (e.g., processor(s), memory, instructions, etc.) that compare two images to determine overall image similarity. In various embodiments, the capsule 110 may include processing capabilities that compare two images and/or image regions to determine pathology similarity (e.g., similarity of occurrences of a pathology, such as polyp, shown in the two images).

In various embodiments, the process capabilities may implement a pixel-based comparison that compares pixel values to determine their overall image similarity or determine pathology similarity. Persons skilled in the art will understand how to implement pixel-based comparisons. In various embodiments, the processing capabilities may implement a machine learning model (such as, without limitation, a convolutional neural network) that receives two images or receives image portions as inputs and outputs an indication of similarity between the two images or image portions. Such a machine learning model may be a classification model or may be a regression model. An example of a machine learning model that compares two images to determine whether they contain the same pathology or contain different pathologies is described in International Publication No. WO2022/049577A1, which is hereby incorporated by reference herein in its entirety. Other approaches for a capsule to compare two images and/or image portions to determine overall image similarity and/or determine pathology similarity are contemplated to be within the scope of the present disclosure.

A similarity threshold may be used to determine whether two images or pathologies are sufficiently similar. The similarity threshold may be applied to an output value of the comparison or to an intermediate value of the comparison. If the value is below the similarity threshold, the two images or pathologies can be determined to be sufficiently different, such that neither image is pruned. If the value is above the similarity threshold, the two images or pathologies can be determined to be sufficiently similar, such that one of the two images may be pruned. As described in more detailed later herein, different similarity thresholds may be applied depending on the location or segment in the GIT where the capsule captured the images. Images which are not pruned by the capsule 110 may be communicated to a receiver device external to the person, such as communicated to a wearable device 120 worn by or adhered to the person, a mobile device 130 carried by the person, and/or another device (e.g., router or other network device), among other possibilities.

In accordance with aspects of the present disclosure, the operation of pruning images may involve pruning images based on a difference threshold. A difference threshold, in contrast to a similarity threshold, is used to determine whether two images or pathology are sufficiently different. The same techniques described in connection with the similarity threshold may be used in connection with the difference threshold, such as the pixel-based techniques or machine-learning based techniques described above. An example of a machine learning model that compares two images to determine whether they contain the same pathology or contain different pathologies is described in International Publication No. WO2022/049577A1, which was incorporated by reference above. Other approaches for a capsule to compare two images and/or image portions to determine overall image difference and/or determine pathology difference are contemplated to be within the scope of the present disclosure.

A difference threshold may be used to determine whether two images or pathologies are sufficiently different. The difference threshold may be applied to an output value of the comparison or to an intermediate value of the comparison. If the value is above the difference threshold, the two images or pathologies can be determined to be sufficiently different, such that one of the two image may be pruned. If the value is below the difference threshold, the two images or pathologies can be determined to be sufficiently similar, such that neither of the two images is pruned. As described in more detailed later herein, different difference thresholds may be applied depending on the location or segment in the GIT where the capsule captured the images. Images which are not pruned by the capsule 110 may be communicated to a receiver device external to the person, such as communicated to a wearable device 120 worn by or adhered to the person, a mobile device 130 carried by the person, and/or another device (e.g., router or other network device), among other possibilities.

Figure 31:
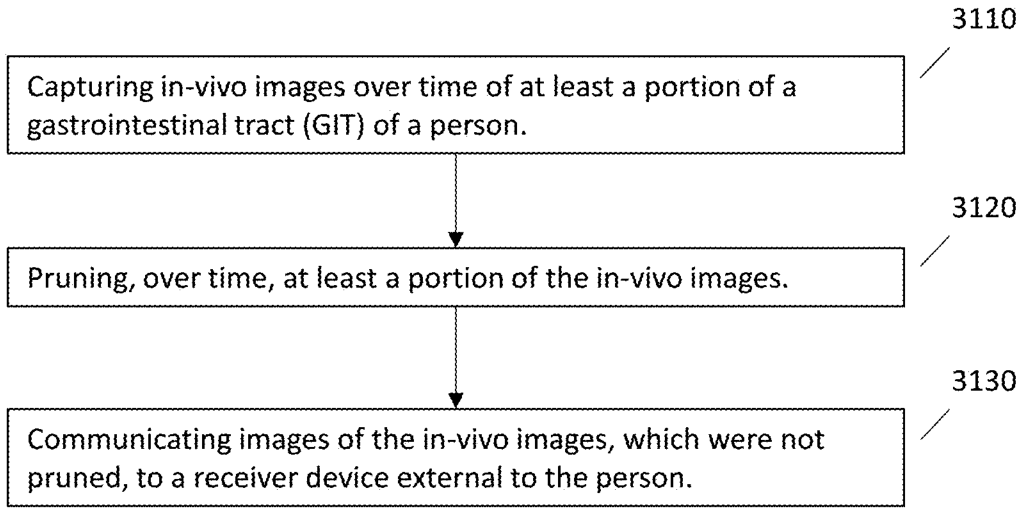
FIG. 31 is a flow diagram of an exemplary operation in a capsule device for pruning images captured in a capsule endoscopy procedure, in accordance with aspects of the present disclosure.

FIG. 31 shows an example of an operation in a capsule device for pruning images. At block 3110, the operation involves capturing in-vivo images over time of at least a portion of a gastrointestinal tract (GIT) of a person. As the capsule traverses the GIT over time, the capsule captures in-vivo images of the GIT as it progresses.

At block 3120, the operation involves pruning, over time, at least a portion of the in-vivo images. In various embodiments, the pruning operation of block 3120 may be performed while the capturing operation of block 3110 occurs. In various embodiments, the capturing operation 3110 and the pruning operation of block 3120 may be performed successively, one after the other. As mentioned above, the pruning operation may apply one or more rates of pruning, may apply one or more similarity threshold, and/or may apply one or more difference thresholds.

At block 3130, the operation involves communicating images of the in-vivo images, which were not pruned, to a receiver device external to the person. The receiver device may be a wearable device worn by or adhered to the person, a mobile device carried by the person, and/or another device (e.g., router or other network device), among other possibilities.

The operation of FIG. 31 is exemplary, and variations are contemplated to be within the scope of the present disclosure. For example, in various embodiments, the operation may include other blocks not shown in FIG. 31. Such and other variations are contemplated to be within the scope of the present disclosure.

Aspects of the present disclosure involve detecting or approximating the location in a gastrointestinal tract (GIT) where a capsule device (e.g., 110, FIG. 1) captured particular images. As mentioned above, different degrees of pruning may be applied based on the location or GIT segment where the capsule captured the images. Various approaches are contemplated for achieving the location detection or approximation.

An approach for estimating images that reflect a transition between adjacent segments of a GIT is described in U.S. Patent Application Publication No. 2023/0148834, by Given Imaging Ltd., which is hereby incorporated by reference herein in its entirety. An approach for classifying images to segments of a GIT is described in U.S. Pat. No. 11,934,491, by Given Imaging Ltd., which is hereby incorporated by reference herein in its entirety. In various embodiments, an approach for detecting that a capsule is in a designated GIT region of interest (such as in a GIT region having a suspected pathology) is disclosed in U.S. Pat. No. 11,918,343, by Given Imaging Ltd., which is hereby incorporated by reference herein in its entirety. These approaches may be utilized to detect or approximate the location(s) in the GIT where a capsule device captured particular images and to provide location indications (e.g., small bowel, colon, or colon segment, etc.) specifying the locations in the GIT where the capsule captured the images. The examples above are merely illustrative, and other approaches for detecting or indication locations within a GIT are contemplated to be within the scope of the present disclosure.

Figure 33:
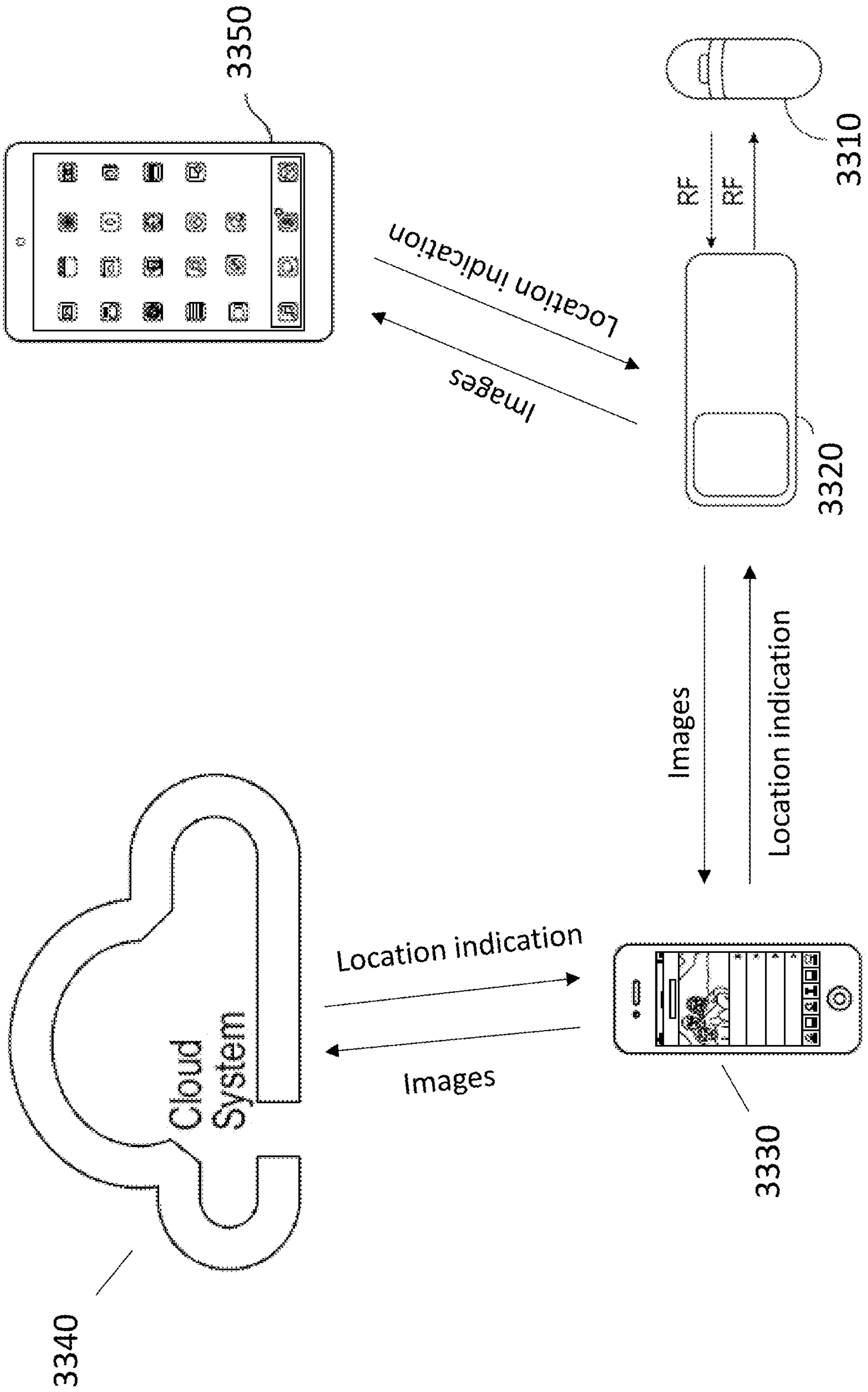
FIG. 33 is a diagram of exemplary devices that may provide location indications specifying locations in a GIT where a capsule device captured images, in accordance with aspects of the present disclosure.

FIG. 33 is a diagram of various devices that may provide location indications for captured images, including a capsule device 3310, a wearable device worn by a person 3320, a mobile device carried by a person 3330, a remote computing system (e.g., cloud system) 3340, and/or a healthcare provide device 3350, among other possibilities.

Where a capsule device 3310 implements the approaches for providing location indications, the capsule device 3310 may process in-vivo images to provide the location indications. Where another device 3320-3350 implements the approaches for providing location indications, such other devices 3320-3350 may receive captured images from the capsule device 3310 and process the received images to provide location indications. The images received by the other devices 3320-3350 include images that were not pruned by the capsule device 3310. The other devices 3320-3350 may then communicate the location indications back to the capsule device to inform the capsule device of the approximate location in the GIT where the images were captured.

Figure 32:
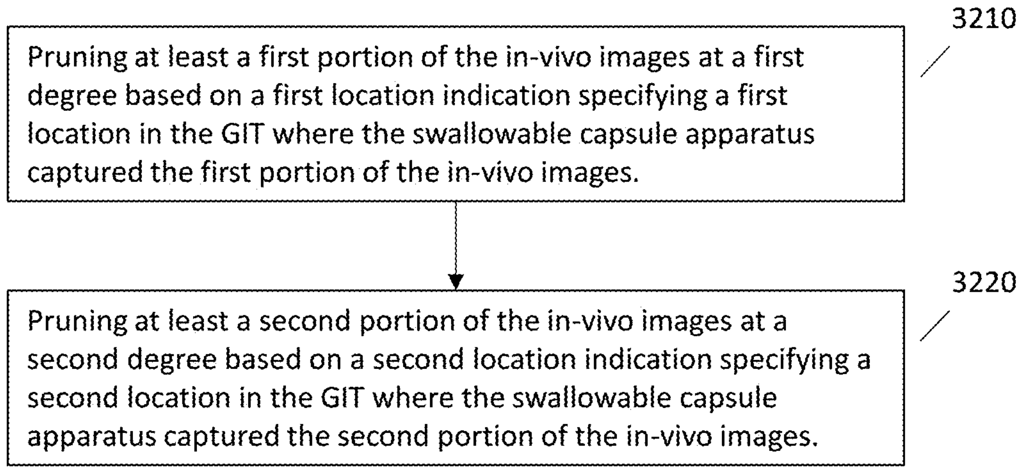
FIG. 32 is a flow diagram of an exemplary operation in a capsule device for pruning images captured in a capsule endoscopy procedure to different degrees based on location, in accordance with aspects of the present disclosure.

FIG. 32 is a flow diagram showing an exemplary operation for a capsule to prune captured in-vivo images at different degrees based on the locations in the GIT where the in-vivo images were captured. At block 3210, the operation involves pruning at least a first portion of the in-vivo images at a first degree based on a first location indication specifying a first location in the GIT where the capsule device captured the first portion of the in-vivo images. As mentioned above the pruning may be performed based on, e.g., a rate of pruning, a similarity threshold, and/or a difference threshold, among other possibilities. The first location indication may be provided by a capsule device, a wearable device, a mobile device, a healthcare provide device, and/or a cloud system, among other possibilities. The degree of pruning that the capsule device performs based on the first location indication may be based on a predetermined rate of pruning, a predetermined similarity threshold, and/or a predetermined difference threshold for the location specified by the first location indication.

At block 3220, the operation involves pruning at least a second portion of the in-vivo images at a second degree based on a second location indication specifying a second location in the GIT where the swallowable capsule apparatus captured the second portion of the in-vivo images. As mentioned above, the pruning may be performed based on, e.g., a rate of pruning, a similarity threshold, and/or a difference threshold, among other possibilities. The second location indication may be provided by a capsule device, a wearable device, a mobile device, a healthcare provide device, and/or a cloud system, among other possibilities. The degree of pruning that the capsule device performs based on the second location indication may be based on a predetermined rate of pruning, a predetermined similarity threshold, and/or a predetermined difference threshold for the location specified by the second location indication.

In various embodiments, the first degree of pruning for the first location may be greater than the second degree of pruning for the second location, such that in-vivo images of the first location are pruned to a greater degree than in-vivo images of the second location. In cases where the first location is a small bowel and the second location is a colon, the degree of pruning images captured in the small bowel may be greater than the degree of pruning images captured in the colon. The higher degree of pruning in the small bowel may be beneficial, for example, because the small bowel is narrower, so a capsule device may travel through a small bowel more slowly and capture many similar images. Therefore, pruning images in the small bowel to a higher degree may reduce the occurrences of redundant images.

In cases where the first location is a location having no suspected pathology and the second location is a location having a suspected pathology, the degree of pruning images captured in the location having no suspected pathology may be greater than the degree of pruning images captured in the location having the suspected pathology. The higher degree of pruning in the location having no suspected pathology may be beneficial, for example, because the is some interest (but less interest) in images of a location having no suspected pathology, and keeping fewer images of such a location saves on capsule device resources.

Other scenarios are contemplated to be within the scope of the present disclosure.

Accordingly, systems, devices, methods, and applications for capsule endoscopy procedures have been described herein. For purposes of explanation, specific configurations and details are set forth in order to provide a thorough understanding of aspects of the disclosed technology. However, it is apparent to one skilled in the art that the disclosed technology can be practiced without using every aspect presented herein.

Unless specifically stated otherwise, as apparent from the preceding discussions, it is appreciated that throughout the specification discussions utilizing terms such as "processing," "computing," "storing," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Different aspects are disclosed herein. Features of certain aspects can be combined with features of other aspects; thus certain aspects can be combinations of features of multiple aspects.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

The systems, devices, and/or servers described herein may utilize one or more processors to receive various information and transform the received information to generate an output. The processors may include any type of computing device, computational circuit, or any type of controller or processing circuit capable of executing a series of instructions that are stored in a memory. The processor may include multiple processors and/or multicore central processing units (CPUs) and may include any type of device, such as a microprocessor, graphics processing unit (GPU), digital signal processor, microcontroller, programmable logic device (PLD), field programmable gate array (FPGA), or the like. The processor may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

While several embodiments of the disclosure have been described herein and/or shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A swallowable capsule apparatus comprising:

one or more processors; and one or more memory storing instructions which, when executed by the one or more processors, cause the swallowable capsule apparatus at least to perform:

capturing in-vivo images over time of at least a portion of a gastrointestinal tract (GIT) of a person;

pruning, over time, at least a portion of the in-vivo images, the pruning comprising:

pruning at least a first portion of the in-vivo images at a first degree based on a first location indication specifying a first location in the GIT where the swallowable capsule apparatus captured the first portion of the in-vivo images, and pruning at least a second portion of the in-vivo images at a second degree based on a second location indication specifying a second location in the GIT where the swallowable capsule apparatus captured the second portion of the in-vivo images; and communicating images of the in-vivo images, which were not pruned, to a receiver device external to the person.

2. The swallowable capsule apparatus of claim 1, wherein the instructions, when executed by the one or more processors, further cause the swallowable capsule apparatus at least to perform:

generating the first location indication based on at least the first portion of the in-vivo images; and generating the second location indication based on at least the second portion of the in-vivo images.

3. The swallowable capsule apparatus of claim 1, wherein the first location indication and the second location indication are generated by at least one of:

a wearable device configured to be secured to the person, a mobile device carried by the person, or a remote computing system remote from the swallowable capsule apparatus.

4. The swallowable capsule apparatus of claim 1, wherein the first location is a small bowel of the person and the second location is a colon of the person, wherein the first degree is greater than the second degree such that in-vivo images of the small bowel are pruned to a greater degree than in-vivo images of the colon.

5. The swallowable capsule apparatus of claim 1, wherein the first location is a location of the GIT having no suspected pathology and the second location is a location of the GIT having a suspected pathology, wherein the first degree is greater than the second degree such that in-vivo images of the location of the GIT having no suspected pathology are pruned to a greater degree than in-vivo images of the location of the GIT having a suspected pathology.

6. The swallowable capsule apparatus of claim 1, wherein the pruning the at least the first portion of the in-vivo images at the first degree is different from the pruning the at least the second portion of the in-vivo images at the second degree by at least one of:

a rate of pruning images, wherein the first degree of pruning has a higher rate of pruning images than the second degree of pruning, a similarity threshold for pruning the in-vivo images, wherein the first degree of pruning has a lower similarity threshold for pruning the in-vivo images than the second degree of pruning, or a difference threshold for pruning the in-vivo images, wherein the first degree of pruning has a higher difference threshold for pruning the in-vivo images than the second degree of pruning.

7. A processor-implemented method in a swallowable capsule apparatus, the method comprising:

capturing, by the swallowable capsule apparatus, in-vivo images over time of at least a portion of a gastrointestinal tract (GIT) of a person;

pruning, by the swallowable capsule apparatus over time, at least a portion of the in-vivo images, the pruning comprising:

pruning, by the swallowable capsule apparatus, at least a first portion of the in-vivo images at a first degree based on a first location indication specifying a first location in the GIT where the swallowable capsule apparatus captured the first portion of the in-vivo images, and pruning, by the swallowable capsule apparatus, at least a second portion of the in-vivo images at a second degree based on a second location indication specifying a second location in the GIT where the swallowable capsule apparatus captured the second portion of the in-vivo images; and communicating, by the swallowable capsule apparatus, images of the in-vivo images, which were not pruned, to a receiver device external to the person.

8. The processor-implemented method of claim 7, further comprising:

generating, by the swallowable capsule apparatus, the first location indication based on at least a first portion of the in-vivo images; and generating, by the swallowable capsule apparatus, the second location indication based on at least a second portion of the in-vivo images.

9. The processor-implemented method of claim 7, wherein the first location indication and the second location indication are generated by at least one of:

a wearable device configured to be secured to the person, a mobile device carried by the person, or a remote computing system remote from the swallowable capsule apparatus.

10. The processor-implemented method of claim 7, wherein the first location is a small bowel of the person and the second location is a colon of the person, wherein the first degree is greater than the second degree such that in-vivo images of the small bowel are pruned, by the swallowable capsule apparatus, to a greater degree than in-vivo images of the colon.

11. The processor-implemented method of claim 7, wherein the first location is a location of the GIT having no suspected pathology and the second location is a location of the GIT having a suspected pathology, wherein the first degree is greater than the second degree such that in-vivo images of the location of the GIT having no suspected pathology are pruned, by the swallowable capsule apparatus, to a greater degree than in-vivo images of the location of the GIT having a suspected pathology.

12. The processor-implemented method of claim 7, wherein the pruning the at least the first portion of the in-vivo images at the first degree is different from the pruning the at least the second portion of the in-vivo images at the second degree by at least one of:

a rate of pruning images, wherein the first degree of pruning has a higher rate of pruning images than the second degree of pruning, a similarity threshold for pruning the in-vivo images, wherein the first degree of pruning has a lower similarity threshold for pruning the in-vivo images than the second degree of pruning, or a difference threshold for pruning the in-vivo images, wherein the first degree of pruning has a higher difference threshold for pruning the in-vivo images than the second degree of pruning.

13. A non-transitory processor-readable medium storing instructions which, when executed by one or more processors in a swallowable capsule apparatus, cause the swallowable capsule apparatus at least to perform:

capturing in-vivo images over time of at least a portion of a gastrointestinal tract (GIT) of a person;

pruning, over time, at least a portion of the in-vivo images, the pruning comprising:

pruning, by the swallowable capsule apparatus, at least a first portion of the in-vivo images at a first degree based on a first location indication specifying a first location in the GIT where the swallowable capsule apparatus captured the first portion of the in-vivo images, and pruning, by the swallowable capsule apparatus, at least a second portion of the in-vivo images at a second degree based on a second location indication specifying a second location in the GIT where the swallowable capsule apparatus captured the second portion of the in-vivo images; and communicating images of the in-vivo images, which were not pruned, to a receiver device external to the person.

14. The non-transitory processor-readable medium of claim 13, wherein the instructions, when executed by the one or more processors, further cause the swallowable capsule apparatus at least to perform:

generating the first location indication based on at least the first portion of the in-vivo images; and generating the second location indication based on at least the second portion of the in-vivo images.

15. The non-transitory processor-readable medium of claim 13, wherein the first location is a small bowel of the person and the second location is a colon of the person, wherein the first degree is greater than the second degree such that in-vivo images of the small bowel are pruned to a greater degree than in-vivo images of the colon.

16. The non-transitory processor-readable medium of claim 13, wherein the first location is a location of the GIT having no suspected pathology and the second location is a location of the GIT having a suspected pathology, wherein the first degree is greater than the second degree such that in-vivo images of the location of the GIT having no suspected pathology are pruned to a greater degree than in-vivo images of the location of the GIT having a suspected pathology.

17. The non-transitory processor-readable medium of claim 13, wherein the pruning the at least the first portion of the in-vivo images at the first degree is different from the pruning the at least the second portion of the in-vivo images at the second degree by at least one of:

a rate of pruning images, wherein the first degree of pruning has a higher rate of pruning images than the second degree of pruning, a similarity threshold for pruning the in-vivo images, wherein the first degree of pruning has a lower similarity threshold for pruning the in-vivo images than the second degree of pruning, or a difference threshold for pruning the in-vivo images, wherein the first degree of pruning has a higher difference threshold for pruning the in-vivo images than the second degree of pruning.

* * * * *